US011535632B2

(12) United States Patent
De Lombaert et al.

(10) Patent No.: US 11,535,632 B2
(45) Date of Patent: *Dec. 27, 2022

(54) SOLID FORMS OF AN S1P-RECEPTOR MODULATOR

(71) Applicant: ESCAPE Bio, Inc., South San Francisco, CA (US)

(72) Inventors: Stéphane De Lombaert, Brisbane, CA (US); Ana Rosario Mool Sarno, San Mateo, CA (US); Michael A. Christie, Phoenixville, PA (US); Edward L. Ciolkowski, Webster, NY (US); Susana del Rio Gancedo, Cambridge (GB); Joseph Stephen Harris, Cambridge (GB); Lucy Kristina Mapp, Cambridge (GB); Mateusz Bogumil Pitak, Cambridge (GB); Scott L. Childs, Atlanta, GA (US)

(73) Assignee: ESCAPE Bio, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/084,713

(22) Filed: Oct. 30, 2020

(65) Prior Publication Data

US 2021/0139502 A1    May 13, 2021

Related U.S. Application Data

(60) Provisional application No. 62/928,412, filed on Oct. 31, 2019.

(51) Int. Cl.
*C07D 498/04* (2006.01)

(52) U.S. Cl.
CPC ........ *C07D 498/04* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 6,380,387 | B1 | 4/2002 | Sidduri et al. |
| 8,796,262 | B2 | 8/2014 | Smid et al. |
| 9,096,612 | B2 | 8/2015 | Smid et al. |
| 9,227,960 | B2 | 1/2016 | Bakker et al. |
| 9,670,220 | B2 | 6/2017 | Smid et al. |
| 9,951,084 | B2 | 4/2018 | Stoit et al. |
| 10,179,791 | B2 | 1/2019 | Stoit et al. |
| 10,179,971 | B2 | 1/2019 | Griffin et al. |
| 10,807,991 | B2 | 10/2020 | Stoit et al. |
| 2003/0203940 | A1 | 10/2003 | Yoshioka et al. |
| 2005/0090520 | A1 | 4/2005 | Lindquist |
| 2005/0187251 | A1 | 8/2005 | Mahaney et al. |
| 2006/0113010 | A1 | 6/2006 | Saitou et al. |
| 2007/0197621 | A1 | 8/2007 | Galley et al. |
| 2009/0023797 | A1 | 1/2009 | Azzaoui et al. |
| 2009/0192154 | A1 | 7/2009 | Maekawara |
| 2009/0321144 | A1 | 12/2009 | Wyble et al. |
| 2010/0069351 | A1 | 3/2010 | Taniguchi et al. |
| 2013/0196998 | A1 | 8/2013 | Stoit et al. |
| 2013/0203737 | A1 | 8/2013 | Smid et al. |
| 2014/0066433 | A1 | 3/2014 | Smid et al. |
| 2015/0284403 | A1 | 10/2015 | Smid et al. |
| 2016/0340363 | A1 | 11/2016 | Stoit et al. |
| 2019/0218227 | A1 | 7/2019 | Stoit et al. |
| 2021/0130364 | A1 | 5/2021 | Stolt et al. |
| 2021/0139503 | A1 | 5/2021 | De Lombaert et al. |

FOREIGN PATENT DOCUMENTS

| | | |
|---|---|---|
| CN | 101490017 | 7/2009 |
| CN | 101511783 | 8/2009 |
| CN | 101812058 | 8/2010 |
| EP | 0431943 | 6/1991 |
| EP | 2364976 | 9/2011 |
| FR | 2822727 | 10/2002 |
| GB | 2228432 | 8/1990 |
| JP | H03206042 | 9/1991 |
| JP | H06248350 | 9/1994 |
| JP | H072848 | 1/1995 |
| JP | H1072623 | 3/1998 |
| JP | 2004211187 | 7/2004 |
| JP | 2007046108 | 2/2007 |
| JP | 2007063642 | 3/2007 |
| SU | 1069387 | 11/1985 |
| WO | WO 1997/017350 | 5/1997 |
| WO | WO 2004/111021 | 12/2004 |
| WO | WO 2005/05829 | 6/2005 |

(Continued)

OTHER PUBLICATIONS

A Study to Assess the Relative Bioavailability of Different Formulations of GSK2018682, a Sphingosine-1-phosphate Receptor Subtype 1 Agonist, in Healthy Volunteers. (P1A114919). (2011) Retrieved from https://clinicaltrials.gov/ct2/show/NCT01466322?term=NCT01466322&rank=1 (Identification No. NCT01466322), 10 pages.
Adlard et al., "A Novel Approach to Rapidly Prevent Age-Related Cognitive Decline," Aging Cell, 2014, 13(2): 351-359.
Aixi et al., "Synthesis and Characterization of 2-Arylmorpholine Hydrochloride," Journal of Hunan University, National Sciences, 2005, 32(4): 72-76.
Aixi et al., "Synthesis and Cyclooxygenase-2 Inhibitory Activity of 2-(2-Arylmorpholino)Ethyl Ester of Naproxen," Acta Chimica Sinica—Chinese Edition. 2008, 66(22): 2553-2557.
Amminger et al., "Omega-3 fatty acids supplementation in children with autism: a double-blind randomized, placebo- [81 ::ontrolled pilot study." Biol Psychiatry, 2007, 61:551-3.

(Continued)

*Primary Examiner* — Craig D Ricci
(74) *Attorney, Agent, or Firm* — Mintz, Levin, Cohn, Ferris, Glovsky and Popeo, P.C.

(57) ABSTRACT

This application relates to solid forms of an S1P-receptor modulator, which are useful in the treatment of diseases or disorders associated with activity of S1P, including CNS disorders.

3 Claims, 23 Drawing Sheets

(56) References Cited

FOREIGN PATENT DOCUMENTS

| WO | WO 2005/058295 | | 6/2005 | |
|---|---|---|---|---|
| WO | WO 2005/063745 | | 7/2005 | |
| WO | WO 2005/105100 | | 11/2005 | |
| WO | WO 2005/105763 | | 11/2005 | |
| WO | WO 2006/047195 | | 5/2006 | |
| WO | WO 2007/057775 | | 5/2007 | |
| WO | WO 2007/85556 | | 8/2007 | |
| WO | WO 2008/012010 | | 1/2008 | |
| WO | WO 2008/079382 | | 7/2008 | |
| WO | WO 2008/129029 | | 10/2008 | |
| WO | WO 2009/092764 | | 7/2009 | |
| WO | WO 2009/097309 | | 8/2009 | |
| WO | WO 2009/097567 | | 8/2009 | |
| WO | WO 2011/023795 | | 3/2011 | |
| WO | WO 2011/095579 | | 8/2011 | |
| WO | WO 2012/004373 | * | 1/2012 | ........... C07D 487/04 |
| WO | WO 2012/004373 | | 2/2021 | |

OTHER PUBLICATIONS

Asle-Rousta et al., "Activation of Sphingosine 1-Phosphate Receptor-1 by Sew2871 Improves Cognitive Function in Alzheimer's Disease Model Rats," Excli. Journal. 2013, 12: 449-461.
Barnes, "Aging and the physiology of spatial memory," Neurobiol. Aging, 1988, 563-8.
Baxter et al., "Reductive Aminations of Carbonyl Compounds with Borohydride and Borane Reducing Agents," John Wiley & Sons, Jan. 2002, 125 pages.
Bellettato et al., "Pathophysiology of Neuropathic Lysosomal Storage Disorders," Journal of Inherited Metabolic Disease, 2010, 33(4): 347-362.
Blom et al., "FTY720 Stimulates 27-Hydroxycholesterol Production and Confers Atheroprotective Effects in Human Primary Macrophages." Circulation Research, 2010, 106(4): 720-729.
BR Office Action in Portuguese Appln. No. 112013000627-7, dated Jul. 8, 2011, 7 pages.
Brailoiu et al., "Sphingosine 1-phosphate enhances spontaneous transmitter release at the frog neuromuscular function," British Journal of Pharmacology, 2002, 136: 1093-1097.
Burdi et al., "Design, synthesis, and structure-activity relationships of novel bicyclic azole-amines as negative allosteric modulators of metabotropic glutamate receptor 5," Journal of Medicinal Chemistry, Oct. 2010, 53(19):7107-7118.
Caira, "Crystalline Polymorphism of Organic Compounds," Design of Organic Solids, Jan. 1, 1998, 163-208 pages.
CAS No. 1215933-90-6, "3-(7-methylspiro[chomene-2,3'-pyrrolidin]-1'-yl) propanoic acid" Retrieved on Aug. 16, 2021, STN entry date: Apr. 4, 2010, 1 Page.
CAS No. 1216083-58-7, "6-methyl-spiro[2H-1-benzopyran-2,4'-piperidine]-1'-acetic acid,6-methyl" Retrieved on Aug. 16, 2021, STN entry date: Apr. 4, 2010, 1 page.
CAS No. 1216208-99-9, "7-ethyl-3,4-dihydro-spiro]2H-1-benzopyran-2,4'-piperidine]-1'acetic acid, 7-ethyl-3,4-dihydro-", Retrieved on Aug. 16, 2021, STN entry date: Apr. 4, 2010, 1 page.
CAS No. 1216214-41-3, "7-methoxy-spiro[2H-1-benzopyran-2,4'-piperidine]-1'-acetic acid, 7-methoxy-" STN entry date: Apr. 4, 2010, 1 page.
CAS No. 1218487-49-0, "2-(6-methylspiro[chromene-2,3'-pyrrolidin]-1'-yl)propanoic acid" STN entry date: Apr. 11, 2010, 3 pages.
CAS No. 1218530-23-4, "2-(6,methoxyspiro[chomene-2,3'-pyrrolidin]-1'-yl)propanoic acid", Retrieved on Aug. 16, 2021, STN entry date: Apr. 22, 2010, 1 page.
CAS No. 1225504-67-5, "2-)6-chloro-5,7-dimethylspiro[chromane-2,3'-pyrrolidin]-1'-yl) acetic acid" STN entry date: May 28, 2010, 3 pages.
CAS No. 1256794-00-9, "Spiro[benzofuran-3(2H), 4'-piperidine], 5-bromo-", Retrieved on Aug. 16, 2021, STN Entry Date Dec. 16, 2010, 1 page.

CAS No. 13808903, "Efficient Synthesis of 5-alkoxy-(3R)-hydroxy-2,3-dihydrospiro[indene-1,4'-piperidines", Retrieved on Feb. 16, 2016, 4 Pages.
Caubere, "Unimetal Super Bases", Chem. Rev., 1993, 93(6):2317-2334.
Chambers et al., "Spiropiperidines as High-Affinity, Selective sigma ligand," Journal of Medicinal Chemistry, 1992, 35(11):2033-2039.
Cheguillaume et al., "A practical synthesis of 2,2-difluoro-3-aminopropanoic acid", Tetrahedron Letters, Mar. 2003, 44(11):2375-2377.
Cieslik et al., "The Molecular Mechanism of Amyloid β42 Peptide Toxicity: The Role of Sphingosine Kinase-1 and Mitochondrial Sirtuins," PLoS One, Sep. 2015, 10(9):1-19.
Clinical Study to Evaluate the Efficacy, Safety, and Tolerability of ACT-128800 in Patients with Relapsing-remitting Multiple Sclerosis. (2009) Retrieved from https://clinicaltrials.gov/ct2/show/NCT0106265?term=CNT01006265&rank=1 (Identification No. NCT01006265), 7 pages.
Coste et al., "Antinociceptive Activity of the SIP-Receptor Agonist FTY720," Journal of Cellular and Molecular Medicine, 2008, 12(3): 995-1004.
Couttas et al., Loss of the neuroprotective factor Sphingosime-1-phosphate early in Alzheimer's disease pathogenesis, Acta Neuropathologica Communications, 2(9): 1-13 (2014).
Crooks et al., "The Synthesis and Analgesic Activities of Some Spiro[indan-1,3'-pyrrolidine] Derivatives Designed as Rigid Analogs of Profadol," American Pharmaceutical Association, Mar. 1982, 71(3): 291-294.
Cutler et al., "Involvement of Oxidative Stress-Induced Abnormalities in Ceramide and Cholesterol Metabolism in Brain Aging and Alzheimer's Disease," Proceedings of the National Academy of Sciences of the United States of America, 2004, 101(7): 2070-2075.
Deary et al., "Age-associated cognitive decline," Br. Med. Bulletin, 2009, 92(1):135-152.
Dember et al., "Spontaneous alternation behavior," Psychol. Bull., 1958, 55(6):412-427.
Deogracias et al., "Fingolimod, a sphingosine-1 phosphate receptor modulator, increases BDNF levels and improves symptoms of a mouse model of Rett syndrome," Proc. Natl. Acad. Sci. USA, 2012, 109(35): 14230-5.
Di Nuzzo et al., "Antidepressant activity of fingolimoid in mice," Pharmacol. Res. Perspect, 2015, 3(3): 1-17.
Doi et al., "Fingolimoid Phosphate Attenuates Oligomeric Amyloid β-Induced Neurotoxicity via Increased Brain-Derived Neurotrophic Factor Expression in Neurons," PLoS One, Apr. 2013. 8(4):e61988.
Donaldson et al., "A study of Heck cyclization reactions to form phenanthridine ring systems," Tetrahedron, 2008, 64:4468-4477.
Doorn et al., "Sphingosine 1-Phosphate Receptor 5 Mediates the Immune Quiescence of the Human Brain Endothelial Barrier," Journal of Neuroinflammation, 2012, 20(9): 133, 15 pages.
EC Office Action in Spanish Appln No. 2.12325, dated Jul. 6, 2021, 9 pages.
EP Office Action for European Patent Application No. 11733645.3 dated Oct. 20, 2016, 9 pages.
European Search Report for Application No. EP16191215, dated Dec. 5, 2016, 7 pages.
Farr et al., "Spingosine-1-phosphate Receptor 5 Agonist A-971432 Improves Leaning and Memory in the SAMP8 Mouse Model of Alzheimer's Disease," Alzheimer's & Dementia, 2017, 13(7):Suppl. p. 949.
Foster et al., "FTY720 Rescue Therapy in the Dark Agouti Rat Model of Experimental Autoimmune Encephalomyelitis: Expression of Central Nervous System Genes and Reversal of Blood-Brain-Barrier Damage," Brain Pathology, 2009, 19: 254-266.
Fukumoto et al., "Fingolimod increases brain-derived neurotrophic factor levels and ameliorates amyloid β-induced memory impairment," Behavioural Brain Res., 2014, 268: 88-93 (2014).
Fukuzako et al., "Changes in Levels of Phosphorus Metabolites in Temporal Lobes of Drug-Naïve Schizophrenic Patients," The American Journal of Psychiatry, 1999, 156(8): 1205-1208.
Gerlai, "A new continuous alternation task in T-maze detects hippocampal dysfunction in mice. A strain comparisoin and lesion study," Behav. Brain. Res., 1998, 95(1):91-101.

(56) References Cited

OTHER PUBLICATIONS

Gomez-Brouchet et al., "Critical Role for Sphingosine Kinase-1 in Regulating Survival of Neuroblastoma Cells Exposed to Amyloid-β Peptide," Mol. Pharmacol., 72(2): 341-349 (2007).
Gottfries et al., "Therapy options in Alzheimer's Disease," British Journal of Clinical Practice, 1994, 48(6): 327-330.
Grassi et al., "Sphingosine 1-Phosphate Receptors and Metabolic Enzymes as Druggable Targets for Brain Diseases," Frontiers in Pharmacology, 2019, 20 pages.
Gregg et al., "Gene Expression Changes in Children with Autism," Genomics, 2008, 91(1): 22-29.
Hait et al., "Active, phosphorylated fingolimoid inhibits histone deacetylases and facilitates fear extrinction memory," Nat. Neurosci., 2014, 17(7): 971-980, 30 pages.
Hait et al., "Regulation of Histone Acetylation in the Nucleus by Sphingosine-1-Phosphate," Science, 2009, 325(5945): 1254-1257.
Han et al., "Substantial Sulfatide Deficiency and Ceramide Elevation in Very Early Alzheimer's Disease: Potential Role in Disease Pathogenesis," Journal of Neurochemistry, 2002, 82(4): 809-818.
Harada et al., "Sphingosine-1-Phosphate Induces Proliferation and Morphological Changes of Neural Progenitor Cells," Journal of Neurochemistry, 2004, 88(4): 1026-1039.
Helquist et al., "Treatment of Niemann-Pick Type C Disease by Histone Deacetylase Inhibitors," Neurotherapeutics, 2013, 10: 688-697.
Hicks et al., "Genetic Determinants of Circulating Sphingolipid Concentrations in European Populations," PLOS Genetics, 2009, 5(10): e1000672, 11 pages.
Hobson et al., "Discovery of A-971432, An Orally Bioavailable Selective Sphingosine-1-phosphate receptor 5 (S1P5) Agonist for Potential Treatment of Neurodegenerative Disorders," J. Med. Chem., 2015, 58(23): 9154-70, 38 pages.
Hussain et al., "Applications of 1-Alkenyl-1,1-Heterobimetallics in the Stereoselective Synthesis of Cyclopropylboronate Esters, Trisubstituted Cyclopropanols and 2,3-Disubstituted Cyclobutanones," J. Am. Chem. Soc., 2009, 131:6516, 41 pages.
International Search Report and Written Opinion for Application No. PCT/EP2011006156, dated Mar. 8, 2012, 9 pages.
International Search Report and Written Opinion for Application No. PCT/EP2011/061586, dated Aug. 25, 2011, 17 pages.
Interational Search Report and Written Opinion for Application No. PCT/EP2011/061590, dated Aug. 12, 2011, 8 pages.
International Search Report and Written Opinion for Application No. PCT/EP2011/061599, dated Sep. 20, 2011, 12 pages.
International Search Report and Written Opinion in International Application No. PCT/EP2010/062552, dated Oct. 14, 2010, 11 pages.
International Search Report and Written Opinion in International Appln. No. PCT/US2020/058269, dated Jan. 25, 2021, 14 pages.
International Search Report and Written Opinion in International Appln. No. PCT/US2020/058259, dated Feb. 12, 2021, 18 pages.
International Search Report for Application No. PCT/EP2010/062552, dated Sep. 27, 2010, 4 pages.
Jaillard et al., "EDG8/S1P5: An Oligodendroglial Receptor with Dual Function on Process Retraction and Cell Survival," The Journal of Neuroscience: the Official Journal of the Society for Neuroscience, 2005, 25(6): 1459-1469.
Jo et al., "Sphingosine-1-Phosphate Receptors: Biology and Therapeutic Potential in Kidney Disease," Kidney International, 2008, 73(11): 1220-1230.
Kajimoto el al., "Involvement of Sphingosine-1-Phosphate in Glutamate Secretion in Hippocampal Neurons," Molecular and Cellular Biology, 2007, 27(9): 3429-3440.
Kaneider et al., "The Immune Modulator FTY720 Targets Sphingosine-Kinase-Dependent Migration of Human Monocytes in Response to Amyloid Beta-Protein and its Precursor," The FASEB Journal, 2004, 18(11): 1309-1311, 10 pages.
Kanno et al., "Regulation of Synaptic Strength by Sphingosine 1-Phosphate in the Hippocampus," Neuroscience, 2010, 171(4): 973-980.
Karimi, "Transition-Metal_Catalyzed Oxidative Heck Resolutions", Synthesis, 2010, 1399-1427.
Kim et al., "Role of ATP-Binding Cassette Transporters in Brain Lipid Transport and Neurological Disease," Journal of Neurochemistiy, 2008, 104(5): 1145-1166.
Kornhuber el al., "The role of ceramide in major depressive disorder," European Archives of Psychiatry and Clinical Neuroscience, 2009, 259: 199-204.
Kurlak et al., "Plausible explanations for effects of long chain polyunsaturated fatty acids (LCPUFA) on neonates," Arct [81 Dis Child Fetal Neonatal Ed, 1999 80:F148-54.
Lahiri et al., "Ceramide Synthesis is Modulated by the Sphingosine Analog FTY720 Via a Mixture of Uncompetitive and Noncompetitive Inhibition in an Acyl-Coa Chain Length-Dependent Manner," The Journal of Biological Chemistry, 2009, 284(24): 16090-16098.
Lee et al., "Bone Marrow-Derived Mesenchymal Stem Cell Prevent the Loss of Niemann-Pick Type C Mouse Purkinje Neurons by Correcting Sphingolipid Metabolism and Increasing Sphingosine-1-Phosphate," Stem Cells, (Dayton, Ohio), 2010, 28(4): 821-831.
Lloyd-Evans et al., "Niemann-Pick disease type C1 is a sphingosine storage disease that causes deregulation of lysosomal calcium," Nature Medicine, 14(11): 1247-1255 (2008).
Lorenz et al., "A Novel Class of Tunable Zinc Reagents (RXZnCH2Y) for Efficient Cyclopropanation of Olefins," J. Org. Chem., 2004, 69(2):327-334.
Maceyka et al., "Sphingosine-1-Phosphate Signaling and Its Role in Disease," Trends in Cell Biology, 2012, 22(1): 50-60.
Macqueen et al., "Neuropsychiatric Aspects of the Adult Variant of Tay-Sachs Disease," The Journal of Neuropsychiatry and Clinical Neurosciences, 1998, 10(1): 10-19.
Malaplate-Armand et al., "Soluble oligomers of amyloid-β peptide induce neuronal apoptosis by activating a cPLA2-dependent sphingomyelinase-ceramide pathway," Neurobiology of Disease, 23: 178-189 (2006).
Mattes et al., "Design and Synthesis of Selective and Potent Orally Active S1P5 Agonists," ChemMedChem, 2010, 5(16): 1693-1696.
McCracken et al., "Risperidone in Children with Autism and Serious Behavioral Problems," NEJM, 2002, 347: 314-321.
Miron et al., "Central Nervous System-Directed Effects of FTY720 (Fingolimod)," Journal of the Neurological Sciences, 2008, 274(1-2): 13-17.
Miron et al., "Cyclical and Dose-Dependent Responses of Adult Human Mature Oligodendrocytes to Fingolimoid," The American Journal of Pathology, 2008, 173(4): 1143-1152.
Miron et al., "Fingolimod (FTY720) Enhances Remyelination Following Demyelination of Organotypic Cerebellar Slices," The American Journal of Pathology, 2010, 176(6):2682-2694.
Narayan et al., "Evidence for disruption of sphingolipid metabolism in schizophrenia," Journal of Neuroscience Research, 2009, 87(1): 278-288, 22 pages.
Novgorodov et al., "Activation of Sphingosine-1-Phosphate Receptor S1P5 Inhibits Oligodendrocyte Progenitor Migration," Faseb Journal: Official Publicatino of the Federatino of American Societies for Experimental Biology, 2007, 21(7): 1503-1514.
Pahnke et al., "Alzheimer's Disease and Blood-Brain Barrier Function—Why have Anti-Beta-Amyloid Therapies Failed to Prevent Dementia Progression?," Neuroscience and Biobehavioral Reviews, 2009, 33(7): 1099-1108, 21 pages.
Phase 2 Extension Trial in Patients with Relapsing-Remitting Multiple Sclerosis (RRMS) (DreaMS) (2010) Retrieved from https://clinicaltrials.gov/ct2/show/NCT01226745?term=NCT01226745&rank=1 (Identification No. 01226745), 10 pages.
Rautio et al., "Prodrugs: design and clinical applications," Nat Rev Drug Discov, 2008, 7:255-270.
Roberts et al., "Scientific Report 2007", The Scripps Research Institute, 2007, 4 pages.
Safety, Tolerability, Efficacy and Optimal Dose Finding Study of BAF312 in Patients with Relapsing=remitting Multiple Sclerosis. (2009) Retrieved from https://clinicaltrials.gov/ct2/show/NCT00879658?term-NCT00879658&rank=1 (Identification No. NCT00879658), 11 pages.
Sanchez et al., "Phosphorylation and Action of the Immunomodulator FTY720 Inhibits Vascular Endotheliial Cell Growth Factor-

(56) References Cited

OTHER PUBLICATIONS

Induced Vascular Permeability," The Journal of Biological Chemistry, 2003, 278(47): 47281-47290.
Sim-Selley et al., "Sphingosine-1-Phosphate Receptors Mediate Neuromodulatory Functions in the CNS," Journal of Neurochemistry, 2009, 110(4): 1191-1202, 20 pages.
Subei et al., "Sphingosine 1-Phosphate Receptor Modulators in Multiple Sclerosis," CNS Drugs, 2015, 29(7): 565-575.
Takabe et al., "Inside-Out Signaling of Sphingosine-1-Phosphate: Therapeutic Targets," Pharmacological Reviews, 2008, 60(2): 181-195.
Takasugi et al., "Bacel Activity is Modulated by Cell-Associated Sphingosine-1-Phosphate," The Journal of Neuroscience: the Official Journal of the Society for Neuroscience, 2011, 31(18): 6850-6857.
Takasugi et al., "Fty720/Fingolimod, a Sphingosine Analogue, Reduces Amyloid-i2 Production in Neurons," Plos One, May 2013, 8(5): e64050, 8 pages.
Torrado, "Synthesis of substituted tetralones as intermediates of CNS agents via palladium-catalyzed cross-coupling reactions", Tetrahedron Letters, 48, 2007, 323-326.
Uno et al., "Vinyl MIDA boronate: a readily accessible and highly versatile building block for small molecule synthesis," Tetrahedron, 2009, (65):3130-3138.
Urata et al., "Sphingosine 1-phosphate Induces Alpha-smooth Muscle Actin Expression in Lung Fibroblasts via Rho-kinase", Kobe. J. Med. Sci., 2005, 51(1):17-27.
UY Office Action in Spanish Appln. No. 33496, dated Apr. 20, 2021, 12 pages (with translation).
Van den hoogenband et al., "Ruphose-mediated Suzuki cross-coupling of a secondary alkyl trifluoroborates," Tetrahedron Letters, 2008, 49:4122-4124.
Van den Hoogenband, "A simple, base-free preparation of S-aryl thioacetates as surrogates for aryl thiols," Tetrahedron Letters, Dec. 2010, 51(52):6877-6881.
Van der Kam et al., "The Use of Selective Sphingosine-1-phosphate Receptor 5 Agonists for the Treatment of Neurodegenerative Disorders such as Alzheimer's Disease and Lysosomal Storage Diseases such as Niemann-Pick C Disease," Alheimer's & Dementia, 2014, 10(4S):p. 281-p. 281.
Vidal et al., "Mapping Corpus Callosum Defects in Autism: An Index of Aberrant Cortical Connectivity," Biol. Psychiatry, 60(3): 218-25.
Walzer et al., "Natural Killer Cell Trafficking in Vivo Requires a Dedicated Sphingosine 1-Phosphate Receptor," Nature Immunology, 2007, 8(12): 1337-1344.
Wang et al., "Potential serum biomarkers from a metabolomics study of autism," J. Psychiatry Neurosci., 2016, 41(1): 27-37.
Wemuth et al . "Designing Prodrugs and Bioprecursors 1: Carrier prodrugs," The Practice of Medicinal Chemistry, Academic Press, 1996, 672-696.
Willis et al., "2-(2-Haloalkenyl)-aryl Halides as Substrates for Palladium-Catalysed Tandem C—N Bond Formation: Efficient Synthesis of 1-Substituted Indoles", Adv. Synth. Catal., May 2006, 348(7-8):851-856.
Yordanova et al., "2-(Arylmorpholino) Ethanols and Some of their Derivatives," Farmatsiya, 1998, 45(1): 3-11.
Yu et al, "Characterization of Lysophosphatidic Acid and Sphingosine-1-Phosphate-Mediated Signal Transduction in Rat Cortical Oligodendrocytes," Glia, 2004, 45(1): 17-27.
Yui et al., "Effects of large doses of arachidonic acid added to DHA on social impairment in individuals with autism [81 spectrum disorders: a double-blind, placebo-controlled, randomized trial," J Clin Psychopharmacol, 2012, 32:200-6.
Yutilov et al., "Synthesis and antiviral activity of spinaceamine derivatives," XP002613847, retrived from STN Database accession No. 1989:165603 abstract and Khimiko-Farmatsevticheskii Zhurnal, 1989, 23(1):56-9, 4 pages.
Yutilov et al., "Synthesis and Biological Activity of N-4-beta-hydroxyethylspinaceamines," Khimiko-Farmatsevticheskii Zhurnal, 1989, 23(2): 160-163, 2 pages.
Zhang et al., "Intracellular sphingosine 1-phosphate mediates the increased excitability produced by nerve growth factor in rat sensory neurons," J. Phsyiol., 575(1): 101-113 (2006).

\* cited by examiner

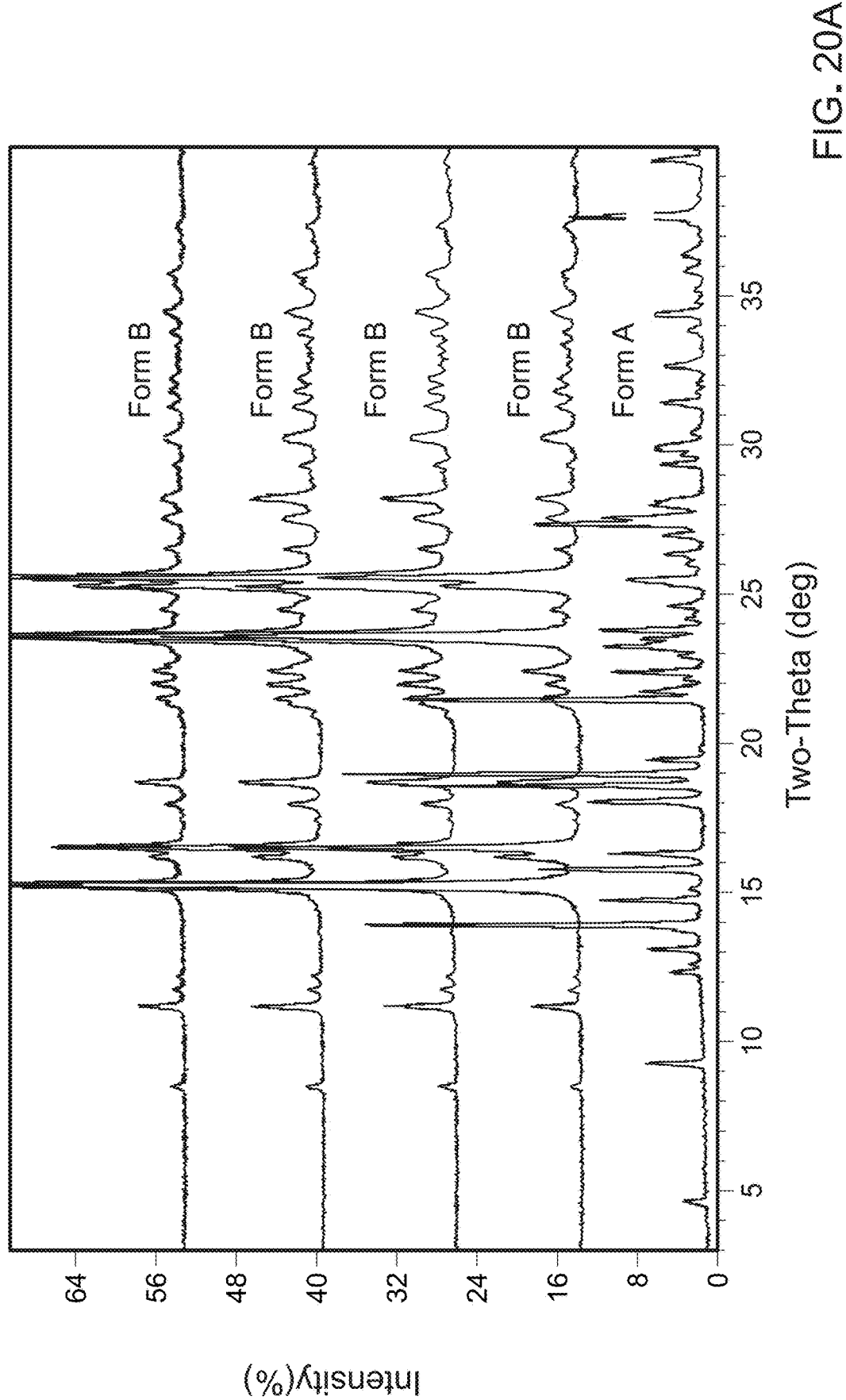

SOLID FORMS OF AN S1P-RECEPTOR MODULATOR

FIELD OF THE INVENTION

This application relates to solid forms of an S1P-receptor modulator, which are useful in the treatment of diseases or disorders associated with activity of S1P, including CNS disorders.

BACKGROUND OF THE INVENTION

Sphingosine-1-phosphate (S1P) is a bioactive sphingolipid that mediates a wide variety of cellular responses, such as proliferation, cytoskeletal organization and migration, adherence and tight junction assembly, and morphogenesis. S1P can bind with members of the endothelial cell differentiation gene family (EDG receptors) of plasma membrane-localized G protein-coupled receptors. To date, five members of this family have been identified as S1P receptors in different cell types, S1P1 (EDG-1), S1P2 (EDG-5), S1P3 (EDG-3), S1P4 (EDG-6) and S1P5 (EDG-8). SP can produce cytoskeletal re-arrangements in many cell types to regulate immune cell trafficking, vascular homeostasis and cell communication in the central nervous system (CNS) and in peripheral organ systems.

It is known that S1P is secreted by vascular endothelium and is present in blood at concentrations of 200-900 nanomolar and is bound by albumin and other plasma proteins. This provides both a stable reservoir in extracellular fluids and efficient delivery to high-affinity cell-surface receptors. SP binds with low nanomolar affinity to the five receptors S1P1-5. In addition, platelets also contain S1P and may be locally released to cause e.g. vasoconstriction. The receptor subtypes S1P1, S1P2 and S1P3 are widely expressed and represent dominant receptors in the cardiovascular system. Further, S1P1 is also a receptor on lymphocytes. S1P4 receptors are almost exclusively in the haematopoietic and lymphoid system. S1P5 is primarily (though not exclusively) expressed in central nervous system. The expression of S1P5 appears to be restricted to oligodendrocytes in mice, the myelinating cells of the brain, while in rat and man expression at the level of astrocytes and endothelial cells was found but not on oligodendrocytes.

S1P receptor modulators are compounds which signal as (ant)agonists at one or more S1P receptors. The present invention relates to modulators of the S1P5 receptor, in particular agonists, and preferably to agonists with selectivity over S1P1 and/or S1P3 receptors, in view of unwanted cardiovascular and/or immunomodulatory effects. It has now been found that S1P5 agonists can be used in the treatment of cognitive disorders, in particular age-related cognitive decline.

Research is ongoing to develop therapeutics that can be used to treat age related cognitive decline and dementia. For example, the compound (1s,3s)-3-(2-(4-((4-chlorobenzyl)oxy)phenyl)-6,7-dihydrooxazolo[4,5-c]pyridin-5(4H)-yl)cyclobutane-1-carboxylic acid and other small molecule modulators of the S1P receptors are reported in, e.g., U.S. Pat. No. 8,796,262. Accordingly, there is a need for new solid forms of SP receptor modulators for preparing pharmaceutically useful formulations and dosage forms with suitable properties related to, for example, facilitating the manufacture of safe, effective, and high quality drug products.

SUMMARY OF THE INVENTION

Provided herein are solid forms of (1s,3s)-3-(2-(4-((4-chlorobenzyl)oxy)phenyl)-6,7-dihydrooxazolo[4,5-c]pyridin-5(4H)-yl)cyclobutane-1-carboxylic acid ("Compound 1").

Provided herein are also pharmaceutical compositions, which include the solid forms as described herein, and one or more pharmaceutically acceptable carriers or excipients.

The present disclosure also provides methods of modulating S1P receptor (e.g., S1P5) activity, comprising contacting Compound 1 or a solid form thereof with an S1P receptor. The present invention further provides a method for treating a CNS disorder in a patient, comprising: administering to the patient a therapeutically effective amount of a solid form of Compound 1.

The present disclosure also provides therapeutic methods of using the solid forms as described herein. The present disclosure also provides uses of the solid forms described herein in the manufacture of a medicament for use in therapy. The present disclosure also provides the solid forms described herein for use in therapy.

BRIEF DESCRIPTION OF THE DRAWINGS

FIG. 20A shows an XRPD overlay of solids obtained from the water activity study described in Example 21, experiments 21A-21D.

DETAILED DESCRIPTION

Figure 1:
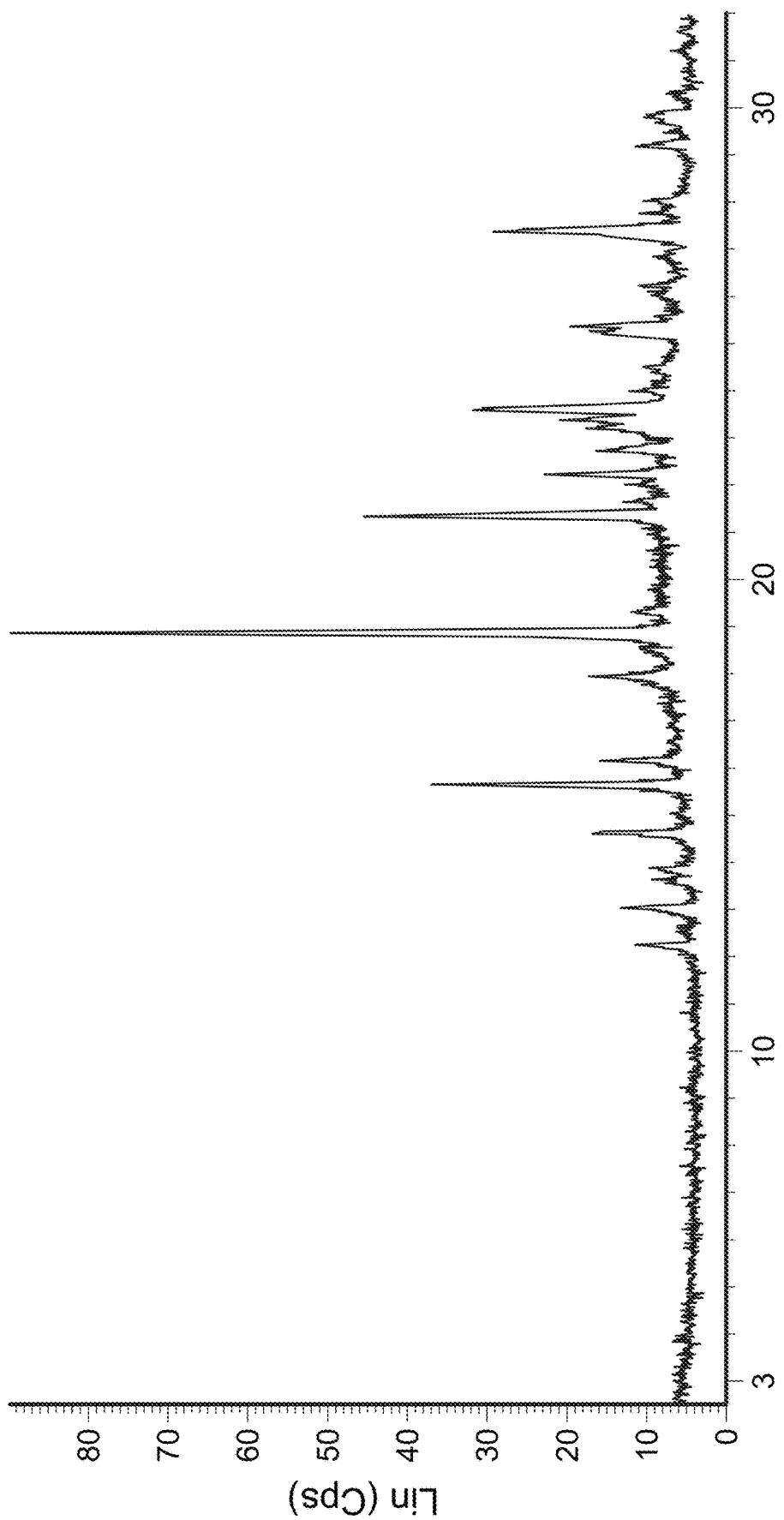
FIG. 1 shows an X-ray powder diffraction (XRPD) pattern of Compound 1, Form A.

The present disclosure is directed to, inter alia, solid forms, including crystalline forms and amorphous forms, of (1s,3s)-3-(2-(4-((4-chlorobenzyl)oxy)phenyl)-6,7-dihydrooxazolo[4,5-c]pyridin-5(4H)-yl)cyclobutane-1-carboxylic acid (Compound 1). The structure of Compound 1 is shown below.

Compound 1

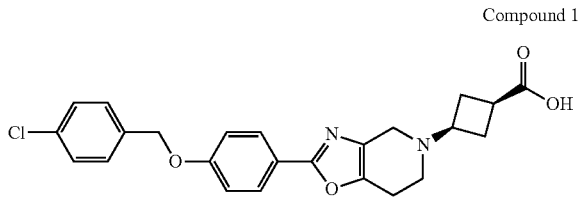 [SMILES: O=C(O)[C@H]1C[C@@H](N2CCc3oc(-c4ccc(OCc5ccc(Cl)cc5)cc4)nc3C2)C1]

Compound 1 is described in U.S. Pat. No. 8,796,262, the entirety of which is incorporated herein by reference.

Compound 1 can be isolated as one or more solid forms. The solid forms (e.g., crystalline forms) described herein can have certain advantages, for example, they may have desirable properties, such as ease of handling, ease of processing, storage stability, and ease of purification. Moreover, the crystalline forms can be useful for improving the performance characteristics of a pharmaceutical product such as dissolution profile, shelf-life and bioavailability.

As used herein, and unless otherwise specified, the term "about", when used in connection with a numeric value or range of values which is provided to describe a particular solid form (e.g., a specific temperature or temperature range, such as describing a melting, dehydration, or glass transition; a mass change, such as a mass change as a function of temperature or humidity; a solvent or water content, in terms of, for example, mass or a percentage; or a peak position, such as in analysis by, for example, $^{13}$C NMR, DSC, TGA and XRPD), indicate that the value or range of values may deviate to an extent deemed reasonable to one of ordinary skill in the art while still describing the particular solid form. Specifically, the term "about", when used in this context, indicates that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values while still describing the particular solid form. The term "about", when used in reference to a degree 2-theta value refers to +/−0.2 degrees 2-theta.

As used herein, the phrase "solid form" refers to a compound provided herein in either an amorphous state or a crystalline state ("crystalline form" or "crystalline solid" or "crystalline solid form"), whereby a compound provided herein in a crystalline state may optionally include solvent or water within the crystalline lattice, for example, to form a solvated or hydrated crystalline form. In some embodiments, the compound provided herein is in a crystalline state as described herein.

As used herein, the term "peak" or "characteristic peak" refers to an XRPD reflection having a relative height/intensity of at least about 3% of the maximum peak height/intensity.

As used herein, the term "crystalline" or "crystalline form" refers to a crystalline solid form of a chemical compound, including, but not limited to, a single-component or multiple-component crystal form, e.g., including solvates, hydrates, clathrates, and a co-crystal. For example, crystalline means having a regularly repeating and/or ordered arrangement of molecules, and possessing a distinguishable crystal lattice. The term "crystalline form" is meant to refer to a certain lattice configuration of a crystalline substance. Different crystalline forms of the same substance typically have different crystalline lattices (e.g., unit cells), typically have different physical properties attributed to their different crystalline lattices, and in some instances, have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the crystalline form as well as help determine stability and solvent/water content.

Different crystalline forms of a particular substance, such as Compound 1 as described herein, can include both anhydrous forms of that substance and solvated/hydrated forms of that substance, where each of the anhydrous forms and solvated/hydrated forms are distinguished from each other by different XRPD patterns, or other solid state characterization methods, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters used, the sample mounting procedure, and the particular instrument employed. In some instances, new peaks may be observed or existing peaks may disappear, depending on the type of the machine or the settings (for example, whether a Ni filter is used or not). As used herein, the term "peak" refers to a reflection having a relative height/intensity of at least about 3% or at least about 4% of the maximum peak height/intensity. Moreover, instrument variation and other factors can affect the 2-theta values. Thus, peak assignments, such as those reported herein, can vary by plus or minus about 0.2° (2-theta) and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures is understood to accommodate such variation.

Crystalline forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, exposure to moisture, grinding and solvent-drop grinding.

As used herein, the term "amorphous" or "amorphous form" is intended to mean that the substance, component, or product in question is not crystalline as determined, for instance, by XRPD or where the substance, component, or product in question, for example is not birefringent when viewed microscopically. For example, amorphous means essentially without regularly repeating arrangement of molecules or lacks the long range order of a crystal, i.e., amorphous form is non-crystalline. An amorphous form does not display a defined x-ray diffraction pattern with sharp maxima. In certain embodiments, a sample comprising an amorphous form of a substance may be substantially free of other amorphous forms and/or crystalline forms. For example, an amorphous substance can be identified by an XRPD spectrum having an absence of reflections.

As used herein, the term "substantially amorphous" means a majority of the weight of a sample or preparation of Compound 1 is amorphous and the remainder of the sample is a crystalline form of the same compound. In some embodiments, a substantially amorphous sample has less than about 5% crystallinity (e.g., about 95% of the non-crystalline form of the same compound), less than about 4% crystallinity (e.g., about 96% of the non-crystalline form of the same compound), less than about 3% crystallinity (e.g., about 97% of the non-crystalline form of the same compound), less than about 2% crystallinity (e.g., about 98% of the non-crystalline form of the same compound), less than about 1% crystallinity (e.g., about 99% of the non-crystalline form of the same compound), or about 0% crystallinity (e.g., about 100% of the non-crystalline form of the same compound). In some embodiments, the term "fully amorphous" means less than about 99% or about 0% crystallinity.

Compound 1 can be prepared in batches referred to as batches, samples, or preparations. The batches, samples, or preparations can include Compound 1 in any of the crystalline or non-crystalline forms described herein, including hydrated and non-hydrated forms, and mixtures thereof.

Compounds provided herein (e.g., Compound 1) can also include all isotopes of atoms occurring in the intermediates or final compounds. Isotopes include those atoms having the same atomic number but different mass numbers. For example, isotopes of hydrogen include tritium and deuterium. One or more constituent atoms of the compounds provided herein can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

In some embodiments, Compound 1 is substantially isolated. The term "substantially isolated" means that the compound is at least partially or substantially separated from the environment in which it was formed or detected. Partial separation can include, e.g., a composition enriched in the compound, salts, hydrates, solvates, or solid forms provided herein. Substantial separation can include compositions containing at least about 50%, at least about 60%, at least about 70%, at least about 80%, at least about 90%, at least about 95%, at least about 97%, or at least about 99% by weight of the compound, salts, hydrates, solvates, or solid forms provided herein.

The term "hydrate," or "hydrated," as used herein, is meant to refer to a solid form of Compound 1 that includes water. The water in a hydrate can be present in a stoichiometric amount with respect to the amount of salt in the solid, or can be present in varying amounts, such as can be found in connection with channel hydrates. Example hydrates include hemihydrate, monohydrate, and dihydrate. Similarly, the term "solvate," or "solvated," refers to a solid form of Compound 1 that include solvent. The solvent can be a non-aqueous solvent.

As used herein, the term "substantially" when referring to a characteristic figure of a crystal form, such as an XRPD pattern, a DSC thermogram, a TGA thermogram, or the like, means that a subject figure may be non-identical to the reference depicted herein, but it falls within the limits of experimental error and thus may be deemed as derived from the same crystal form as disclosed herein, as judged by a person of ordinary skill in the art.

As used herein, the term "crystalline," or "substantially crystalline," means a majority of the weight of a sample or preparation of Compound 1 is crystalline and the remainder of the sample is a non-crystalline form (e.g., amorphous form) of the same compound. In some embodiments, a substantially crystalline sample has at least about 50%, about 60%, about 70%, about 80%, or about 90% crystallinity. In some embodiments, a substantially crystalline sample has at least about 95% crystallinity (e.g., about 5% of the non-crystalline form of the same compound), at least about 96% crystallinity (e.g., about 4% of the non-crystalline form of the same compound), at least about 97% crystallinity (e.g., about 3% of the non-crystalline form of the same compound), at least about 98% crystallinity (e.g., about 2% of the non-crystalline form of the same compound), at least about 99% crystallinity (e.g., about 1% of the non-crystalline form of the same compound), or about 100% crystallinity (e.g., about 0% of the non-crystalline form of the same compound). In some embodiments, the term "fully crystalline" means at least about 99% or about 100% crystallinity.

As used herein, the term "% crystallinity" or "crystalline purity," means percentage of a crystalline form in a preparation or sample which may contain other forms such as an amorphous form of the same compound, or at least one other crystalline form of the compound, or mixtures thereof. In some embodiments, the crystalline forms can be isolated with a crystalline purity of at least about 80%, about 85%, about 90%, about 95%, about 96%, about 97%, about 98%, or about 99%. In some embodiments, the crystalline forms can be isolated with a purity greater than about 99%.

As used herein, the term "reacting" is used as known in the art and generally refers to the bringing together of chemical reagents in such a manner so as to allow their interaction at the molecular level to achieve a chemical or physical transformation. In some embodiments, the reacting involves at least two reagents, wherein one or more molar equivalents of second reagent are used with respect to the first reagent. In some embodiments, the reacting step of a synthetic process may involve one or more substances in addition to the reagents such as solvent and/or a catalyst. The reacting steps of the processes described herein can be conducted for a time and under conditions suitable for preparing the identified product.

As used herein, the terms "converting" with respect to changing an intermediate or starting reagent or material in a chemical reaction refers to subjecting the intermediate or starting reagent or material to the suitable reagents and conditions (e.g., temperature, time, solvent, etc.) to effect certain changes (e.g., breaking or formation of a chemical bond) to generate the desired product.

Compound 1 can be prepared in various crystalline forms including, e.g., Form A, Form B, Form C, Form D, and Form E. In some embodiments, the solid form of Compound 1 is amorphous.

Compound 1 Form A

Provided herein is a solid form of Compound 1 which is crystalline, referred to as Form A, which is described below in the Examples. The data characterizing Form A is consistent with an anhydrous crystalline form.

In some embodiments, Form A has at least one characteristic XRPD peak selected from about 4.7, about 9.3, about 13.9, about 15.8, about 18.6, about 19.0, about 21.5, and about 27.4 degrees 2-theta. In some embodiments, Form A has at least two characteristic XRPD peaks selected from about 4.7, about 9.3, about 13.9, about 15.8, about 18.6, about 19.0, about 21.5, and about 27.4 degrees 2-theta. In some embodiments, Form A has at least three characteristic XRPD peaks selected from about 4.7, about 9.3, about 13.9, about 15.8, about 18.6, about 19.0, about 21.5, and about 27.4 degrees 2-theta. In some embodiments, Form A has at least four characteristic XRPD peaks selected from about 4.7, about 9.3, about 13.9, about 15.8, about 18.6, about 19.0, about 21.5, and about 27.4 degrees 2-theta.

In some embodiments, Form A has a characteristic XRPD peak at about 4.7 degrees 2-theta. In some embodiments, Form A has a characteristic XRPD peak at about 9.3 degrees 2-theta. In some embodiments, Form A has a characteristic XRPD peak at about 13.9 degrees 2-theta. In some embodiments, Form A has a characteristic XRPD peak at about 15.8 degrees 2-theta. In some embodiments, Form A has a characteristic XRPD peak at about 18.6 degrees 2-theta. In some embodiments, Form A has a characteristic XRPD peak at about 19.0 degrees 2-theta. In some embodiments, Form A has a characteristic XRPD peak at about 21.5 degrees 2-theta. In some embodiments, Form A has a characteristic XRPD peak at about 27.4 degrees 2-theta.

In some embodiments, Form A has an XRPD pattern with characteristic peaks as substantially shown in FIG. 1.

Figure 14:
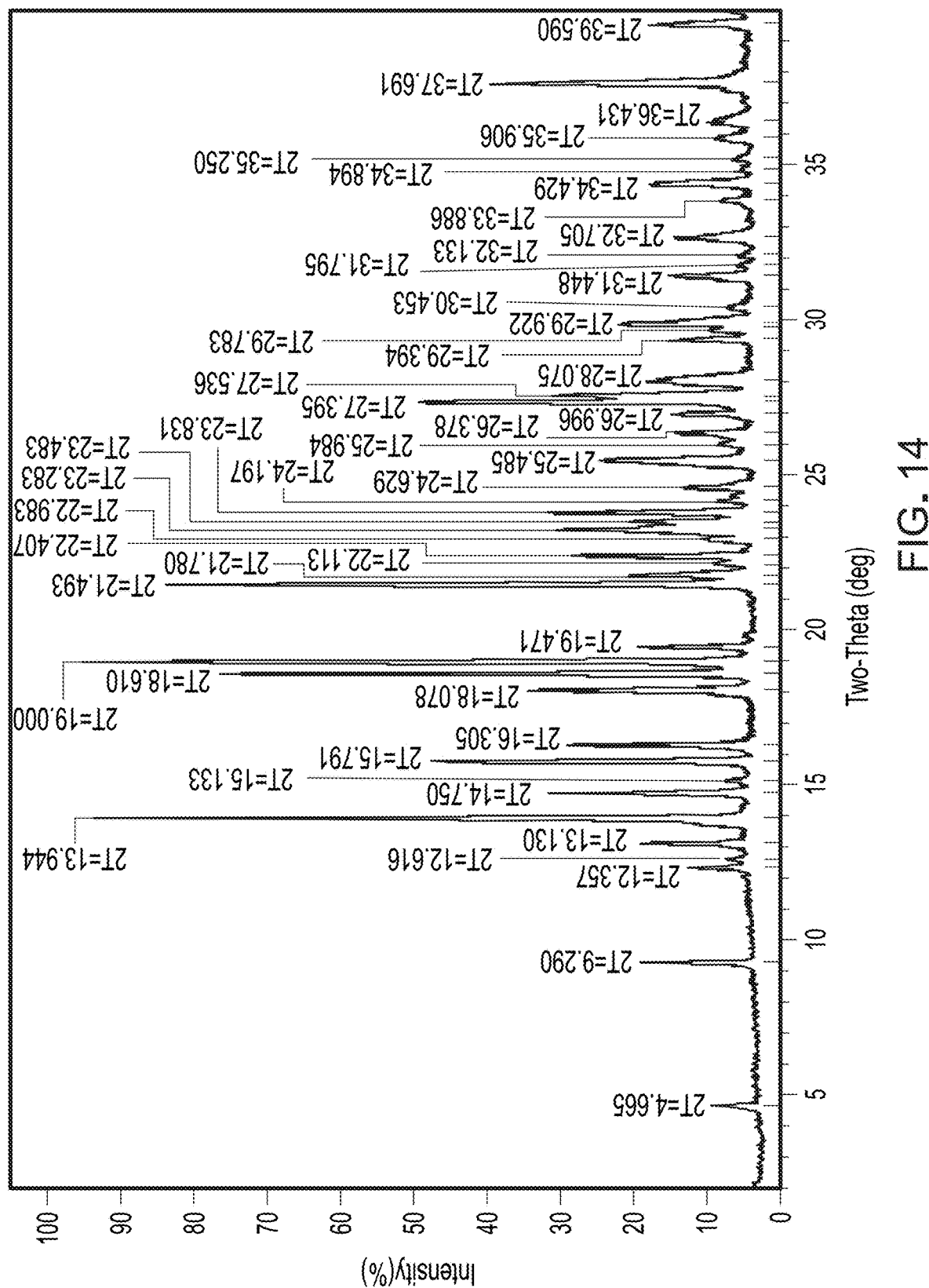
FIG. 14 shows an XRPD pattern of Compound 1, Form A, prepared from the scaled up experiment described in Example 19.

In some embodiments, Form A has an XRPD pattern with characteristic peaks as substantially shown in FIG. 14.

Figure 2:
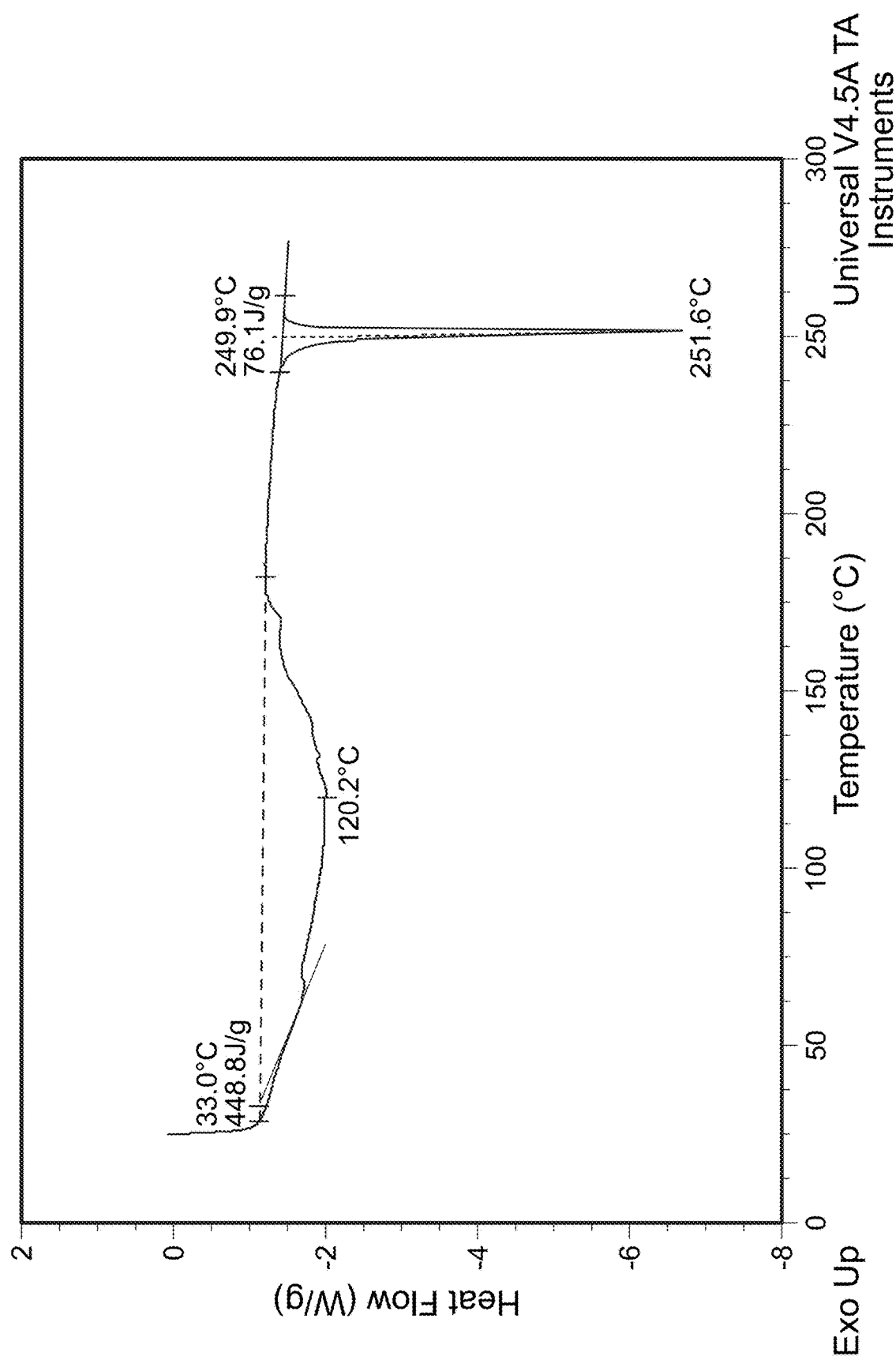
FIG. 2 shows a differential scanning calorimetry (DSC) thermogram of Compound 1, Form A.
Figure 3:
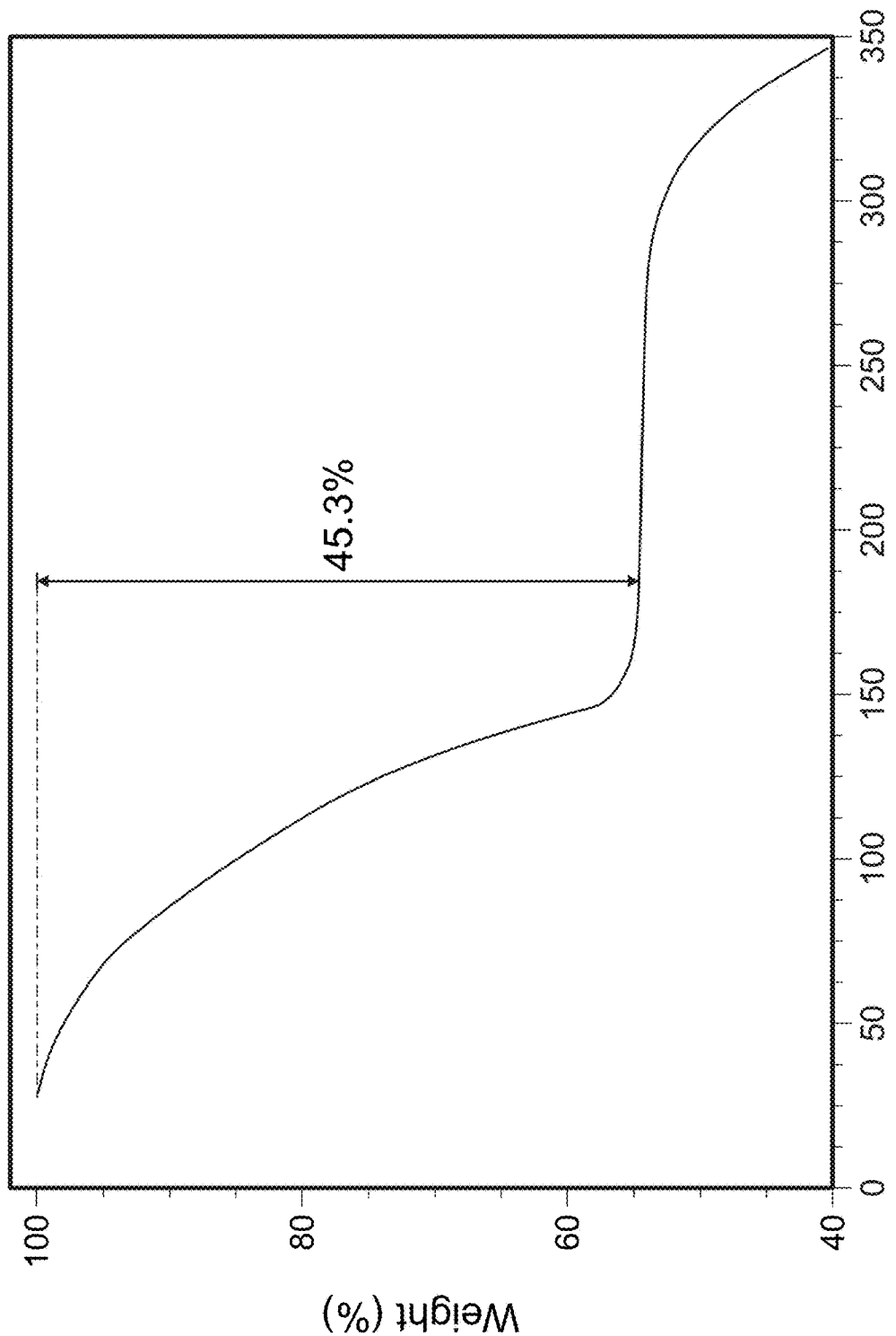
FIG. 3 shows a thermogravimetric analysis (TGA) thermogram of Compound 1, Form A.
Figure 15:
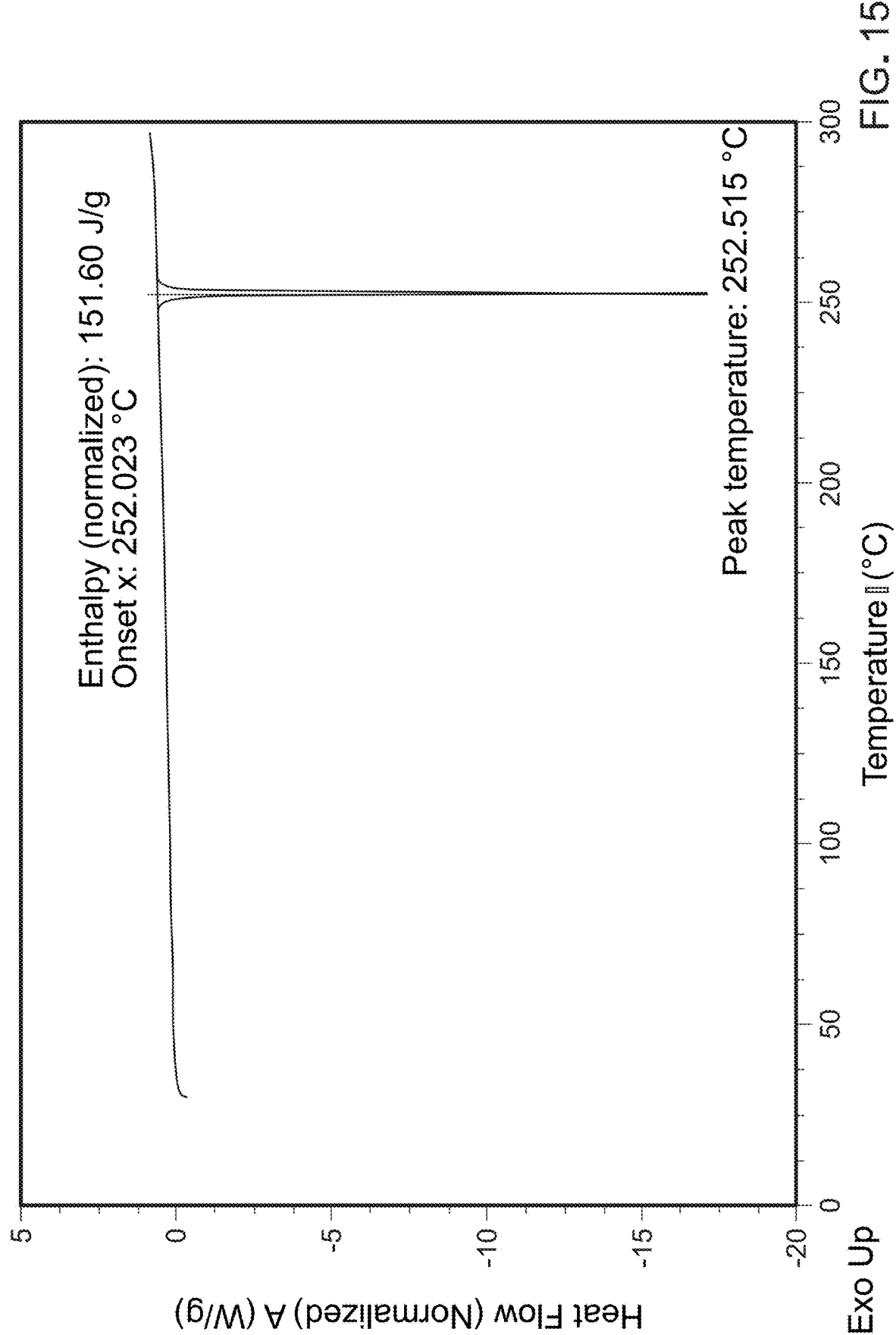
FIG. 15 shows a DSC thermogram of Compound 1, Form A, prepared from the scaled up experiment described in Example 19.
Figure 16:
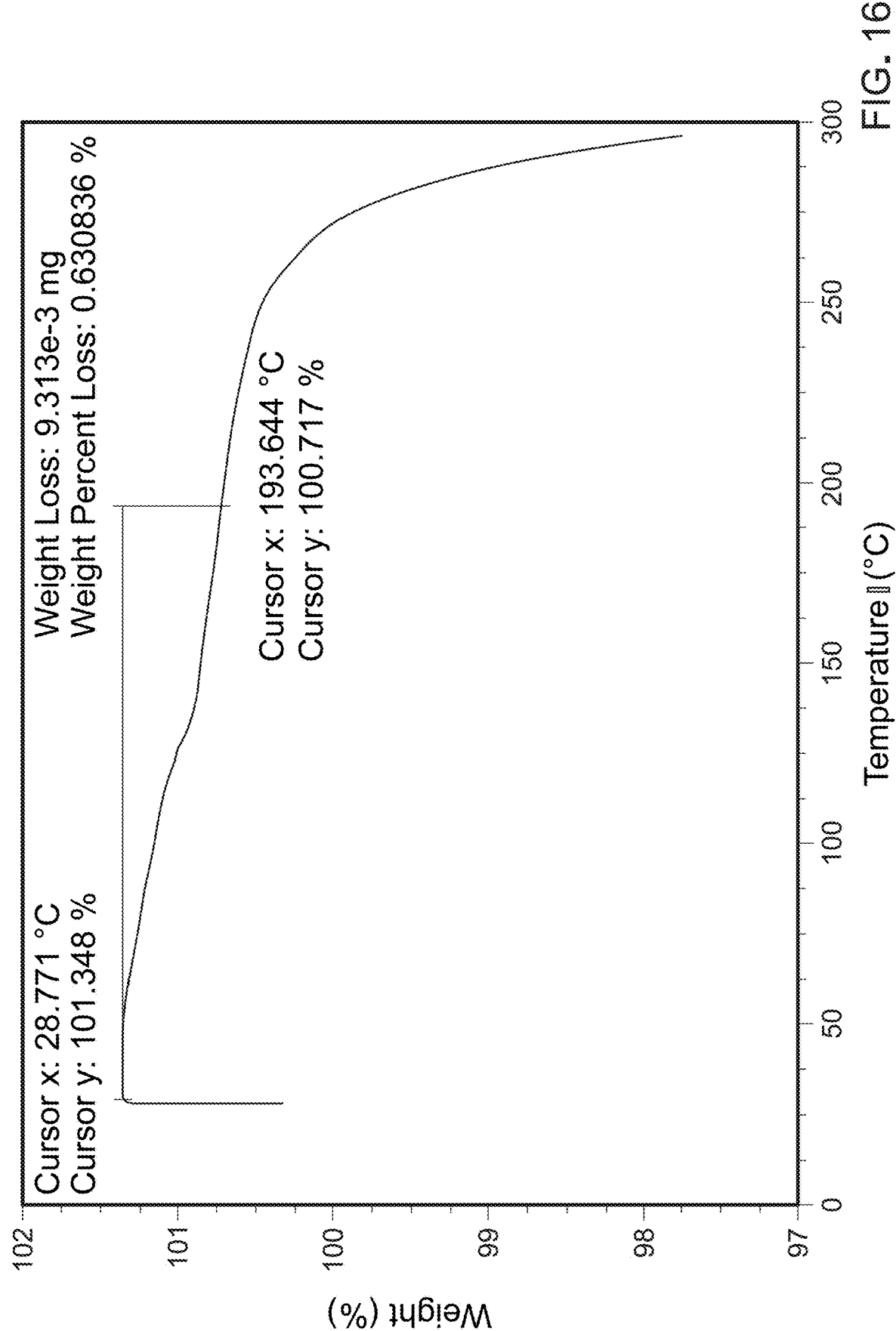
FIG. 16 shows a TGA thermogram of Compound 1, Form A, prepared from the scaled up experiment described in Example 19.
Figure 17:
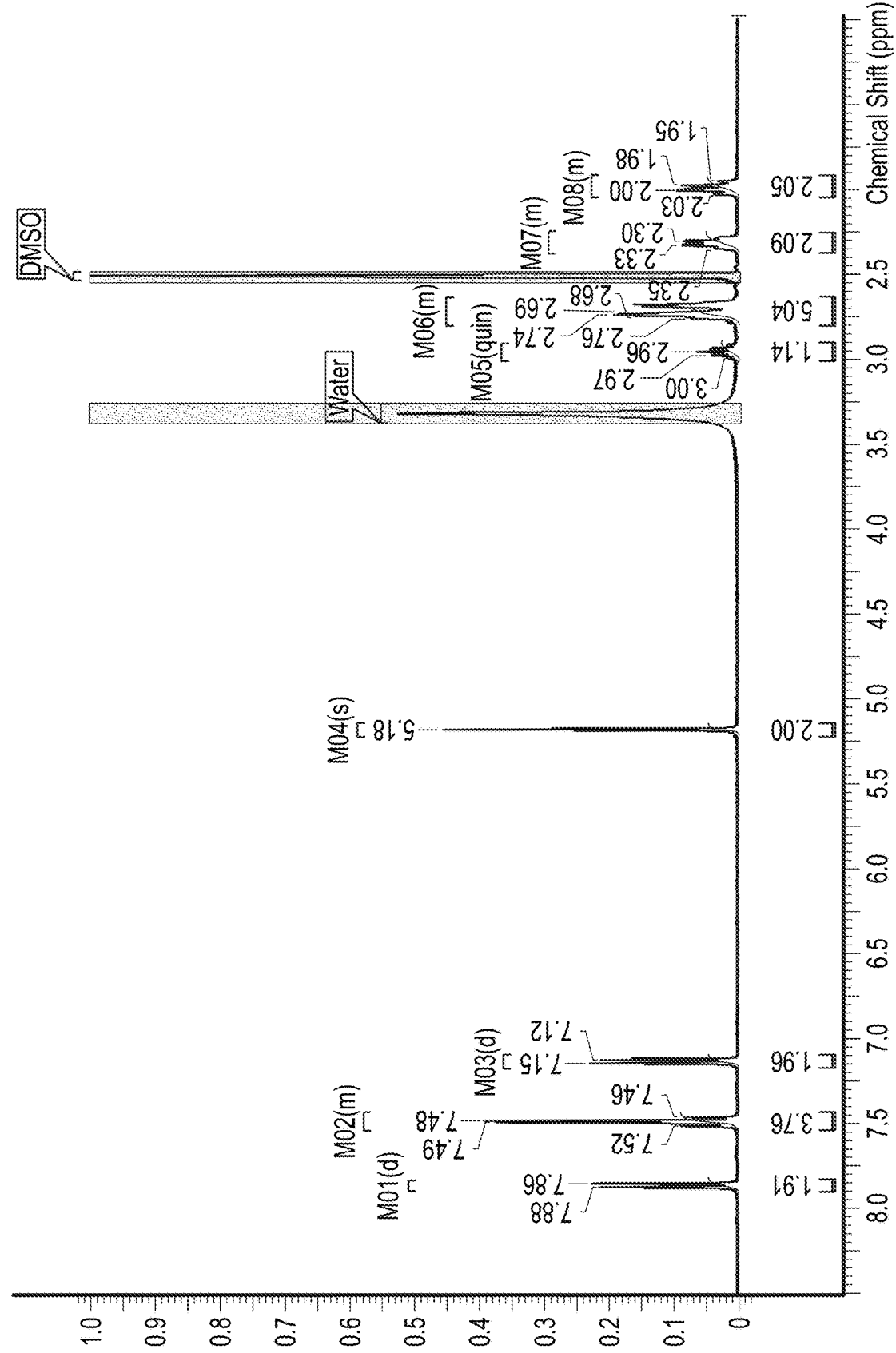
FIG. 17 shows a $^1$H-NMR spectrum of Compound 1, Form A, prepared from the scaled up experiment described in Example 19.
Figure 18:
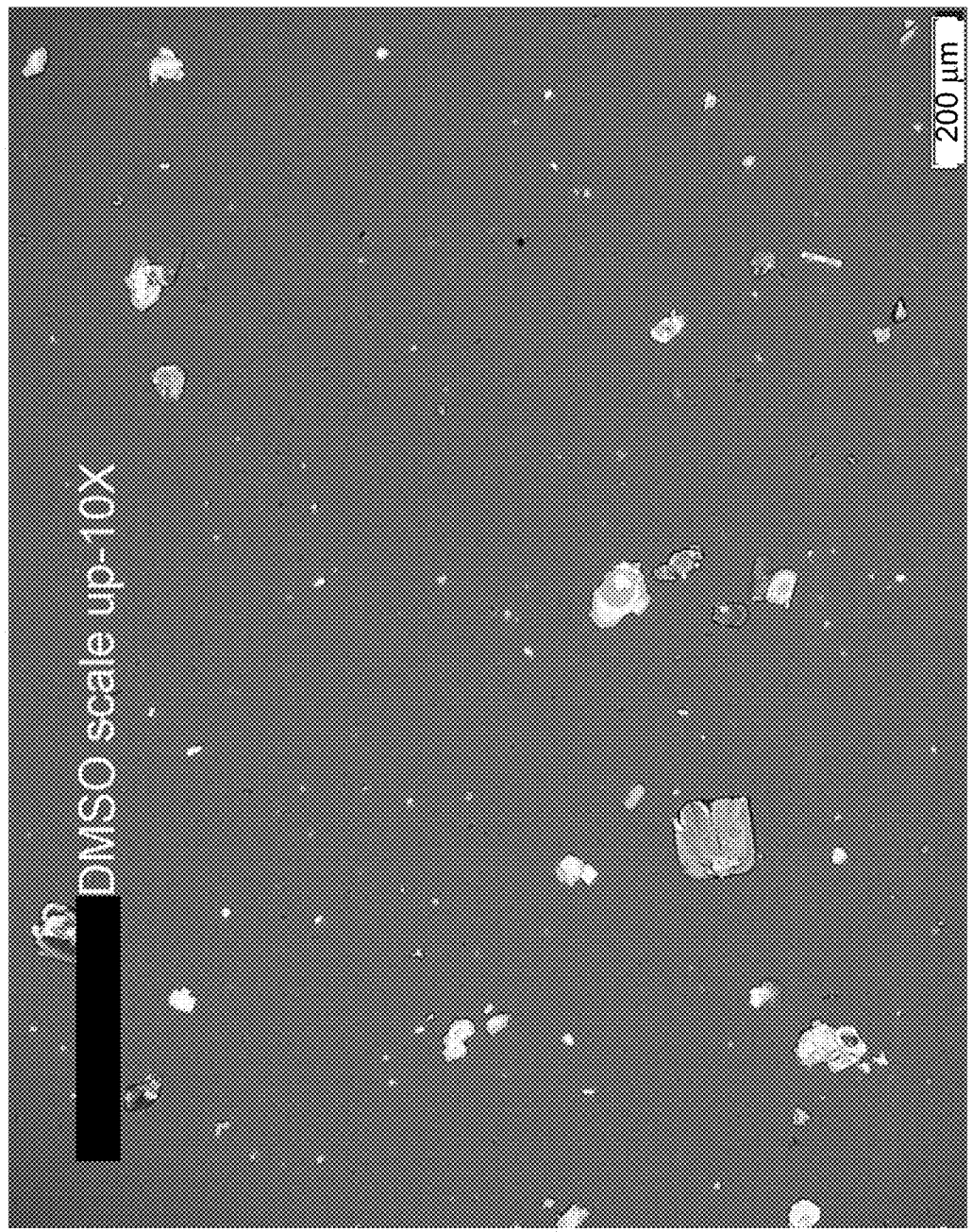
FIG. 18 shows PLM image of Compound 1, Form A, prepared from the scaled up experiment described in Example 19.

In some embodiments, Form A exhibits a DSC thermogram having endotherm peaks at temperatures of about 120° C. and about 252° C. In some embodiments, Form A exhibits a DSC thermogram having an endotherm peak at a temperature of about 120° C. In some embodiments, Form A exhibits a DSC thermogram having an endotherm peak at a temperature of about 252° C. In some embodiments, Form A has a DSC thermogram substantially as depicted in FIG. 2. In some embodiments, Form A has a DSC thermogram substantially as depicted in FIG. 15. In some embodiments, Form A has a TGA thermogram substantially as depicted in FIG. 3. In some embodiments, Form A has a TGA thermogram substantially as depicted in FIG. 16.

Provided herein are also processes for preparing Form A of Compound 1 comprising recrystallizing Compound 1 in a solvent. In some embodiments, the solvent comprises DMSO. In some embodiments, the solvent is DMSO. In some embodiments, the DMSO is substantially free of water.

In some embodiments, the recrystallizing comprises heating Compound 1 in a solvent to an elevated temperature to form a solution of Compound 1. In some embodiments, the process further comprises seeding the heated solution with Compound 1, Form A seeds, to form a seeded solution. In some embodiments, the process further comprises cooling the seeded solution to about room temperature (e.g., recrystallizing from the seeded solution). In some embodiments, the recrystallization further comprises adding an anti-solvent to the recrystallization mixture (e.g., the mixture of Compound 1 and solvent). In some embodiments, the anti-solvent is substantially free of water. In some embodiments, the anti-solvent is ethanol. In some embodiments, the anti-solvent is acetonitrile. In some embodiments, the recrystallizing comprises heating a solution of Compound 1 in a solvent (e.g., a seeded solution) to an elevated temperature for a period of time. In some embodiments, the elevated temperature is ≥60° C., ≥70° C., ≥80° C., ≥90° C., or ≥95° C. In certain embodiments, the period of time is between 1 second and 96 h. In certain embodiments, the period of time is between 1 minute and 96 h. In certain embodiments, the period of time is between 2 minutes and 96 h. In certain embodiments, the period of time is between 5 minutes and 96 h. In certain embodiments, the period of time is between 10 minutes and 96 h. In certain embodiments, the period of time is between 24 and 96 h. In certain embodiments, the period of time is between 48 and 96 h. In some embodiments, the period of time is greater than 24 h. In some embodiments, the period of time is greater than 48 h. In some embodiments, the period of time is greater than 72 h. In some embodiments, the period of time is about 72 h.

In some embodiments, the recrystallizing comprises heating Compound 1 in a solvent to form a solution of Compound 1, followed by cooling the solution. In some embodiments, the solvent is substantially free of water. In some embodiments, the solvent comprises DMSO which is substantially free of water. In some embodiments, the Compound 1 which is used to form the solution of Compound 1 is substantially free of water. In some embodiments, the heating is carried out under increased pressure (relative to ambient pressure).

In some embodiments, Form A can be isolated with a crystalline purity of at least about 80%, about 85%, about 90%, about 95%, about 96%, about 97%, about 98%, or about 99%. In some embodiments, Form A can be isolated with a crystalline purity greater than about 99%.

Compound 1 Form B

Provided herein is a solid form of Compound 1 which is crystalline, referred to as Form B, which is described below in the Examples. The data characterizing Form B is consistent with a hydrated crystalline form. In some embodiments, Form B is a monohydrate.

In some embodiments, Form B has at least one characteristic XRPD peak selected from about 8.5, about 15.1, about 23.5, and about 25.5 degrees 2-theta. In some embodiments, Form B has at least two characteristic XRPD peaks selected from about 8.5, about 15.1, about 23.5, and about 25.5 degrees 2-theta. In some embodiments, Form B has at least three characteristic XRPD peaks selected from about 8.5, about 15.1, about 23.5, and about 25.5 degrees 2-theta. In some embodiments, Form B has a characteristic XRPD peak at about 8.5 degrees 2-theta. In some embodiments, Form B has a characteristic XRPD peak at about 15.1 degrees 2-theta. In some embodiments, Form B has a characteristic XRPD peak at about 23.5 degrees 2-theta. In some embodiments, Form B has a characteristic XRPD peak at about 25.5 degrees 2-theta.

In some embodiments, Form B has at least one characteristic XRPD peak selected from about 8.5, about 15.1, about 16.5, about 21.5, about 23.5, about 24.6, and about 25.5 degrees 2-theta. In some embodiments, Form B has at least two characteristic XRPD peaks selected from about 8.5, about 15.1, about 16.5, about 21.5, about 23.5, about 24.6, and about 25.5 degrees 2-theta. In some embodiments, Form B has at least three characteristic XRPD peaks selected from about 8.5, about 15.1, about 16.5, about 21.5, about 23.5, about 24.6, and about 25.5 degrees 2-theta.

In some embodiments, Form B has at least one characteristic XRPD peak selected from about 8.5, about 15.1, about 16.1, about 16.5, about 17.0, about 18.6, about 21.3, about 21.5, about 23.5, about 24.6, about 25.2, and about 25.5 degrees 2-theta. In some embodiments, Form B has at least two characteristic XRPD peaks selected from about 8.5, about 15.1, about 16.1, about 16.5, about 17.0, about 18.6, about 21.3, about 21.5, about 23.5, about 24.6, about 25.2, and about 25.5 degrees 2-theta. In some embodiments, Form B has at least three characteristic XRPD peaks selected from about 8.5, about 15.1, about 16.1, about 16.5, about 17.0, about 18.6, about 21.3, about 21.5, about 23.5, about 24.6, about 25.2, and about 25.5 degrees 2-theta.

Figure 4:
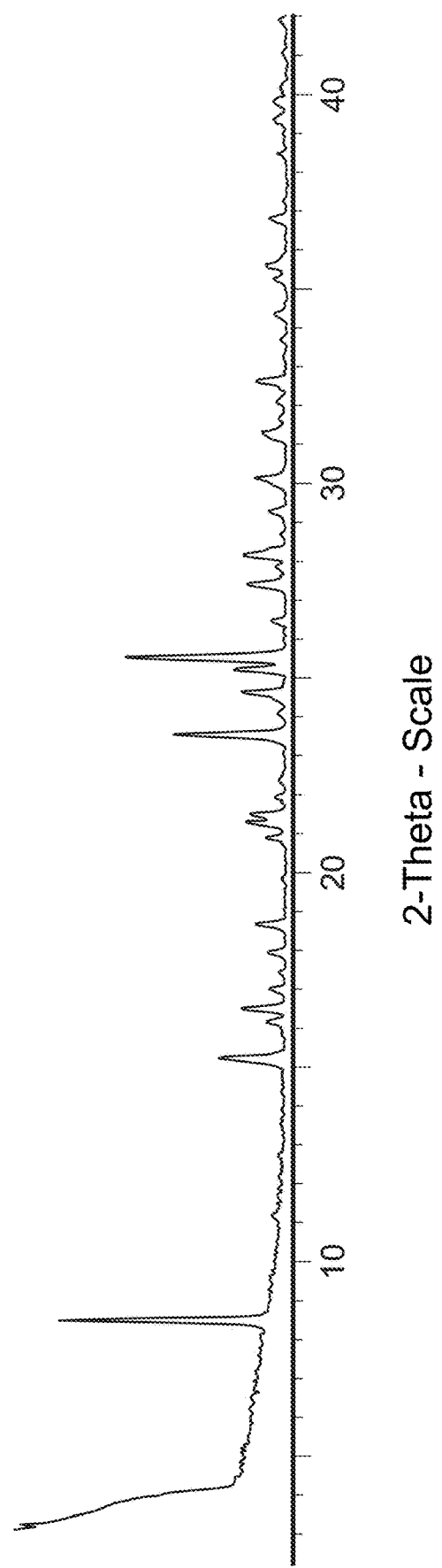
FIG. 4 shows an XRPD pattern of Compound 1, Form B.

In some embodiments, Form B has an XRPD pattern with characteristic peaks as substantially shown in FIG. 4.

Figure 5:
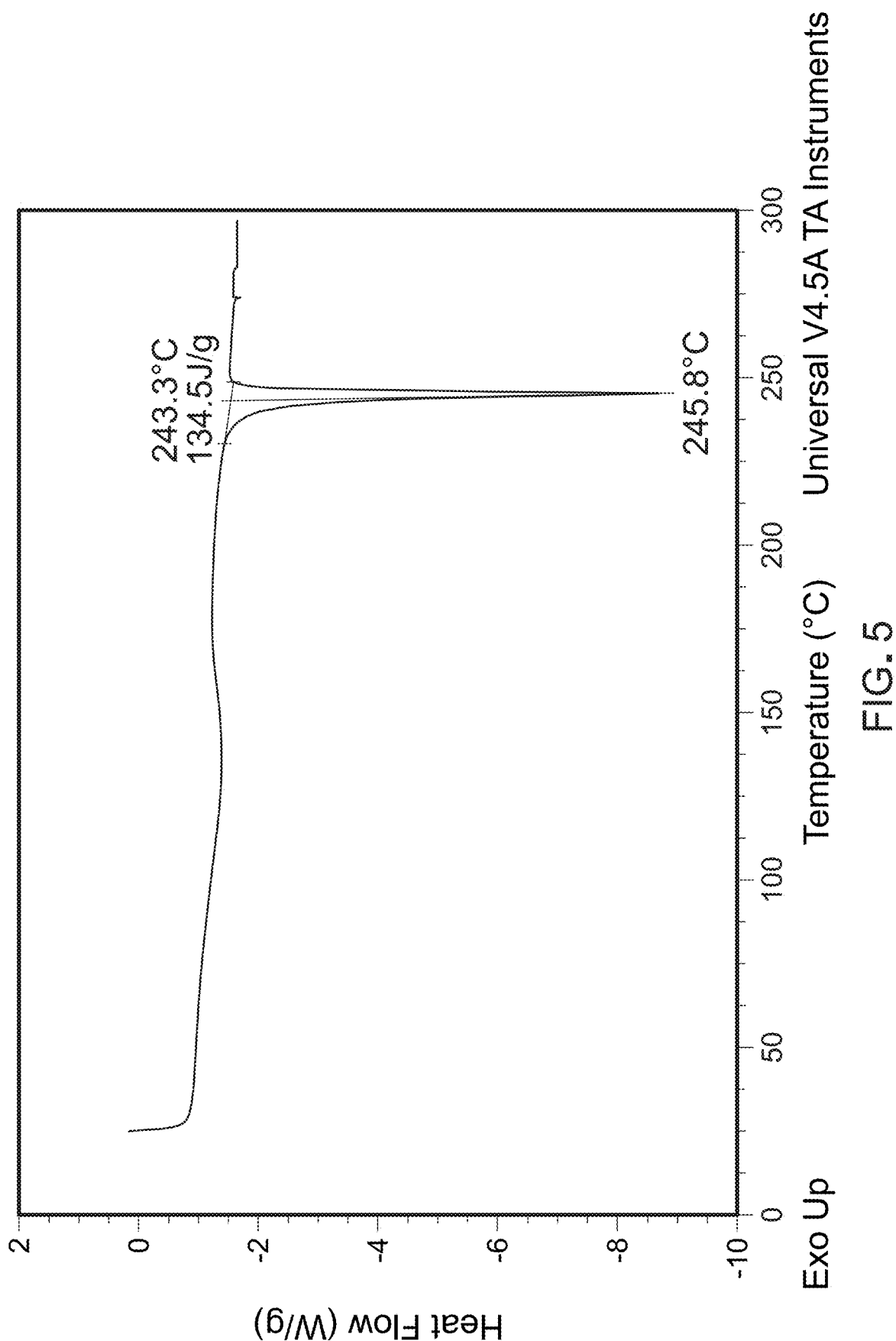
FIG. 5 shows a DSC thermogram of Compound 1, Form B.
Figure 6:
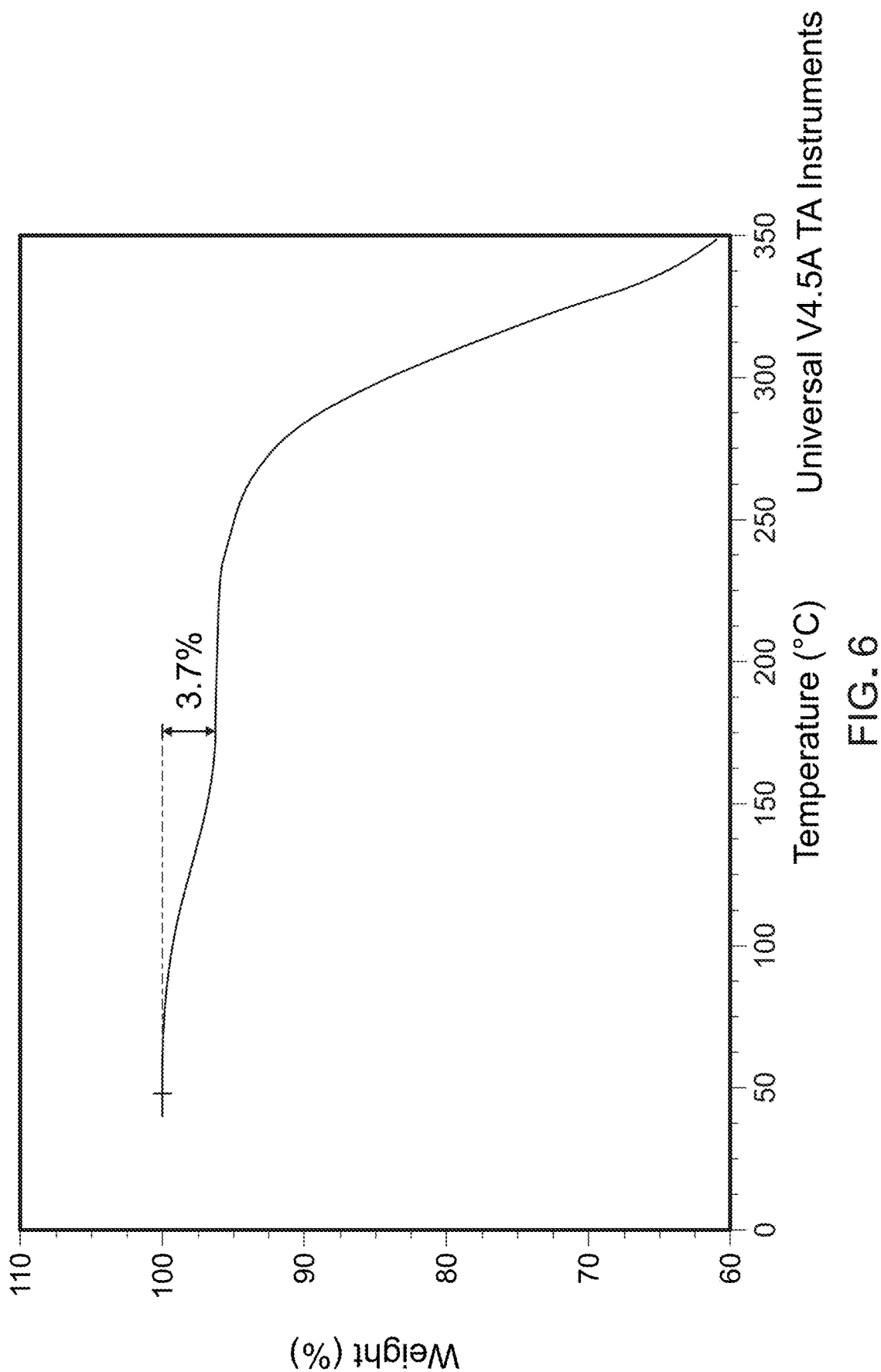
FIG. 6 shows a TGA thermogram of Compound 1, Form B.
Figure 7:
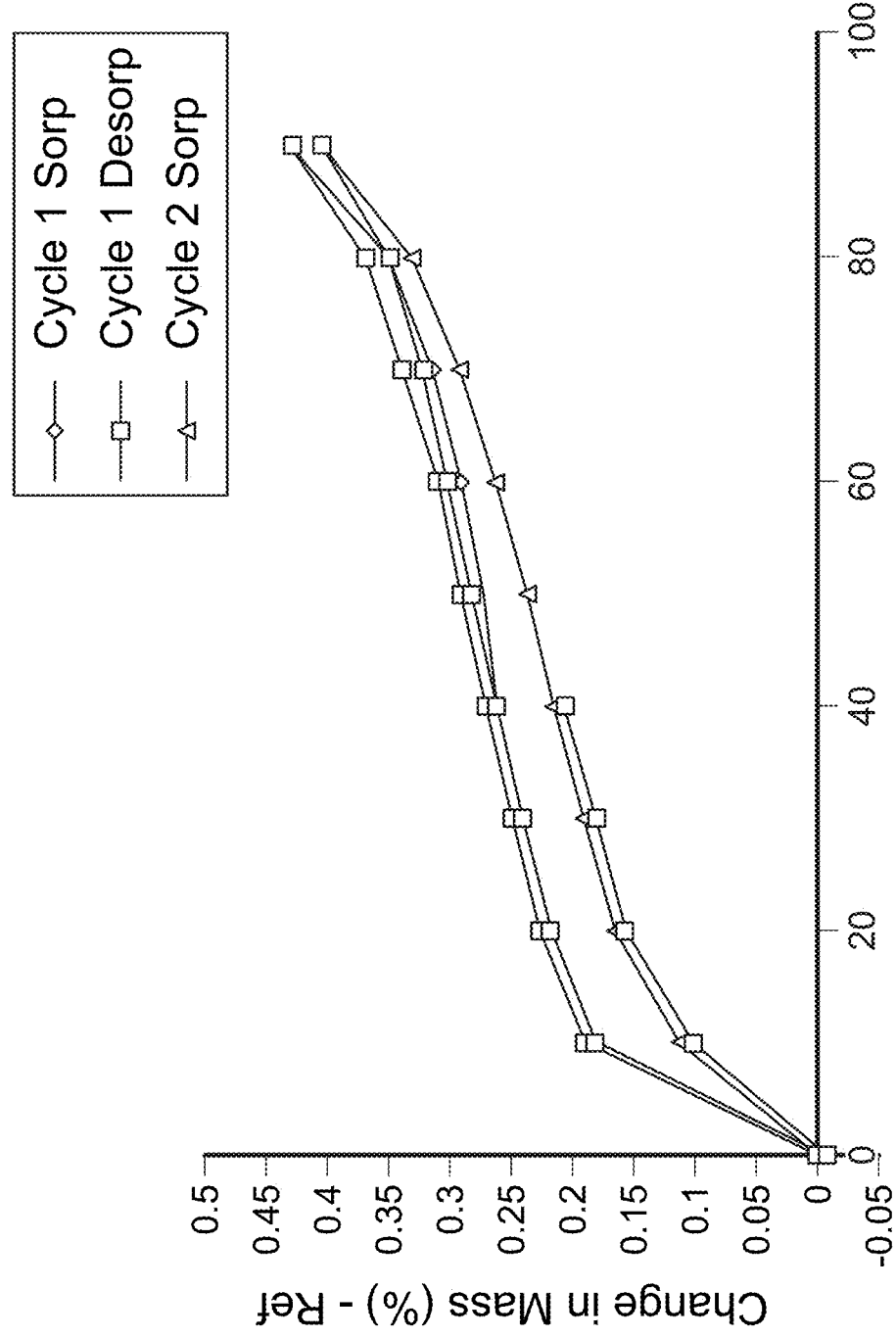
FIG. 7 shows a dynamic vapor sorption (DVS) isotherm plot of Compound 1, Form B.

In some embodiments, Form B exhibits a DSC thermogram having an endotherm peak at a temperature of about 246° C. In some embodiments, Form B has a DSC thermogram substantially as depicted in FIG. 5. In some embodiments, Form B has a TGA thermogram substantially as depicted in FIG. 6. In some embodiments, Form B has a DVS isotherm plot substantially as depicted in FIG. 7.

In some embodiments, Form B has at least one characteristic XRPD peak selected from about 8.5, about 15.1, about 23.5, and about 25.5 degrees 2-theta; and Form B exhibits a DSC thermogram having an endotherm peak at a temperature of about 246° C.

Provided herein are also processes for preparing Form B of Compound 1 comprising recrystallizing Compound 1 in a solvent. In some embodiments, the solvent comprises water. In some embodiments, the solvent comprises acetic acid. In some embodiments, the solvent comprises acetonitrile. In some embodiments, the solvent comprises DMSO. In some embodiment, the solvent comprises water and acetic acid. In some embodiments, the solvent comprises acetonitrile and acetic acid. In some embodiments, the solvent comprises DMSO and water. In some embodiments, the solvent is a mixture of water and acetic acid. In some embodiments, the solvent is a mixture of acetic acid and acetonitrile. In some embodiments, the solvent is a mixture of DMSO and water.

In some embodiments, the recrystallizing comprises a) heating a mixture of Compound 1 in a first solvent to an elevated temperature to form a first solution; b) adding a second solvent to the first solution at the elevated temperature to form a second solution; and c) cooling the second solution to a reduced temperature. In some embodiments, the elevated temperature is ≥55° C., ≥60° C., ≥65° C., ≥70° C., or ≥75° C. In some embodiments, the reduced temperature is ambient temperature. In some embodiments, the reduced temperature is about 25° C. In some embodiments, the first solvent is DMSO. In some embodiments, the second solvent is water. In some embodiments, the second solvent is acetonitrile.

In some embodiments, the recrystallizing comprises a) heating a solution of Compound 1 in a first solvent to an elevated temperature; b) adding a second solvent at the elevated temperature over a first period of time; and c) cooling to a reduced temperature for a second period of time. In some embodiments, the elevated temperature is ≥55° C., ≥60° C., ≥65° C., ≥70° C., or ≥75° C. In certain embodiments, the first period of time is between 1 and 5 h. In some embodiments, the first period of time is about 2 h. In some embodiments, the reduced temperature is ambient temperature. In some embodiments, the reduced temperature is about 25° C. In some embodiments, the second period of time is between 6 and 18 hours. In some embodiments, the second period of time is about 12 h. In some embodiments, the first solvent is acetic acid. In some embodiments, the first solvent is DMSO. In some embodiments, the second solvent is water. In some embodiments, the second solvent is acetonitrile.

In some embodiments, Form B can be isolated with a crystalline purity of at least about 80%, about 85%, about 90%, about 95%, about 96%, about 97%, about 98%, or about 99%. In some embodiments, Form B can be isolated with a crystalline purity greater than about 99%.

Compound 1 Form C

Provided herein is a solid form of Compound 1 which is crystalline, referred to as Form C, which is described below in the Examples. The data characterizing Form C is consistent with an anhydrous crystalline form.

In some embodiments, Form C has at least one characteristic XRPD peak selected from about 7.4, about 22.2, about 25.0, about 25.4, and about 28.2 degrees 2-theta. In some embodiments, Form C has at least two characteristic XRPD peaks selected from about 7.4, about 22.2, about 25.0, about 25.4, and about 28.2 degrees 2-theta. In some embodiments, Form C has at least three characteristic XRPD peaks selected from about 7.4, about 22.2, about 25.0, about 25.4, and about 28.2 degrees 2-theta. In some embodiments, Form C has a characteristic XRPD peak at about 7.4 degrees 2-theta. In some embodiments, Form C has a characteristic XRPD peak at about 22.2 degrees 2-theta. In some embodiments, Form C has a characteristic XRPD peak at about 25.0 degrees 2-theta. In some embodiments, Form C has a characteristic XRPD peak at about 25.4 degrees 2-theta. In some embodiments, Form C has a characteristic XRPD peak at about 28.2 degrees 2-theta.

In some embodiments, Form C has at least one characteristic XRPD peak selected from about 7.4, about 11.0, about 22.2, about 25.0, about 25.4, about 28.2, and about 29.8 degrees 2-theta. In some embodiments, Form C has at least two characteristic XRPD peaks selected from about 7.4, about 11.0, about 22.2, about 25.0, about 25.4, about 28.2, and about 29.8 degrees 2-theta. In some embodiments, Form C has at least three characteristic XRPD peaks selected from about 7.4, about 11.0, about 22.2, about 25.0, about 25.4, about 28.2, and about 29.8 degrees 2-theta.

In some embodiments, Form C has at least one characteristic XRPD peak selected from about 7.4, about 11.0, about 15.6, about 16.5, about 17.3, about 18.5, about 22.2, about 25.0, about 25.4, about 28.2, and about 29.8 degrees 2-theta. In some embodiments, Form C has at least two characteristic XRPD peaks selected from about 7.4, about 11.0, about 15.6, about 16.5, about 17.3, about 18.5, about 22.2, about 25.0, about 25.4, about 28.2, and about 29.8 degrees 2-theta. In some embodiments, Form C has at least three characteristic XRPD peaks selected from about 7.4, about 11.0, about 15.6, about 16.5, about 17.3, about 18.5, about 22.2, about 25.0, about 25.4, about 28.2, and about 29.8 degrees 2-theta.

Figure 8:
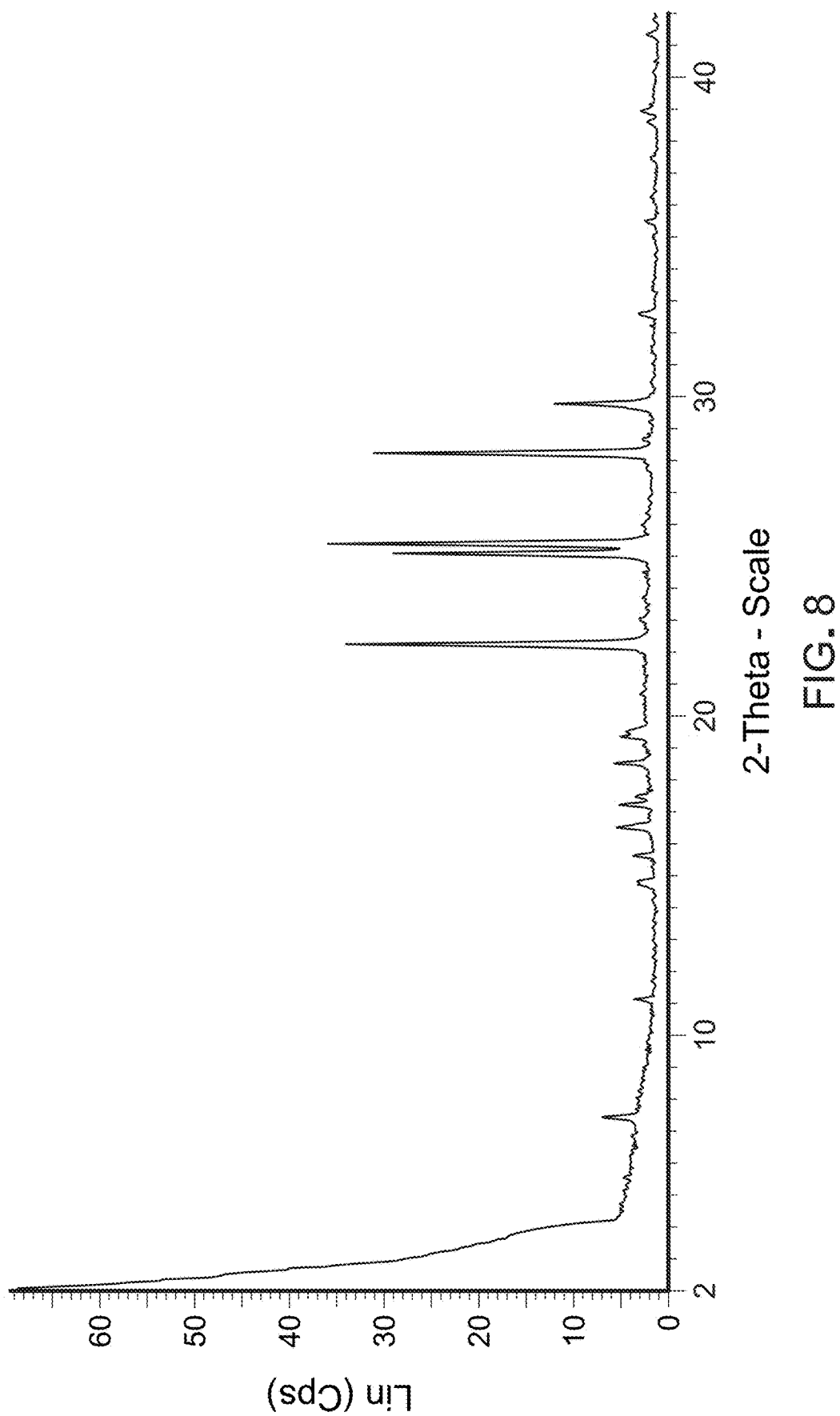
FIG. 8 shows an XRPD pattern of Compound 1, Form C.

In some embodiments, Form C has an XRPD pattern with characteristic peaks as substantially shown in FIG. 8.

Figure 9:
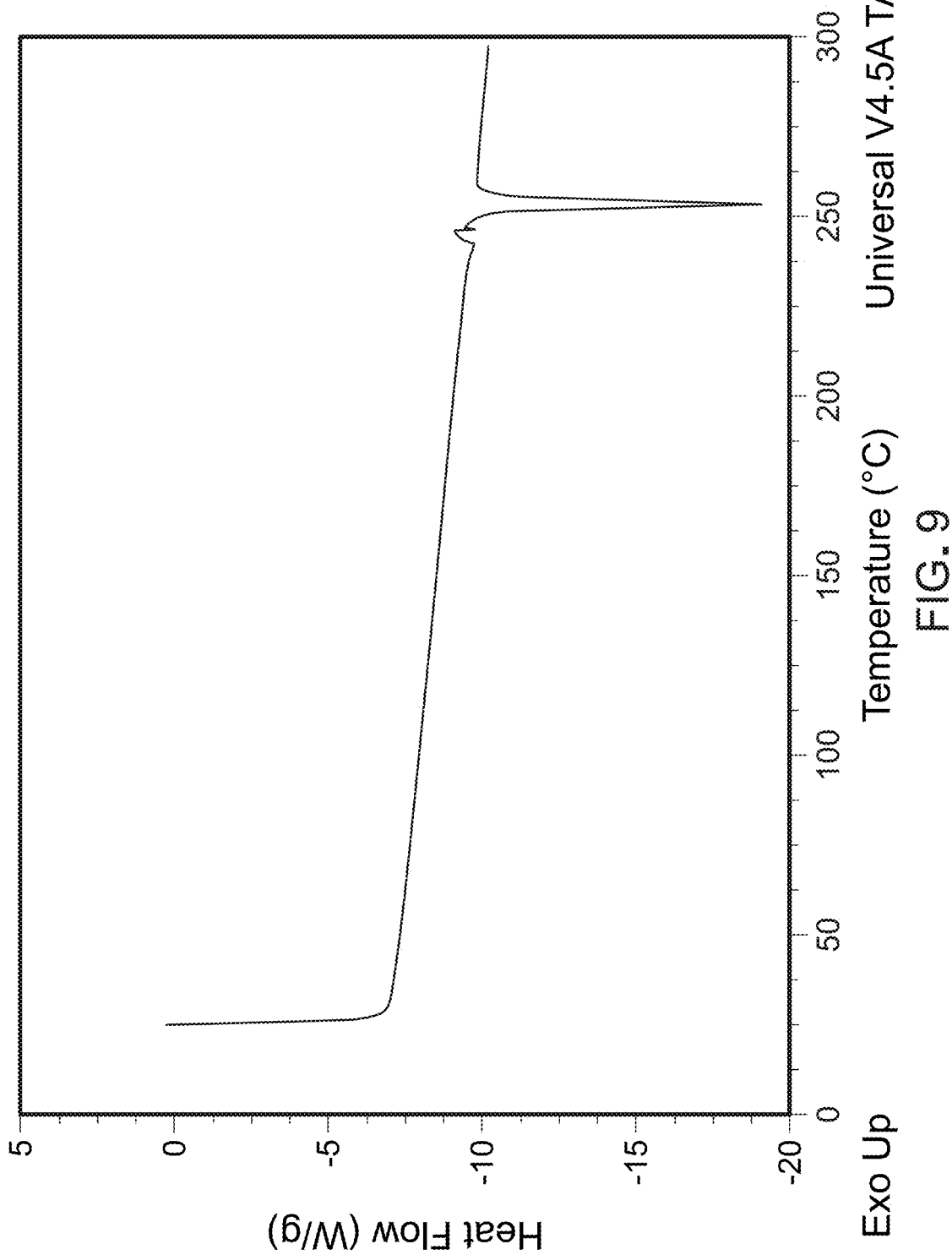
FIG. 9 shows a DSC thermogram of Compound 1, Form C.
Figure 10:
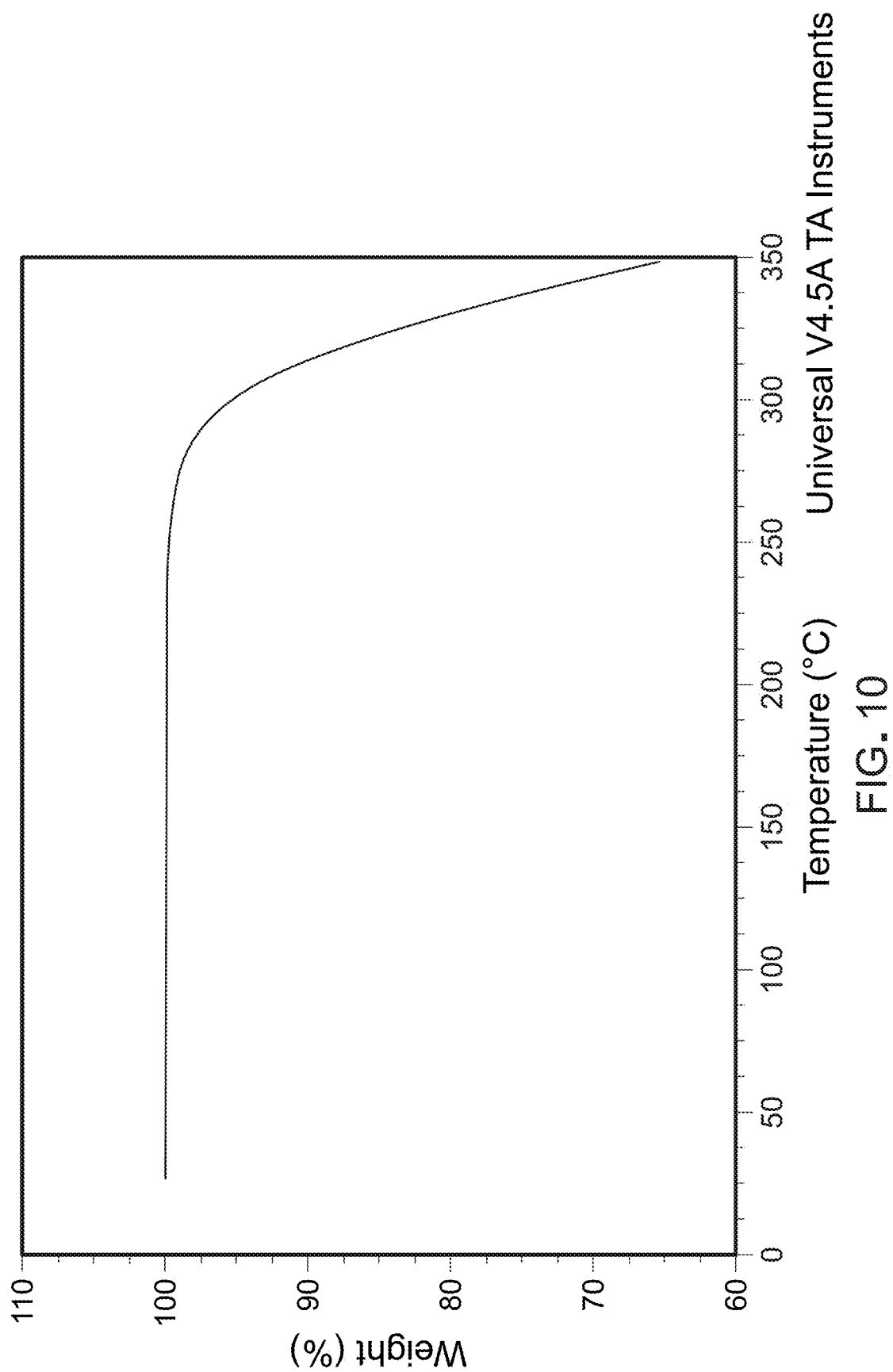
FIG. 10 shows a TGA thermogram of Compound 1, Form C.

In some embodiments, Form C exhibits a DSC thermogram having an exotherm peak at a temperature of about 242° C. and an endotherm peak at a temperatures of about 253° C. In some embodiments, Form C exhibits a DSC thermogram having an exotherm peak at a temperature of about 242° C. In some embodiments, Form C exhibits a DSC thermogram having an endotherm peak at a temperature of about 253° C. In some embodiments, Form C has a DSC thermogram substantially as depicted in FIG. 9. In some embodiments, Form C has a TGA thermogram substantially as depicted in FIG. 10.

In some embodiments, Form C has at least one characteristic XRPD peak selected from about 7.4, about 22.2, about 25.0, about 25.4, and about 28.2 degrees 2-theta; and Form C exhibits a DSC thermogram having an endotherm peak at a temperature of about 246° C. In some embodiments, Form C has at least one characteristic XRPD peak selected from about 7.4, about 22.2, about 25.0, about 25.4, and about 28.2 degrees 2-theta; and Form C exhibits a DSC thermogram having an exotherm peak at a temperature of about 242° C.

Provided herein are also processes for preparing Form C of Compound 1 comprising recrystallizing Compound 1 in a solvent. In some embodiments, the solvent comprises water. In some embodiments, the solvent comprises DMSO. In some embodiments, the solvent comprises DMSO and water. In some embodiments, the solvent is DMSO. In some embodiments, the solvent is a mixture of DMSO and water.

In some embodiments, the recrystallizing comprises a) heating a mixture of Compound 1 in a first solvent to an elevated temperature to form a first solution; b) adding a second solvent to the first solution to form a second solution; and c) cooling the second solution to a reduced temperature. In some embodiments, the first solvent is DMSO. In some embodiments, the second solvent is water. In some embodiments, the elevated temperature is ≥65° C., ≥70° C., ≥75° C., ≥80° C., or ≥85° C. In some embodiments, the reduced temperature is ambient temperature. In some embodiments, the reduced temperature is about 25° C.

In some embodiments, the recrystallizing comprises a) heating a solution of Compound 1 in a first solvent to an elevated temperature; b) adding a second solvent to the solution; and c) cooling to a reduced temperature for a period of time. In some embodiments, the first solvent is DMSO. In some embodiments, the second solvent is water. In some embodiments, the elevated temperature is ≥65° C., ≥70° C., ≥75° C., ≥80° C., or ≥85° C. In certain embodiments, the period of time is between 2 and 12 h. In some embodiments, the first period of time is about 8 h. In some embodiments, the first period of time is greater than about 6 h. In some embodiments, the reduced temperature is ambient temperature. In some embodiments, the reduced temperature is about 25° C.

In some embodiments, Form C can be isolated with a crystalline purity of at least about 80%, about 85%, about 90%, about 95%, about 96%, about 97%, about 98%, or about 99%. In some embodiments, Form C can be isolated with a crystalline purity greater than about 99%.

Compound 1 Form D

Provided herein is a solid form of Compound 1 which is crystalline, referred to as Form D, which is described below in the Examples. The data characterizing Form D is consistent with a dimethylacetamide solvated crystalline form.

Figure 11:
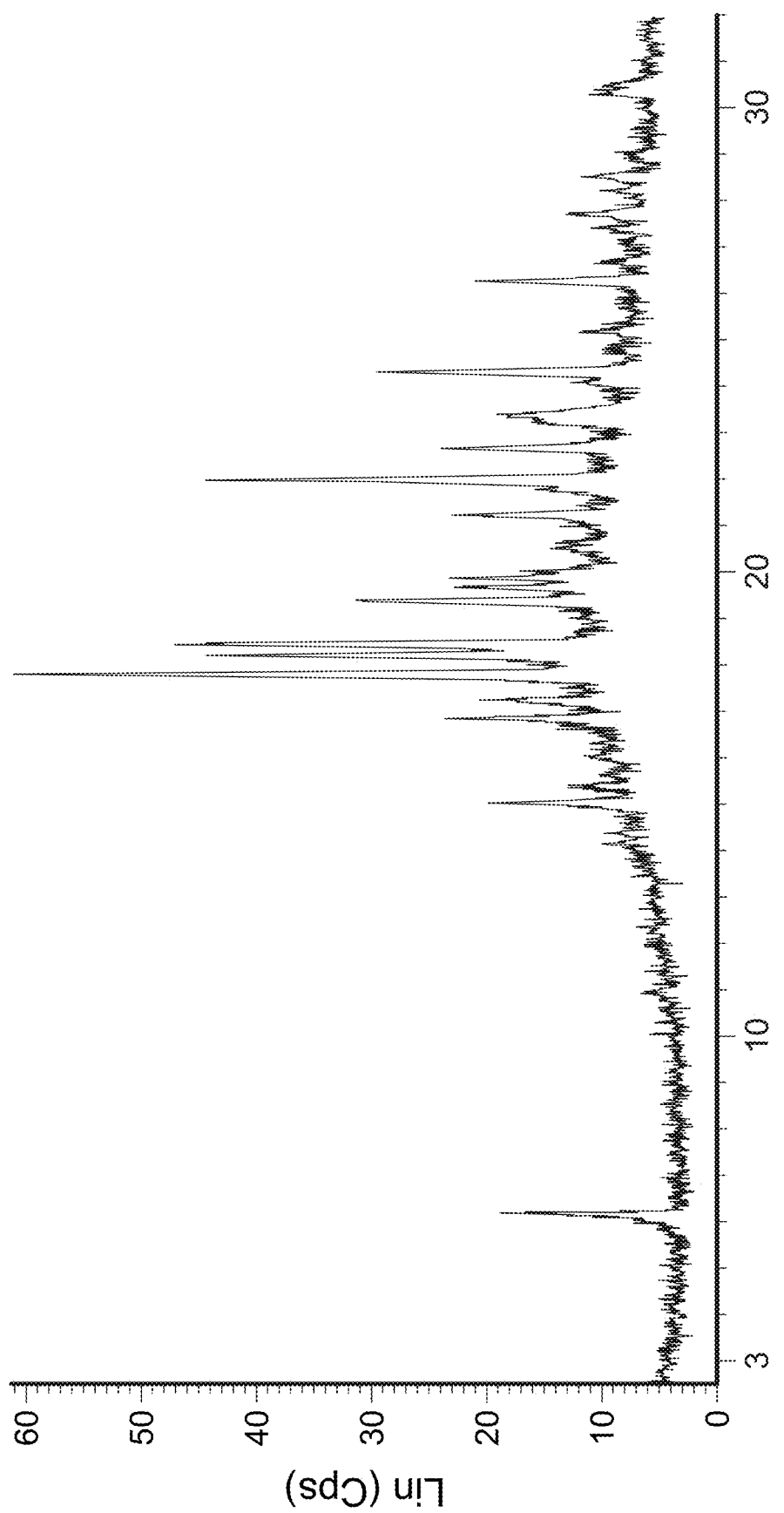
FIG. 11 shows an XRPD pattern of Compound 1, Form D.

In some embodiments, Form D has an XRPD pattern with characteristic peaks as substantially shown in FIG. 11.

Provided herein are also processes for preparing Form D of Compound 1 comprising recrystallizing Compound 1 in a solvent. In some embodiments, the solvent comprises dimethylacetamide. In some embodiments, the solvent is dimethylacetamide. In some embodiments, the recrystallizing comprises a) heating a solution of Compound 1 in dimethylacetamide to an elevated temperature and b) cooling to a reduced temperature. In some embodiments, the elevated temperature is ≥30° C., ≥40° C., ≥50° C., ≥60° C., ≥70° C., ≥80° C., or ≥90° C. In some embodiments, the reduced temperature is ambient temperature. In some embodiments, the reduced temperature is about 25° C.

In some embodiments, Form D can be isolated with a crystalline purity of at least about 80%, about 85%, about 90%, about 95%, about 96%, about 97%, about 98%, or about 99%. In some embodiments, Form D can be isolated with a crystalline purity greater than about 99%.

Compound 1 Form E

Provided herein is a solid form of Compound 1 which is crystalline, referred to as Form E, which is described below in the Examples. The data characterizing Form E is consistent with an anhydrous crystalline form.

In some embodiments, Form E has at least one characteristic XRPD peak selected from about 8.7, about 15.3, about 16.2, about 23.2, and about 25.5 degrees 2-theta. In some embodiments, Form E has at least two characteristic XRPD peaks selected from about 8.7, about 15.3, about 16.2, about 23.2, and about 25.5 degrees 2-theta. In some embodiments, Form E has at least three characteristic XRPD peaks selected from about 8.7, about 15.3, about 16.2, about 23.2, and about 25.5 degrees 2-theta. In some embodiments, Form E has a characteristic XRPD peak at about 8.7 degrees 2-theta. In some embodiments, Form E has a characteristic XRPD peak at about 15.3 degrees 2-theta. In some embodiments, Form E has a characteristic XRPD peak at about 16.2 degrees 2-theta. In some embodiments, Form E has a characteristic XRPD peak at about 23.2 degrees 2-theta. In some embodiments, Form E has a characteristic XRPD peak at about 25.5 degrees 2-theta.

In some embodiments, Form E has at least one characteristic XRPD peak selected from about 8.7, about 15.3, about 16.2, about 18.3, about 23.2, about 25.5, and about 28.2 degrees 2-theta. In some embodiments, Form E has at least two characteristic XRPD peaks selected from about 8.7, about 15.3, about 16.2, about 18.3, about 23.2, about 25.5, and about 28.2 degrees 2-theta. In some embodiments, Form E has at least three characteristic XRPD peaks selected from about 8.7, about 15.3, about 16.2, about 18.3, about 23.2, about 25.5, and about 28.2 degrees 2-theta.

In some embodiments, Form E has at least one characteristic XRPD peak selected from about 8.7, about 10.8, about 15.3, about 16.2, about 16.9, about 18.3, about 21.9, about 23.2, about 25.5, and about 28.2 degrees 2-theta. In some embodiments, Form E has at least two characteristic XRPD peaks selected from about 8.7, about 10.8, about 15.3, about 16.2, about 16.9, about 18.3, about 21.9, about 23.2, about 25.5, and about 28.2 degrees 2-theta. In some embodiments, Form E has at least three characteristic XRPD peaks selected from about 8.7, about 10.8, about 15.3, about 16.2, about 16.9, about 18.3, about 21.9, about 23.2, about 25.5, and about 28.2 degrees 2-theta.

Figure 12:
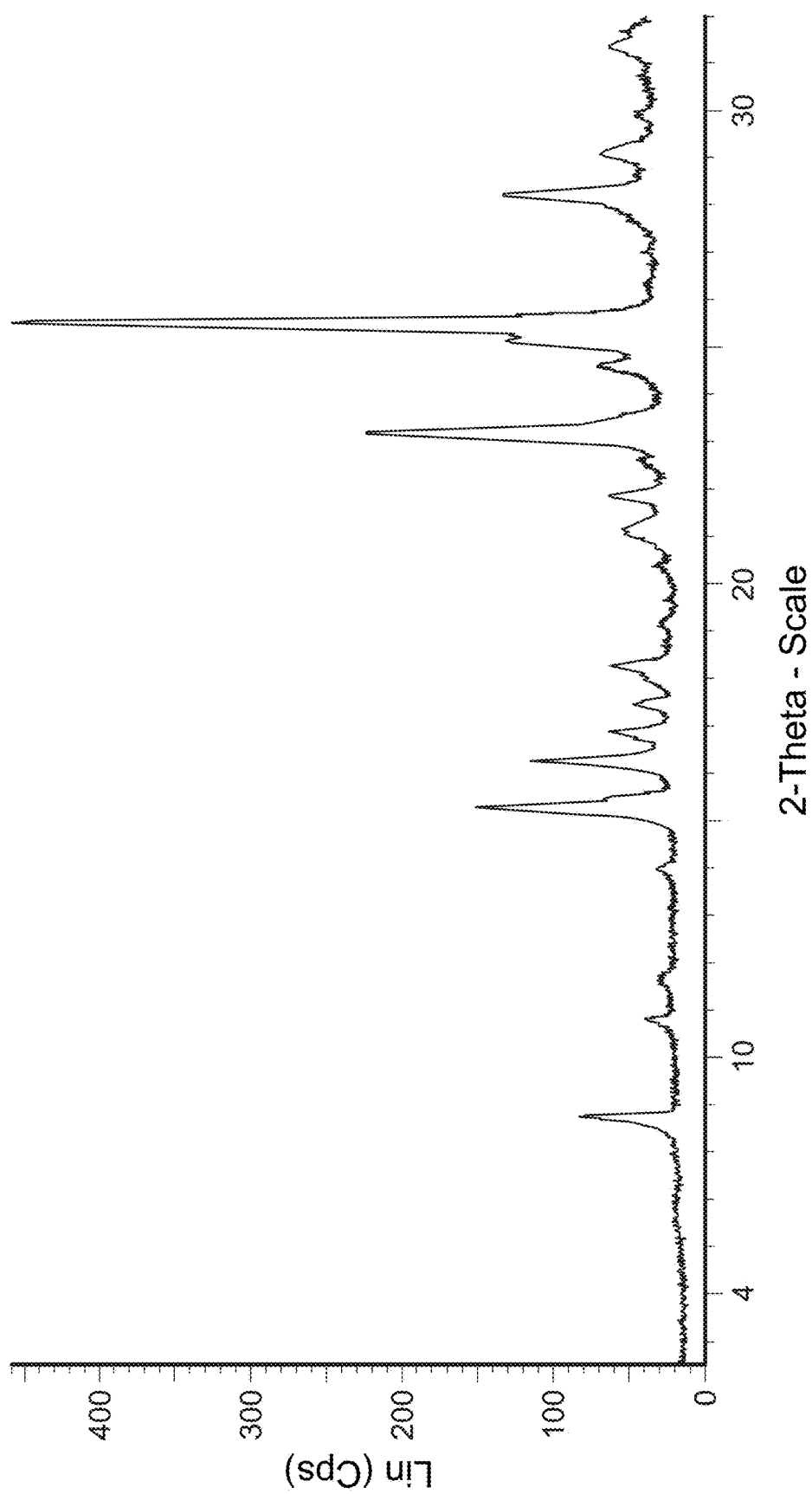
FIG. 12 shows an XRPD pattern of Compound 1, Form E.

In some embodiments, Form E has an XRPD pattern with characteristic peaks as substantially shown in FIG. 12.

Provided herein are also processes for preparing Form E of Compound 1 comprising heating Compound 1 Form B to an elevated temperature. In some embodiments, the elevated temperature is ≥100° C., ≥125° C., ≥145° C., ≥150° C., or ≥155° C. In some embodiments, the elevated temperature is about 150° C.

In some embodiments, Form E can be isolated with a crystalline purity of at least about 80%, about 85%, about 90%, about 95%, about 96%, about 97%, about 98%, or about 99%. In some embodiments, Form E can be isolated with a crystalline purity greater than about 99%.

Methods of Use

Compound 1 and solid forms thereof exhibit affinity for S1P receptors. In particular, compounds of the invention show selective affinity for the S1P5 receptor over the S1P1 and/or S1P3 receptor(s).

Compound 1 and solid forms thereof are modulators of the S1P receptor, in particular of the S1P5 receptor. More specifically, the compounds and solid forms of the invention are S1P5 receptor agonists. The compounds and solid forms of the invention are useful for treating, alleviating and preventing diseases associated with S1P receptors (e.g., S1P5) or in which modulation of the endogenous S1P signaling system via any S1P receptor is involved. In particular, the compounds and solid forms of the present invention may be used to treat, alleviate or prevent CNS (central nervous system) disorders, such as neurodegenerative disorders, in particular, but not limited to, cognitive disorders (in particular age-related cognitive decline) and related conditions such as, e.g., Alzheimer's disease, (vascular) dementia, Nieman's Pick disease, and cognitive deficits in schizophrenia, obsessive-compulsive behavior, major depression, autism, multiple sclerosis and pain. Preferably, the compounds and solid forms of the present invention may be used to treat, alleviate or prevent cognitive disorders (in particular age-related cognitive decline) and related conditions.

As used herein, the term "contacting" refers to the bringing together of the indicated moieties in an in vitro system or an in vivo system such that they are in sufficient physical proximity to interact.

The terms "individual" or "patient," used interchangeably, refer to any animal, including mammals, such as humans, mice, rats, other rodents, rabbits, dogs, cats, swine, cattle, sheep, horses, and primates. In some embodiments, the individual or patient is a human.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy*, 21*st ed.*; Lippincott Williams & Wilkins: Philadelphia, Pa., 2005; *Handbook of Pharmaceutical Excipients*, 6*th ed.*; Rowe et al., Eds.; The Pharmaceutical Press and the American Pharmaceutical Association: 2009; *Handbook of Pharmaceutical Additives*, 3*rd ed.*; Ash and Ash Eds.; Gower Publishing Company: 2007; *Pharmaceutical Preformulation and Formulation*, 2*nd ed.*; Gibson Ed.; CRC Press LLC: Boca Raton, Fla., 2009.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapy

One or more additional pharmaceutical agents or treatment methods can be used in combination with Compound 1 or a solid form thereof for treatment of S1P receptor-associated diseases, disorders, or conditions, or diseases or conditions as described herein. The agents can be combined with the present compounds in a single dosage form, or the agents can be administered simultaneously or sequentially as separate dosage forms. In some embodiments, the additional pharmaceutical agent is an anti-Alzheimer's drug. In some embodiments, the additional pharmaceutical agent is an anti-vascular dementia drug. In some embodiments, the additional pharmaceutical agent is a cholinesterase inhibitor (e.g., donepezil, galantamine, and rivastigmine), N-methyl-D-aspartate receptor antagonist, memantine, nimodipine, hydergine, nicergoline, CDP-choline, or folic acid.

In some embodiments, the additional pharmaceutical agent is an anti-psychotic. In some embodiments, the additional pharmaceutical agent is chlorpromazine, fluphenazine, haloperidol, perphenazine, aripiprazole, asenapine, brexpiprazole, cariprazine, clozapine, lloperidone, lurasidone, olanzapine, paliperidone, quetiapine, risperidone, or ziprasidone.

Pharmaceutical Formulations and Dosage Forms

When employed as pharmaceuticals, the compounds and solid forms of the present disclosure can be administered in the form of pharmaceutical compositions. Thus the present disclosure provides a composition comprising a compound or solid form as described herein, a compound or solid form as recited in any of the claims and described herein, or any of the embodiments thereof, and at least one pharmaceutically acceptable carrier. These compositions can be prepared in a manner well known in the pharmaceutical arts, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound or solid form of the present disclosure or a pharmaceutically acceptable salt thereof, in combination with one or more pharmaceutically acceptable carriers. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In some embodiments, the composition is a sustained release composition comprising at least one compound or solid form described herein, or a pharmaceutically acceptable salt thereof, and at least one pharmaceutically acceptable carrier or excipient.

The compositions can be formulated in a unit dosage form, each dosage containing from about 5 to about 1,000 mg (1 g). The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a therapeutically effective amount. It will be understood, however, that the amount of the compound or solid form actually administered will usually be determined by a physician, according to the relevant circumstances, including the condition to be treated, the chosen route of administration, the actual compound or solid form administered, the age, weight, and response of the individual patient, the severity of the patient's symptoms and the like.

The therapeutic dosage of a compound or solid form of the present invention can vary according to, e.g., the particular use for which the treatment is made, the manner of administration of the compound or solid form, the health and condition of the patient, and the judgment of the prescribing physician. The proportion or concentration of a compound or solid form of the invention in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound or solid form selected, formulation of the excipient, and its route of administration. Effective doses can be extrapolated from dose-response curves derived from in vitro or animal model test systems.

The liquid forms in which the compounds, solid forms, and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

EXAMPLES

Example 1A. Experimental Methods

The following experimental methods were used in Examples 1-17.

1.1 XRPD

In the below examples, XRPD diffractograms were collected on either a Bruker D8 diffractometer or a PANalytical Empyrean diffractometer. Conditions are described as follows:

Bruker AXS D8 Advance

XRPD diffractograms were collected on a Bruker D8 diffractometer using Cu Kα radiation (40 kV, 40 mA) and a θ-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

The details of the data collection method are:
Angular range: 2 to 42° 2θ
Step size: 0.05° 2θ
Collection time: 0.5 s/step (total collection time: 6.40 min)
PANalytical Empyrean XRPD diffractograms were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel$^{3D}$ detector, placed on the diffracted beam, was fitted with a receiving slit and 0.04 rad Soller slits. The software used for data collection was X'Pert Data Collector using X'Pert Operator Interface. The data were analyzed and presented using Diffrac Plus EVA or HighScore Plus.

Samples were prepared and analyzed in either a metal or Millipore 96 well-plate in transmission mode. X-ray transparent film was used between the metal sheets on the metal well-plate and powders (approximately 1-2 mg) were used as received. The Millipore plate was used to isolate and analyze solids from suspensions by adding a small amount of suspension directly to the plate before filtration under a light vacuum.

The scan mode for the metal plate used the gonio scan axis, whereas a 2θ scan was used for the Millipore plate.

The details of the standard screening data collection method are:
Angular range: 2.5 to 32.0° 2θ
Step size: 0.0130° 2θ
Collection time: 12.75 s/step (total collection time of 2.07 min)

When needed, a high resolution method with data collection was used:
Angular range: 2.5 to 42.0° 2θ
Step size: 0.0130° 2θ
Collection time: 36.72 s/step (total collection time of 8.32 min)

Non-Ambient Conditions XRPD diffractograms were collected on a PANalytical Empyrean diffractometer using Cu Kα radiation (45 kV, 40 mA) in reflection geometry. The instrument is fitted with an Anton Paar CHC plus$^+$ stage fitted with graphite/Kapton windows and equipped with air cooling coupled with a proUmid MHG32 Modular Humidity Generator or a low vacuum pump system using an Edwards RV3 pump. A programmable divergence slit (in automatic mode), with a 10 mm fixed incident beam mask, Ni filter and 0.04 rad Soller slits were used on the incident beam. A PIXcel$^{3D}$ detector, placed on the diffracted beam, was fitted with a programmable anti-scatter slit (in automatic mode) and 0.04 rad Soller slits.

The software used for data collection was X'Pert Data Collector and the data analyzed and presented using Diffrac Plus EVA or Highscore Plus.

For variable temperature (VT-XRPD) experiments the samples were prepared and analysed in an Anton Paar chromed sample holder with silicon wafer insert. A heating/cooling rate of 10° C./min was used with a 2 min isothermal hold before the measurement started. The measurement parameters are as per the standard screening data collection method (detailed above). Measurements were taken at the following temperatures: 25° C., 150° C. and 25° C.

For low vacuum experiments the samples were prepared and analyzed in an Anton Paar chromed sample holder with silicon wafer insert, with a vacuum applied of $3 \times 10^3$ Pa. A heating/cooling rate of 10° C./min was used and sample was heated to 40° C. Measurements were made once per hour for 63 hours. The measurement parameters are as per the standard screening data collection method (detailed above).

1.2 Nuclear Magnetic Resonance $^1$H NMR spectra were collected on a Bruker 400 MHz instrument equipped with an auto-sampler and controlled by a DRX400 console. Samples were prepared in DMSO-$d_6$ solvent, unless otherwise stated. Automated experiments were acquired using ICON-NMR configuration within Topspin software, using standard Bruker-loaded experiments ($^1$H, $^{13}$C {$^1$H}, DEPT135). Off-line analysis was performed using ACD Spectrus Processor.

1.3 Differential Scanning Calorimetry (DSC)
TA Instruments Q2000

DSC data were collected on a TA Instruments Q2000 equipped with a 50 position auto-sampler. Typically, 0.5-3 mg of each sample, in a pin-holed aluminium pan, was heated at 10° C./min from 25° C. to 300° C. A purge of dry nitrogen at 50 ml/min was maintained over the sample.

The instrument control software was Advantage for Q Series and Thermal Advantage and the data were analyzed using Universal Analysis or TRIOS.

TA Instruments Discovery DSC

DSC data were collected on a TA Instruments Discovery DSC equipped with a 50 position auto-sampler. Typically, 0.5-3 mg of each sample, in a pin-holed aluminum pan, was heated at 10° C./min from 25° C. to 300° C. A purge of dry nitrogen at 50 ml/min was maintained over the sample.

The instrument control software was TRIOS and the data were analyzed using TRIOS or Universal Analysis.

1.4 Thermo-Gravimetric Analysis (TGA)
TA Instruments Q500

TGA data were collected on a TA Instruments Q500 TGA, equipped with a 16 position auto-sampler. Typically, 5-10 mg of each sample was loaded onto a pre-tared aluminum DSC pan and heated at 10° C./min from ambient temperature to 350° C. A nitrogen purge at 60 ml/min was maintained over the sample.

The instrument control software was Advantage for Q Series and Thermal Advantage and the data were analyzed using Universal Analysis or TRIOS.

TA Instruments Discovery TGA

TGA data were collected on a TA Instruments Discovery TGA, equipped with a 25 position auto-sampler. Typically, 5-10 mg of each sample was loaded onto a pre-tared aluminum DSC pan and heated at 10° C./min from ambient temperature to 350° C. A nitrogen purge at 25 ml/min was maintained over the sample.

The instrument control software was TRIOS and the data were analyzed using TRIOS or Universal Analysis.

1.5 Polarized Light Microscopy
Leica LM/DM Polarized Light Microscope

Samples were analyzed on a Leica LM/DM polarized light microscope with a digital video camera for image capture. A small amount of each sample was placed on a glass slide, with or without immersion oil, and covered with a glass slip. The sample was viewed with appropriate magnification and partially polarized light, coupled to a λ false-color filter. Images were captured using StudioCapture or Image ProPlus software.

Nikon LM/DM Polarised Light Microscope

Samples were studied on a Nikon SMZ1500 polarized light microscope with a digital video camera connected to a DS Camera control unit DS-L2 for image capture. The sample was viewed with appropriate magnification and partially polarized light, coupled to a λ false-color filter.

1.6 Gravimetric Vapor Sorption (GVS)

Sorption isotherms were obtained using a SMS DVS Intrinsic moisture sorption analyzer, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite.

| Method for SMS DVS Intrinsic experiments | |
|---|---|
| Parameter | Value |
| Adsorption - Scan 1 | 40-90 |
| Desorption, Adsorption - Scan 2 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time |
| Number of cycles | 2 |

1.7 Chemical Purity Determination by HPLC

Purity analysis was performed on an Agilent HP1100 series system equipped with a diode array detector and using ChemStation software. The full method details are provided below:

| Parameter | Value |
|---|---|
| Type of method | Reverse phase with gradient elution |
| Sample Preparation | 0.25 mg/ml in DMSO |
| Column | Supelco Ascentis Express C18, 100 × 4.6 mm, 2.7 μm |
| Column Temperature (° C.) | 25 |
| Injection (μl) | 10 |
| Wavelength, Bandwidth (nm) | 255, 90 |
| Flow Rate (ml/min) | 2 |
| Phase A | 0.1% TFA in water |
| Phase B | 0.085% TFA in acetonitrile |

| Timetable | Time | % Phase | % Phase |
|---|---|---|---|
| | 0 | 95 | 5 |
| | 6 | 5 | 95 |
| | 6.2 | 95 | 5 |
| | 8 | 95 | 5 |

1.8 Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated. Data collection and analysis were performed using Tiamo software.

1.9 Ion Chromatography (IC)

Data were collected on a Metrohm 930 Compact IC Flex with 858 Professional autosampler and 800 Dosino dosage unit monitor, using IC MagicNet software. Accurately weighed samples were prepared as stock solutions in a suitable solvent. Quantification was achieved by comparison with standard solutions of known concentration of the ion being analyzed. Analyses were performed in duplicate and an average of the values is given unless otherwise stated.

| Method for cation chromatography | |
|---|---|
| Parameter | Value |
| Type of method | Cation exchange |
| Column | Metrosep C 4 - 250 (4.0 × 250 mm) |
| Column Temperature (° C.) | Ambient |
| Injection (μl) | Various |
| Detection | Conductivity detector |
| Flow Rate (ml/min) | 0.9 |
| Eluent | 1.7 mM nitric acid 0.7 mM dipicolinic acid in a 5% acetone aqueous solution. |

| Method for anion chromatography | |
|---|---|
| Parameter | Value |
| Type of method | Anion exchange |
| Column | Metrosep A Supp 5 - 150 (4.0 × 150 mm) |
| Column Temperature (° C.) | Ambient |
| Injection (μl) | Various |
| Detection | Conductivity detector |
| Flow Rate (ml/min) | 0.7 |
| Eluent | 3.2 mM sodium carbonate 1.0 mM sodium hydrogen carbonate in a 5% acetone aqueous solution. |

1.10 Single Crystal X-Ray Diffraction (SCXRD)

Data were collected on a Rigaku Oxford Diffraction Supernova Dual Source, Cu at Zero, Atlas CCD diffractometer equipped with an Oxford Cryosystems Cobra cooling device. The data were collected using Cu Kα or Mo Kα radiation as stated in the experimental tables. Structures were solved and refined using the Bruker AXS SHELXTL suite or the OLEX$^2$ crystallographic software. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter. A reference diffractogram for the crystal structure was generated using Mercury (1).

1.11 Crystal 16

A Crystal 16 crystallization system (Technobis, NL) was used to determine the solubility and metastable zone of the material as a function of temperature. Slurries of the API, in different overall concentrations, were prepared by adding a known amount of solid to a known amount of chilled solvent (between 0.5 and 1.5 ml) and stirred at 350 rpm using a magnetic bar. The saturation temperature was measured through cycles of heating and cooling from 20 to 90° C. at 0.5° C./min.

Upon increasing the temperature, the solid completely dissolved and the suspension became a clear solution such that the light transmission reached its maximum value. This temperature was assigned as the clear point, which was assumed to coincide with the saturation temperature. Then, by cooling the solution at a rate of 0.5° C./min, the temperature at which particles first formed was detected by a decrease in the light transmission. This was assigned as the cloud point. The points were fitted by a Van't Hoff equation and the difference between the cloud and the clear points defined the metastable zone width (MSZW) of the system. The instrument control software was Crystallization Systems and the data were analyzed using Crystal Clear and Microsoft Excel.

Example 1B. Additional Instrumental Methods

The following instrumental methods were used for the experiments described in Examples 18-20.

| 2.1 X-ray Powder Diffractometer (XRPD) | |
|---|---|
| Instrument | Bruker D8 Advance |
| Detector | LYNXEYE_XE_T(1D mode) |
| Open angle | 2.94° |
| Scan mode | Continuous PSD fast |
| Radiation | Cu/K-Alpha1 ($\lambda$ = 1.5418 Å) |
| X-ray generator power | 40 kV, 40 mA |
| Step size | 0.02° |
| Time per step | 0.12 second per step |
| Scan range | 3° to 40° |
| Primary beam path slits | Twin_Primary motorized slit 10.0 mm by sample length; SollerMount axial soller 2.5° |
| Secondary beam path slits | Detector OpticsMount soller slit 2.5°; Twin_Secondary motorized slit 5.2 mm |
| Sample rotation speed | 15 rpm |

| 2.2 Differential Scanning Calorimetry (DSC) | |
|---|---|
| Instrument | TA Discovery 2500 or Q2000 |
| Sample pan | Tzero pan and Tzero hermetic lid with a pin hole |
| Temperature range | 30 to 250° C. or before decomposition |
| Heating rate | 10° C./min |
| Nitrogen flow | 50 mL/min |
| Sample mass | ~1-2 mg |

| 2.3 Thermal Gravimetric Analysis (TGA) | |
|---|---|
| Instrument | Discovery 5500 |
| Sample pan | Aluminum, open |
| Nitrogen flow | Balance 10 mL/min; sample 25 mL/min |
| Start temperature | Ambient condition (below 35° C.) |
| Final temperature | 300° C. or abort next segment if weight <80% (w/w) (The weight loss of the compound is no more than 20% (w/w)) |
| Heating rate | 10° C./min |
| Sample mass | ~2-10 mg |

| 2.4 Dynamic Vapor Sorption (DVS) for Form A | |
|---|---|
| Instrument | Advantage |
| Total gas flow | 200 sccm |
| Oven temperature | 25° C. |
| Solvent | Water |
| Method | Cycle: 40-0-95-0-95-0-40% RH Stage Step: 10% Equilibrium: 0.002 dm/dt (%/min) Minimum dm/dt stability duration: 60 min Maximum dm/dt stage time: 360 min |

| 2.5 Dynamic Vapor Sorption (DVS) for Form B | |
|---|---|
| Instrument | Intrinsic |
| Total gas flow | 200 sccm |
| Oven temperature | 25° C. |
| Solvent | Water |
| Method | Cycle: 40-95-0-95-40% RH Stage Step: 10% Equilibrium: 0.002 dm/dt (%/min) Minimum dm/dt stability duration: 60 min Maximum dm/dt stage time: 360 min |

| 2.6 Polarized Light Microscope (PLM) | |
|---|---|
| Instrument | OLYMPUS BX53LED |
| Method | Crossed polarizer, silicone oil added |
| Objective lens | 4X/10X/20X/40X |

| 2.7 Nuclear Magnetic Resonance (NMR) | |
|---|---|
| Instrument | Bruker Avance-AV 400M |
| Frequency | 400 MHz |
| Probe | 5 mm PABBO BB-1H/D |
| Number of scan | 8 |
| Temperature | 297.6 K |
| Relaxation delay | 1 second |

| 2.8 High Performance Liquid Chromatograph (HPLC) | |
|---|---|
| Instrument | Shimadzu LC-20ADXR Wave length: 286 nm; 220 nm Column: Waters Xbridge C18 4.6 × 250 mm, 5 μm Detector: DAD Column temperature: 40° C. Flow rate: 1.0 mL/min Mobile phase A: 10 mM Ammonium bicarbonate ($NH_4HCO_3$) Mobile phase B: Acetonitrile Diluent: 25:75(v:v) Mobile Phase A:Mobile Phase B Injection volume: 3 μL Concentration 0.25 mg/mL Gradient: |

-continued

| 2.8 High Performance Liquid Chromatograph (HPLC) | | |
|---|---|---|
| Time (min) | Mobile Phase A (%) | Mobile Phase B (%) |
| 0.00 | 70 | 30 |
| 0.01 | 70 | 30 |
| 10.00 | 10 | 90 |
| 15.00 | 10 | 90 |
| 15.01 | 70 | 30 |
| 20.00 | 70 | 30 |

Example 2: Synthesis of Compound 1

The reactions described in Example 2 were run in glass or glass-lined steel equipment. Products were isolated and dried in an agitated filter/dryer (Hastelloy). In addition, isolation could be performed in any fixed-plate filter (e.g., Nutsche or Aurora) or a centrifuge, and drying done in a tray dryer.

Step 1. tert-butyl 2-(4-((4-chlorobenzyl)oxy)phenyl)-6,7-dihydrooxazolo[4,5-c]pyridine-5(4H)-carboxylate Acetonitrile (15.6 kg) was charged to an inerted vessel, followed by tert-butyl 2-(4-hydroxyphenyl)-6,7-dihydrooxazolo[4,5-c]pyridine-5(4H)-carboxylate (1.0 kg, limiting reagent; see U.S. Pat. No. 8,796,262 at col. 44), p-chlorobenzyl bromide (740 g, 1.14 equiv.), and powdered potassium carbonate (880 g, 1.06 mol-equiv). The mixture was heated to 50±5° C. and agitated at that temperature until the starting material was consumed, as judged by HPLC. The mixture was cooled to 25±5° C., whereupon water (USP purified, 40 kg) was added. After agitating for 1 hour, the product was filtered and washed with water (USP purified, 4 kg).

The wet product was reslurried in water (USP purified, 15 kg) for at least 1 hour at ambient temperature, filtered, and washed with water (USP purified, 5 kg). The product was dried at 50±5° C. under >26 in-Hg until the KF is 1%, at least 24 hours. The yield of the product was about 1.18 kg (85%).

Step 2. 2-(4((4-chlorobenzyl)oxy)phenyl)-4,5,6,7-tetrahydrooxazolo[4,5-c]pyridine tert-butyl 2-(4-((4-Chlorobenzyl)oxy)phenyl)-6,7-dihydrooxazolo[4,5-c]pyridine-5(4H)-carboxylate (1.0 kg, limiting reagent) was charged to an inerted vessel, followed by methylene chloride (13.3 kg) and trifluoroacetic acid (2.64 kg, ca. 10 equiv.). The mixture was stirred at 25±5° C. until the starting material was consumed, as judged by HPLC, which was at least 16 hours. The reaction was concentrated under vacuum to the minimum stirrable volume (MSV), after which ethyl acetate (4 kg) is added. The distillation was continued to MSV, and again ethyl acetate (4 kg) was added. The reaction was concentrated to MSV one final time, after which ethyl acetate (7.2 kg) was again added. A suspension formed. After stirring for 15 minutes, sodium bicarbonate (1.03 kg) in water (USP purified, 10.45 kg) was added until the pH of the aqueous layer was 7.0-8.5. The suspension was stirred for 15 more minutes, after which the pH was confirmed to be 7.0-8.5. The product was filtered and washed with water (USP purified, 4.0 kg).

The wet product was reslurried in water (USP purified, 10 kg) for at least 1 hour at ambient temperature, filtered, and washed with water (USP purified, 10 kg). The product was dried at 50±5° C. under ≥26 in-Hg until the KF is ≤1%, at least 24 hours. The yield was about 0.696 kg (90%).

Step 3. (1s,3s)-3-(2-(4-((4-chlorobenzyl)oxy)phenyl)-6,7-dihydrooxazolo[4,5-c]pyridin-5(4H)-yl)cyclobutane-1-carboxylic acid 2-(4-((4-Chlorobenzyl)oxy)phenyl)-4,5,6,7-tetrahydrooxazolo[4,5-c]pyridine (1.0 kg, limiting reagent) was added to an inerted vessel, followed by methanol (12.7 kg) and 3-oxo-cyclobutane-1-carboxylic acid (0.413 kg, 1.24 equiv.). The resulting mixture was stirred at 25±5° C. for a minimum of 2 hours. Then a solution of sodium cyanoborohydride (0.399 kg, 2.17 mol-equiv.) in methanol (2.50 kg) was added at a rate that maintains the temperature below 35° C. The addition vessel was rinsed with methanol (0.74 kg) and the rinse added to the reaction. Stirring was continued without the addition of heat (20-35° C.) until an IPT showed that the sum of the concentrations of starting material and imine was consumed, as judged by HPLC. The product, which had precipitated, was filtered and washed with methanol (4.75 kg) and water (USP purified, 6.03 kg). The product was dried at 50±5° C. under >26 in-Hg until the KF is 1%, at least 24 hours. The yield of crude product was about 1.09 kg (85%).

Step 4. Recrystallization from DMSO

The crude product (1.0 kg) of Step 3 was charged to an inerted vessel, followed by DMSO (26.8 kg). The mixture was heated to 70±5° C., at which point a solution was obtained. The mixture was cooled as close to 20° C. as possible. The crystallized product was filtered and washed with three portions of methanol (3.2 kg each). The product was dried at 50±5° C. under ≥26 in-Hg.

Step 5. Recrystallization from Acetic Acid/Water

The product from Step 4 (1.0 kg) was charged to an inerted vessel, followed by acetic acid (6.29 kg). The mixture was heated to 70-75° C., at which point a solution was obtained. The solution was filtered through a 0.2-micron cartridge filter and the temperature of the filtrate readjusted to 70-75° C., if necessary. Water (USP purified, 0.85 kg) was added, followed by 2 wt % of Compound 1 seeds. The mixture was stirred at 70-75° C. for about 30 minutes. Then additional water (USP purified, 0.85 kg) as added over about 2 hours while maintaining the temperature at 70-75° C. Next, the batch was cooled at about 0.6° C./min to 20±3° C., where it was agitated for at least 12 hours. The product was filtered, washed with water (USP purified, 2.0 kg) and dried at 35±5° C. with a nitrogen purge until the level of residual acetic acid was <5000 ppm. The solid product was then re-equilibrated to form the monohydrate, Compound 1 Form B, which is characterized in Example 13.

Alternatively, the crude product from Step 3 can be used directly in the recrystallization form acetic acid/water to provide Compound 1 Form B.

Example 3: Initial Preparation and Analysis of Polymorphs

Compound 1 (100 mg) was dispensed into 4 ml vials. To these, DMSO (25 vol) was added and the suspensions heated to 80° C. with 500 rpm magnetic stirring to give clear solutions. To one sample, H$_2$O (10 vol) was added (Sample 01), and formation of a white precipitate was observed. To the second sample, no antisolvent was added (Sample 02). Samples were cooled to 25° C. at 0.1° C./min then held isothermally at 25° C. for 8 hours. Solids were isolated by filtration and dried under positive pressure prior to drying in a vacuum oven at 40° C. overnight.

Separately, Compound 1 (100 mg) was dispensed into 4 ml vials. To these, acetic acid (10 vol) was added and the suspensions heated to 80° C. with 500 rpm magnetic stirring to give clear suspensions. To one sample H$_2$O (10 vol) was added (Sample 03), and formation of a white precipitate was observed. Samples were cooled to 25° C. at 0.1° C./min, then held isothermally at 25° C. for 8 hours. The second sample (Sample 04) was observed to be clear. To this, acetonitrile (30 vol) was added dropwise until turbidity was observed, this sample was subsequently stirred for a further hour prior to isolation by centrifugation. Sample 03 was isolated by filtration and dried under suction. Both samples were dried in a vacuum oven at 40° C. overnight.

For clarity, the different experimental parameters each sample was subjected to are detailed in Table 1.

TABLE 1

Experimental parameters and observations from the attempted preparation of Form A and B

| Sample | Solvent | Antisolvent | Observation on | Antisolvent added |
|---|---|---|---|---|
| 01 | DMSO | H$_2$O | White suspension | N/A |
| 02 | DMSO | N/A | White suspension | N/A |
| 03 | Acetic acid | H$_2$O | White suspension | N/A |
| 04 | Acetic acid | N/A | Clear solution | Acetonitrile |

In each of the experiments a white solid was successfully isolated, analysis of the solids is detailed in Table 2. In no experiment was Form A successfully isolated, instead in the experiments in which DMSO was used as a solvent, (Sample 01 and Sample 02) Form C was observed. Form C had an H-NMR spectrum consistent with Compound 1, and no mass loss was noted in the TGA thermogram prior to the start of thermal degradation at 275° C. DSC analysis of the material showed a small exotherm with onset 242.4° C. proceeding a sharp endotherm at 252.8° C.

In each of the experiments in which acetic acid was used as a solvent, material with an XRPD pattern corresponding to Form B was isolated. $^1$H-NMR analysis of the material was consistent with the structure of the supplied material, with an additional peak corresponding to 0.04 molar equivalents of acetic acid. The TGA thermogram of the material exhibited a mass loss of 3.5% between 40 and 140° C. consistent with 0.88 molar equivalents of water. The corresponding DSC thermogram contained a broad endotherm between 40 and 140° C., prior to a sharp endotherm with onset 244.8° C.

TABLE 2

Analysis of material from attempted preparation of Form A and B

| Sample | XRPD | $^1$H-NMR | TGA | DSC |
|---|---|---|---|---|
| 01 | Form C | Not measured | Not measured | Not measured |
| 02 | Form C | Consistent with structure | Start of thermal degradation at 275° C. | Small exotherm onset 242.4° C. (16 J/g) proceeding sharp endotherm at 252.8° C. (119 J/g) |
| 03 | Form B | Not measured | Not measured | Not measured |
| 04 | Form B | Consistent with structure. 0.04 equivalents of acetic acid. | 3.5% mass loss between 40 and 140° C. consistent with 0.88 equivalents of water. Start of thermal degradation at 275° C. | Broad endotherm between 40 and 140° C. (170 J/g), Sharp endotherm onset 244.8° C. (137 J/g). |

Taken together these data demonstrate the successful preparation of Form B and the isolation of Form C. When overlaid, the XRPD patterns of the Form C and Form B material are consistent with the XRPD of the solid product resulting from Example 2.

Example 4. Solubility of Compound 1

The solubility of Compound 1 was studied. To do so, metastable zone width curves were obtained using the Crystal 16. Experiments using neat acetic acid were not performed due to the very high solubility of the compound.

The solubility of compound 1 (various masses) in DMAC and DMSO (1 ml) was analyzed on the Crystal 16 (between 25-90° C. for DMSO and 0-90° C. for DMAC). A heating/cooling rate of 0.5° C./min and a stirring rate of 300 rpm was used for all samples. The resulting turbidity/temperature plots were analyzed to obtain solubility curves and determine the metastable zone width. Any precipitated solids were isolated by filtration and analyzed by XRPD.

The solubility of Compound 1 in DMSO increased with increased temperature. Precipitation of material was observed on cooling resulting in a metastable zone width of ca. 30° C. XRPD diffraction analysis of the isolated material showed it in all instances to correspond to Form C.

The solubility of Compound 1 in DMAC increases with increased temperature. Precipitation of material was observed on cooling resulting in a metastable zone width of ca. 30° C. XRPD diffraction analysis of the isolated material showed that in all but one instance the isolated material was Form C. In the remaining instance, the isolated material was analyzed while still damp and was shown to have an XRPD pattern corresponding to Form D. Upon drying, the Form D material converted to Form C. Form D was therefore assigned as a metastable DMAC solvate, which readily desolvates on drying to Form C.

Example 5. Relative Thermodynamic Stability of Form B and Form C

Determination of the relative stabilities of Form B and Form C was undertaken to identify which material was more thermodynamically stable in process relevant solvents. As a suspected solvate was isolated from experiments where DMAC was used as a solvent, only DMSO and acetic acid were determined to be appropriate process solvents. Combinations of these solvents with relevant antisolvents were therefore selected for the competitive slurry experiments. As Compound 1 resulting from Example 2 was shown to be composed of Form B and C, this material was used as the starting material.

Compound 1 (from Example 2) was dispensed into HPLC vials. To these, 1 ml of selected solvents was subsequently added to give a suspension. Materials were slurried for 72 hours at 90° C., 50° C. or 25° C. with 500 rpm stirring. Material was subsequently isolated by centrifugation and analyzed by XRPD.

The results of the competitive slurries are shown in Table 3. In all instances, the material remained as a slurry throughout the experiments. XRPD analysis of the isolated material demonstrated that in all six of the experiments in which acetic acid was a component of the solvent mixture, Form B was the sole detectable polymorph after 72 hours of slurrying. This result shows that Form B is more thermodynamically stable than Form C in the respective acetic acid mixtures and temperatures investigated.

In the remaining experiments Form B was found to be the sole detectable polymorph after 72 hours of slurrying except for the experiments in which DMSO was used as a solvent at elevated temperature. Material isolated from the experiment, where Compound 1 was slurried at 90° C. in DMSO for 72 hours had an XRPD pattern consistent with poorly crystalline Form A. This indicates that Form A is the most thermodynamically stable polymorph at 90° C. in DMSO. Material isolated from the experiment where Compound 1 was slurried in DMSO for 72 hours at 50° C. was shown to be poorly crystalline by XRPD and assignment of a form was not possible.

Taken together, these results demonstrate that in the majority of experimental conditions assessed, Form B is more thermodynamically stable than Form C, and that Form A is the most thermodynamically stable polymorph at 90° C. in DMSO.

TABLE 3

Observations and results of competitive slurries of Form B and C in process relevant solvents

| Solvent | Temp. | Observations after slurrying | XRPD analysis |
| --- | --- | --- | --- |
| DMSO | 90° C. | White solid in orange solution | Poorly crystalline Form A |
| DMSO:H$_2$O (1:1) | 90° C. | White solid in orange solution | Poorly crystalline Form B |
| Acetic acid:H$_2$O (1:1) | 90° C. | Cloudy white suspension | Form B |
| Acetic acid:MeCN (1:3) | 90° C. | Cloudy white suspension | Form B |
| DMSO | 50° C. | Cloudy white suspension | Poorly crystalline |
| DMSO:H$_2$O (1:1) | 50° C. | Cloudy white suspension | Poorly crystalline Form B |
| Acetic acid:H$_2$O (1:1) | 50° C. | Cloudy white suspension | Form B |
| Acetic acid:MeCN (1:3) | 50° C. | Cloudy white suspension | Form B |
| DMSO | 25° C. | Cloudy white suspension | Poorly crystalline Form B |
| DMSO:H$_2$O (1:1) | 25° C. | Cloudy white suspension | Poorly crystalline Form B |
| Acetic acid:H$_2$O (1:1) | 25° C. | Cloudy white suspension | Form B |
| Acetic acid:MeCN (1:3) | 25° C. | Cloudy white suspension | Form B |

Example 6. Solid State Characterization of Form B

Compound 1 (1 g) was dispensed into a 20 ml vial. To this, acetic acid (6 vol, 6 ml) was added and the suspension heated to 55° C. with 500 rpm magnetic stirring to give a clear light-yellow solution. H$_2$O (1 vol, 1 ml) was added, and formation of a white precipitate was observed. A further 9 vol H$_2$O (9 ml) was added in 1 ml aliquots. The sample was cooled to 25° C. at 0.3° C./min then held isothermally at 25° C. for 1 hour. The white precipitate was isolated by filtration, dried under suction for 30 minutes, then dried in a vacuum oven overnight at 40° C.

Form B was successfully isolated from antisolvent crystallization using acetic acid as the solvent and water as the antisolvent. The results from solid state characterization of Form B are shown in Table 4. Single crystal X-ray diffraction experiments (see Example 11) demonstrate that Form B is a monohydrate. XRPD analysis of the material isolated at this scale shows the material to have fewer peaks than that obtained at 100 mg scale (Example 3). The additional peaks observed at lower scale result from dehydration of the Form B material during drying and partial conversion to Pattern E. TGA analysis of the prepared Form B material corroborates this finding, as a mass loss of 3.9% is observed in the TGA thermogram between 40 and 150° C. which equates to 0.99 equivalents of water. This result is further supported by Karl Fischer analysis which shows the material to be 3.95% water by mass (1.0 molar equivalents of water).

The isolated Form B material was of relatively high purity by HPLC (97.9%) and had an $^1$H-NMR spectrum consistent with the molecular structure of the supplied material without peaks corresponding to the trans isomer. PLM images obtained of the particles show them to be a mixture of laths and larger aggregates typical of an uncontrolled antisolvent crystallization. A peak corresponding to 0.16 molar equivalents of acetic acid is present in the $^1$H-NMR spectrum. The TGA thermogram of the material shows a second mass loss of 1.9% between 210 and 260° C. which may correspond to 0.14 molar equivalents of acetic acid. It is evident from the corresponding DSC thermogram that this mass loss coincides with melting of the material (endotherm at 237.7° C.). Storage of the material at conditions of 40° C./75% RH and 25° C./97% RH for one week did not result in changes to material as measured by XRPD.

GVS analysis of the material shows a mass loss of 2.1% between 20 and 0% RH on the desorption cycle corresponding to 0.51 molar equivalents of water. This mass is regained on the following sorption cycle, albeit with hysteresis observed, indicative of hydrate formation.

Examination of the GVS kinetic plot indicates the material to not have fully equilibrated during desorption indicating dehydration to be incomplete.

With the single crystal X-ray powder diffraction data, this dataset demonstrates Form B is likely a monohydrate, which is stable under conditions of >20% RH and readily rehydrates after water loss.

TABLE 4

Characterization of Form B

| Description | White solid |
| --- | --- |
| XRPD | Crystalline Form B. Consistent with smaller scale, albeit with absence of peaks known to result from Pattern E. |
| $^1$H-NMR | Consistent with structure. 0.16 molar equivalents of acetic acid. |

TABLE 4-continued

Characterization of Form B

| | |
|---|---|
| TGA | 3.9% mass loss between 40 and 150° C., 0.99 equivalents of water. 1.9% mass loss between 210° C. and 260° C. (0.14 equivalents of acetic acid)* |
| DSC | Broad endotherm between 25° C.-100° C. (51 J/g). Onset of sharp endotherm at 237.7° C. (67 J/g). |
| Karl Fischer | 3.95% water by mass (1.0 equivalents) |
| HPLC Purity (a.u.c.) | 97.9% |
| PLM | Aggregates and laths |
| GVS | 2.1% mass loss between 20 and 0% RH, 0.51 equivalents of water. Hysteresis observed on hydration indicative of hydrate formation. Unchanged by XRPD post analysis. |
| Storage at 40° C./75% RH for one week | Unchanged by XRPD |
| Storage at 25° C./97% RH for one week | Unchanged by XRPD |

*Thermogravimetric analysis performed after rehydration of the material in air for 24 hours. TGA was previously performed after removal of the material from the vacuum oven from which the material was shown to contain 2.2% water.

Example 7. Construction of the Solubility Curves and Identification of the Metastable Zone of Form B in Acetic Acid/Water Mixtures In order to determine whether acetic acid/water represented a viable solvent system for the crystallization of Form B solubility curves of Form B in various acetic acid/water mixtures and subsequent modelling of the solubility behavior in DynoChem was undertaken.

Form B in acetic acid/water (9:1, 3:1, 3:2, 1:1 volume ratios, 0.5 ml) was analyzed on the Crystal 16 between 25 and 90° C. with a heating/cooling rate of 0.5° C./min and a stirring rate of 350 rpm. The resulting turbidity/temperature plots were analyzed to obtain solubility curves and determine the metastable zone width. Isolated solids were analyzed by XRPD. Solubility curves were subsequently input into the DynoChem crystallization toolbox to model the solubility of Form B as a function of solvent composition and temperature.

Compound 1 (1 g) was dispensed into a 20 ml vial. To this, 5 vol acetic acid (5 ml) was added and the suspension heated to 60° C. with 500 rpm magnetic stirring to give a clear solution. $H_2O$ (0.48 vol, 0.48 ml) was added dropwise by syringe pump over 90 seconds and the solution remained clear. Form B seeds (20 mg) were added and observed to sustain. The solution was stirred for 30 minutes prior to dropwise addition of water 4.36 vol (4.36 ml) by syringe pump over one hour. The resulting white suspension was cooled to 25° C. at 0.1° C./min then held isothermally for 9 hours prior to isolation by filtration. The resulting white solid was washed with $H_2O$ (2 vol) and dried under suction for 30 minutes.

The solubility curves of Form B in four different acetic acid:$H_2O$ mixtures (volume ratios 9:1, 3:1, 3:2 and 1:1) were determined using the Crystal 16. Solubilization of Form B was observed at varying temperatures, precipitation of material was only observed in the acetic acid:$H_2O$ 9:1, within the cooling ramp. In all instances the isolated material was shown to be Form B by XRPD. Precipitation of material in the experimental timeframe demonstrates that although the system exhibits a relatively large metastable zone, nucleation kinetics are not sufficiently slow as to prohibit crystallization without seeding. Curves corresponding to Van't Hoff equations were fitted to the solubility datasets obtained for each solvent mixture. It was evident that solubility of Form B varies as a function of solvent composition.

Once the solubility curves were obtained, values from the curves were inserted into the DynoChem crystallization toolbox to model the solubility of Form B as a function of solvent composition. Good agreement between the predicted and measured solubility values from the DynoChem model were obtained ($R^2$=0.999, error 4.8%). It was evident from the model that the relationship between solution composition and solubility of the Form B is non-linear, and that solubility increases with increasing acetic acid content.

Once solubility as a function of solvent composition had been successfully modelled, simulations in DynoChem were implemented in an attempt to locate a cooling or antisolvent crystallization which would give a satisfactory yield.

An antisolvent crystallization was identified in which, after dissolution Compound 1 in acetic acid, an initial water addition could be made to give a supersaturation ratio of 1.1 at a starting temperature of 60° C. giving a predicted yield of 90% after antisolvent ($H_2O$) addition and cooling to 25° C. The solid state analysis of the material is shown in Table 5.

TABLE 5

Results from crystallization identified from DynoChem model

| | |
|---|---|
| Description | White solid |
| Yield | 84% |
| XRPD | Crystalline Form B. Consistent with smaller scale. |
| $^1$H-NMR | Consistent with structure. 0.05 molar equivalents of acetic acid. No peaks corresponding to trans isomer. |
| TGA | 3.8% weight loss between 25 and 175° C. (0.96 molar equivalents of water). Start of thermal degradation at 275° C. |
| DSC | Broad endotherm with onset at 69.2° C. (107 J/g). Sharp endotherm with onset 243.3° C. (140 J/g). |
| Karl Fischer | 3.8% |
| HPLC Purity (a.u.c.) | 98.8% |
| PLM | Plates and aggregates |
| GVS | 0.25% mass loss between 20 and 0% RH on desorption cycle. 0.06 equivalents of water. Hysteresis observed on humidity increase. Sample unchanged by XRPD |
| Storage at 40° C./75% RH for one week | Unchanged by XRPD |
| Storage at 25° C./97% RH for one week | Unchanged by XRPD |

Form B material was isolated with a yield of 84%, which is lower than that predicted by the DynoChem solubility model (90%). This disparity is thought to result from the slow crystallization kinetics of the Form B material as indicated by the large metastable zone width observed in the Crystal 16 experiments. In the performed experiment, dissolution was not observed after seed addition, indicating that the system was metastable, adding validation to the DynoChem model which indicated the system to be supersaturated (supersaturation ratio 1.1).

Solid state analysis of the material indicated it to be a monohydrate (0.96 molar equivalents of water by TGA and Karl Fischer analysis). HPLC analysis showed the material to have been formed in high purity (98.8%) with no trans isomer evident in the $^1$H-NMR spectrum. PLM showed the material to be composed of plates with some aggregates present and the peak corresponding to acetic acid in the $^1$H-NMR spectrum was reduced indicative of a controlled crystallization procedure. Disparity can be seen between the GVS data of this sample, and that of the previously analyzed sample again, the kinetic GVS plot does not indicate the sample to have fully equilibrated during the desorption cycle, therefore, the mass loss is not thought to be representative of the water content of the sample.

The solubility of Form B in acetic acid/H$_2$O was successfully modelled as a function of temperature and solvent composition. The resulting model was used to identify an antisolvent crystallization for the isolation of Form B with a predicted yield of 90%. This crystallization was augmented with Form B being the sole polymorphic Form isolated. The material was isolated in 84% yield, with low residual solvent content and high purity. The resulting crystallization was therefore deemed suitable as a basis for a design of experiments study for isolation of Form B material with optimized yield and purity.

Example 8. Optimization of the Antisolvent Crystallization of Form B in Acetic Acid/H$_2$O Solvent Mixtures by a Design of Experiments Approach The initial screening solubility determination work demonstrated that the acetic acid/H$_2$O solvent system was the most suitable for further development. Optimization of the crystallization of Form B was subsequently undertaken by a design of experiments approach to assess whether an enhancement in yield and purity was possible.

Based on observations from preliminary experiments, a Design of Experiments ("DoE") study was performed to investigate the main factors that impact the crystallization process. A factorial design at two levels was selected as the most suitable design type for this screening purpose. The DoE study performed was a fractional factorial design of $2^{4-8}$.

DOE variables identified are in bold with underlining. These values, and the sample IDs are tabulated for clarity in Table 6. Compound 1 (1 g) was charged to a 20 ml boiling tube equipped with a cross stirrer bar. To this, acetic acid (5 ml, 5 vol) was added and the suspension heated to 50/70° C. with 500 rpm suspended magnetic stirring to give a clear solution on an HEL polybock. H$_2$O (various volumes) was then added dropwise to give an initial supersaturation ratio of 1.1/1.3. Seeds (20 mg) were then added (Yes/No) and stirred for 30 minutes prior to the addition of H$_2$O (2.5/4.2 ml) over 1/3 hours. The suspension was then cooled to 15/25° C. at 0.2/1.0° C./min and then held isothermally for 0.5/16 hours prior to isolation by filtration.

Samples were rinsed with H$_2$O then dried under suction for 30 minutes, then in a vacuum oven at 40° C. Samples were analyzed by XRPD, Karl Fischer, $^1$H-NMR and HPLC to determine form, residual solvent content, purity and presence of trans-isomer. The quantities of water added to give the desired supersaturation ratios are shown in Table 6.

TABLE 6

| | | | | DoE conditions | | | |
|---|---|---|---|---|---|---|---|
| Initial Temp. (° C.) | Seeding Ssat ratio | H$_2$O to add (ml) | Antisolvent addition time (hrs) | Cooling rate (° C./min) | Seeding | Isolation Temp. (° C.) | Resident time (hrs) |
| 50 | 1.1 | 4.2 | 1 | 1 | Yes | 25 | 0.5 |
| 70 | 1.3 | 4.2 | 1 | 1 | No | 15 | 0.5 |
| 70 | 1.1 | 2.5 | 1 | 1 | No | 25 | 16 |
| 50 | 1.3 | 2.5 | 1 | 1 | Yes | 15 | 16 |
| 70 | 1.1 | 2.5 | 3 | 1 | Yes | 15 | 0.5 |
| 50 | 1.3 | 2.5 | 3 | 1 | No | 25 | 0.5 |
| 50 | 1.3 | 4.2 | 1 | 0.2 | No | 25 | 16 |
| 50 | 1.1 | 4.2 | 3 | 1 | No | 15 | 16 |
| 50 | 1.1 | 2.5 | 3 | 0.2 | Yes | 25 | 16 |
| 70 | 1.1 | 4.2 | 1 | 0.2 | Yes | 15 | 16 |
| 70 | 1.3 | 2.5 | 3 | 0.2 | No | 15 | 16 |
| 70 | 1.3 | 4.2 | 3 | 1 | Yes | 25 | 16 |
| 70 | 1.1 | 4.2 | 3 | 0.2 | No | 25 | 0.5 |
| 50 | 1.3 | 4.2 | 3 | 0.2 | Yes | 15 | 0.5 |
| 70 | 1.3 | 2.5 | 1 | 0.2 | Yes | 25 | 0.5 |
| 50 | 1.1 | 2.5 | 1 | 0.2 | No | 15 | 0.5 |

The supplied Compound 1 (1 g) was charged to a 20 ml boiling tube equipped with a cross stirrer bar. To this, acetic acid (5 ml, 5 vol) was added and the suspension was heated to 50/70° C. with 500 rpm suspended magnetic stirring to give a clear solution on an HEL polybock. Water (various volumes) was then added dropwise to give an initial supersaturation ratio of 1.2. Seeds (20 mg) were then added and stirred for 30 minutes prior to the addition of water (3.35/6.0 vol, 3.35/6.0 ml) over two hours. The suspension was then cooled to 15/25° C. at 0.6° C./min and then held isothermally for 16 hours prior to isolation by filtration. Samples were rinsed with H$_2$O then dried under suction for 30 minutes, then in a vacuum oven at 40° C.

Samples were analyzed by XRPD, Karl Fischer, $^1$H-NMR and HPLC to determine form, residual solvent content, purity and presence of trans-isomer. DOE variables are identified in bold with underlining, these values, and the amount of water added to give the solution a supersaturation ratio of 1.2 are detailed in Table 7.

TABLE 7

| Experimental variables and used in design of experiments augmentation procedures | | | |
|---|---|---|---|
| Initial Temperature | H$_2$O added to give supersaturation | Antisolvent volume added | Isolation temperature (° C.) |
| 50 | 0.29 | 3.35 | 15 |
| 70 | 0.85 | 3.35 | 25 |
| 70 | 0.85 | 6 | 25 |

The experimental parameters, and the high and low values selected for the design of experiments study are shown in Table 8. The selected responses were yield, trans isomer content, purity, residual acetic acid content, Form and residual water content.

TABLE 8

Experimental parameters and variables used in the design of experiments study

| DoE Factor | DoE Factor High | DoE Factor Low |
|---|---|---|
| Initial Temperature (° C.) | 70 | 50 |
| Supersaturation ratio on seeding | 1.1 | 1.3 |

TABLE 8-continued

Experimental parameters and variables used in the design of experiments study

| DoE Factor | DoE Factor High | DoE Factor Low |
|---|---|---|
| Seeding | Yes | No |
| Antisolvent addition volume | 2.5 | 4.2 |
| Antisolvent addition duration | 1 | 3 |
| Cooling rate (° C./min) | 0.2 | 1 |
| Isolation temperature (° C.) | 15 | 25 |
| Resident Time (hours) | 0.5 | 16 |

The antisolvent crystallization of Form B in the acetic acid/water system was investigated using a design of experiments approach. In all instances, Form B was the sole polymorph isolated, in high purity by HPLC with no trans isomer present as evidenced by $^1$H-NMR. The design of experiments model indicated that high initial temperature, and high isolation temperature resulted in enhanced yield and low residual acetic acid content. This result was validated in the subsequent augmentation experiments. Furthermore, increased antisolvent content was shown to further increase yield, with no decrease in purity or increase in residual acetic acid content.

Example 9. Scale-up of Crystallization to 10 g Scale

Compound 1 (10 g) was charged to a 140 ml HEL block vial. To this, acetic acid (5 vol, 50 ml) was added and the sample heated to 70° C. with suspended magnetic stirring (500 rpm) to give a clear solution. Hot filtration was performed to clear the sample of any debris and the filtrate heated to 70° C. in a 140 ml HEL vial with suspended magnetic stirring. H$_2$O (0.85 vol, 8.5 ml) was charged over one minute by syringe pump. Seeds were added to the sample (200 mg, Form B). The sample was stirred for 30 minutes prior to the dropwise addition of 6 vol H$_2$O (6 vol, 60 ml) over two hours by syringe pump. The sample was then cooled to 25° C. at 0.6° C./min, the sample was then held isothermally for 16 hours. The resulting white solid was isolated by filtration, rinsed with H$_2$O (2 vol, 20 ml) then dried under suction for 30 minutes. The sample was then dried in a vacuum oven at 40° C. overnight.

The crystallization was successfully scaled-up to 10 g scale. Form B was the sole polymorph isolated, analysis of this material is shown in Table 9. The material was isolated in 83% yield, with no trans isomer content evident by $^1$H-NMR. HPLC analysis showed the material to be of high purity (98.7%) with a residual acetic acid content of 0.04 molar equivalents. Disparity between the yield isolated from the 1 g scale experiment (88%) and the 10 g scale experiment are thought to have resulted from losses during the hot filtration performed prior to crystallization.

TABLE 9

Results from analysis of material from 10 g scale-up.

| Yield (%) | Form by XRPD | Residual Acetic Acid Content (molar equivalents) | Trans isomer | HPLC Purity (%) | Water content |
|---|---|---|---|---|---|
| 83 | Form B | 0.04 | None evident from NMR | 98.7 | 3.9% |

This experiment therefore demonstrates the scalability of this crystallization procedure for the isolation of polymorphically pure Form B material. For clarity and future use, the procedure is shown in Table 10. It should be noted, that Karl Fischer analysis of the acetic acid used was performed and was found to be 0.4% water by weight.

TABLE 10

Process summary for crystallization of Compound 1 Form B

| Step | Actions | Volume |
|---|---|---|
| 1. | Charge Compound 1 (1.00 wt, 1.00 equivalent) | 1.0 |
| 2. | Charge glacial acetic acid (5.0 vol) and start stirring | 6.0 |
| 3. | Heat up the slurry to 70° C. to give clear solution (clarification step can be included at this point) | 6.0 |
| 4. | Charge H$_2$O over 1 minute (0.85 vol) | 6.85 |
| 5. | Charge seed (0.02 wt) | 6.87 |
| 6. | Age for at least 30 minutes at 70° C. | 6.87 |
| 7. | Charge H$_2$O over 2 hours (6.0 vol) | 12.87 |
| 8. | Cool down to 25° C. at 0.6° C./min | 12.87 |
| 9. | Age for at least 12 hours at 25° C. | 12.87 |
| 10. | Filter the slurry and wash with water (2.0 vol) | 1.0 |
| 11. | Transfer to the vacuum oven and continue drying ≤40° C. | 1.0 |

Example 10. Variable Temperature and Humidity Analysis of Form B

Compound 1 Form B was analyzed using the Empyrean XRPD at a temperature of 25° C. The sample was then heated in situ using the variable temperature stage to 150° C. at a ramp rate of 10° C./min and held isothermally for 2 minutes whereupon a second XRPD measurement was made. The sample was then cooled to 25° C. at a ramp rate of 10° C./min held isothermally for 2 minutes whereupon a third XRPD measurement was made.

Compound 1 Form B was analyzed using the Empyrean XRPD at 40° C. The sample was then subjected to conditions of low vacuum at 40° C. and measured by XRPD. The sample was removed from the diffractometer and then left in conditions of 25° C., 50% RH for 48 hours. XRPD measurements were made after 8, 24, and 48 hours. Measurements after 24 and 48 hours were made on the high-resolution instrument, therefore the diffractograms exhibit lower signal to noise ratio.

In some instances, after isolation of material from the vacuum oven at 40° C. the XRPD pattern obtained exhibited additional peaks to that of Form B. Storage of the sample at ambient conditions for 48 hours was observed to result in disappearance of the peaks from the diffractogram demonstrating transformation of the material to Form B.

GVS analysis of the Form B material demonstrated a mass loss at low relative humidity corresponding with dehydration of the material, and rehydration at relative humidity >20% RH. The additional peaks observed in the diffractogram were therefore thought to arise from formation of the anhydrate during storage in the vacuum oven. To assess this postulate, in situ XRPD experiments were performed under conditions of vacuum and also under conditions of elevated temperature, as a mass loss concomitant with the loss of 1.0 equivalent of water was observed in the TGA thermograms of the material.

Heating the sample to 150° C. resulted in a change in Form by XRPD as evidenced by the additional peaks. This new form was denoted Form E. After cooling the material remains unchanged, with peak position changes attributed to thermal contraction of the material. The novel peaks observed on heating corresponded with those observed in the Form B sample post storage in the vacuum oven. Notably, the XRPD pattern of the material stored in the vacuum oven did not show complete conversion to the unstable anhydrate Form E, indicating incomplete removal of water occurs during vacuum drying. This result corresponds with GVS analysis in which only 50% of the bound water is removed in the experimental timeframe.

The single crystal X-ray diffraction experiments showed the length of the hydrogen bond between the water and the API to be short, indicative of strong bonding. This information explains why only partial conversion of Form B to the Form E was observed in both the GVS experiments and under conditions of low vacuum.

Example 11. Single Crystal Experiments

Crystals of Compound 1 Form B were obtained by evaporation from an acetic acid/water solution. A crystal of sufficient size and quality for analysis by single crystal X-ray diffraction was isolated, with approximate dimensions 0.19× 0.15×0.01 mm.

The crystal structure of Compound 1 Form B was determined at 100 K and a summary of all the structural data can be found in Table 11. Compound 1 Form B is triclinic, centrosymmetric space group P-1 with the final R1 [I>2σ (I)]=3.89%.

TABLE 11

| Structural Data for Form B | |
|---|---|
| Crystallization solvents | Acetic acid/water |
| Crystallization method | Evaporation |
| Empirical formula | C24H25ClN2O5 |
| Formula weight | 456.91 |
| Temperature | 100(2) K |
| Wavelength | 1.54184 Å |
| Crystal size | 0.190 × 0.150 × 0.010 mm |
| Crystal habit | Colorless thin plate |
| Crystal system | Triclinic |

TABLE 11-continued

| Structural Data for Form B | |
|---|---|
| Space Group | P-1 |
| Unit cell dimensions | a = 6.4333(2) Å; |
| | b = 8.3696(4) Å; |
| | c = 20.9458(10) Å; |
| | α = 89.689(4)°; |
| | β = 81.980(4)°; |
| | γ = 69.615(4)° |
| Volume | 1045.71(8) Å$^3$ |
| Z | 2 |
| Density (calculate) | 1.451 mg/m$^3$ |
| Absorption Coefficient | 1.966 mm$^{-1}$ |
| F(000) | 480 |

Example 12. Characterization of Compound 1 Form A

Conditions leading to the formation of Form A are described in, e.g., Example 5.

The XRPD pattern of Form A is shown in FIG. 1. Form A exhibits a DSC thermogram having an endotherm peak at a temperature of about 252° C. FIG. 2 shows a DSC thermogram of Compound 1, Form A. FIG. 3 shows a TGA thermogram of Compound 1, Form A. The TGA thermogram of Compound 1, Form A (FIG. 3) indicated that the sample contains about 43% DMSO by weight.

Example 13. Characterization of Compound 1 Form B

The preparation of Form B is described in, e.g., Examples 2, 3, 9.

The XRPD pattern of Form B is shown in FIG. 4 and the peak data is given below in Table 12.

TABLE 12

| XRPD Peak Data for Form B | |
|---|---|
| 2-Theta (°) | Intensity (%) |
| 8.5 | 100.0 |
| 15.1 | 31.6 |
| 16.1 | 12.1 |
| 16.5 | 23.2 |
| 17.0 | 11.6 |
| 17.9 | 9.8 |
| 18.6 | 15.8 |
| 20.9 | 13.6 |
| 21.3 | 19.6 |
| 21.5 | 20.2 |
| 21.9 | 8.1 |
| 23.5 | 51.1 |
| 24.6 | 23.7 |
| 25.2 | 26.7 |
| 25.5 | 71.3 |
| 26.5 | 10.6 |
| 27.4 | 19.7 |
| 28.2 | 20.4 |
| 29.2 | 10.1 |

Form B exhibits a DSC thermogram having an endotherm peak at a temperature of about 246° C. FIG. 5 shows a DSC thermogram of Compound 1, Form B. FIG. 6 shows a TGA thermogram of Compound 1, Form B. FIG. 7 shows a dynamic vapor sorption (DVS) isotherm plot of Compound 1, Form B.

Example 14. Characterization of Compound 1 Form C

The preparation of Form C is described in, e.g., Examples 3 and 4.

The XRPD pattern of Form C is shown in FIG. 8 and the peak data is given below in Table 13.

TABLE 13

XRPD Peak Data for Form C

| 2-Theta (°) | Intensity (%) |
|---|---|
| 7.4 | 19.3 |
| 11.0 | 9.7 |
| 14.7 | 8.7 |
| 15.6 | 10.0 |
| 16.5 | 14.9 |
| 17.3 | 13.8 |
| 17.5 | 10.7 |
| 18.5 | 15.3 |
| 19.4 | 13.6 |
| 19.5 | 12.5 |
| 22.2 | 94.5 |
| 25.0 | 80.6 |
| 25.4 | 100.0 |
| 28.2 | 86.3 |
| 29.8 | 32.9 |

Form C exhibits a DSC thermogram having an exotherm peak at a temperature of about 242° C. and an endotherm peak at a temperatures of about 253° C. FIG. 9 shows a DSC thermogram of Compound 1, Form C. FIG. 10 shows a TGA thermogram of Compound 1, Form C.

Example 15. Characterization of Compound 1 Form D

Conditions leading to the formation of Form D are described in, e.g., Example 4. The XRPD pattern of Form D is shown in FIG. 11.

Example 16. Characterization of Compound 1 Form E

The preparation of Form E is described in, e.g., Example 10.

The XRPD pattern of Form E is shown in FIG. 12 and the peak data is given below in Table 14.

TABLE 14

XRPD Peak Data for Form E

| 2-Theta (°) | Intensity (%) |
|---|---|
| 8.7 | 18.0 |
| 10.8 | 8.1 |
| 11.6 | 6.6 |
| 14.0 | 6.6 |
| 15.3 | 32.9 |
| 16.2 | 25.1 |
| 16.9 | 13.6 |
| 17.4 | 10.0 |
| 18.3 | 13.5 |
| 19.1 | 6.1 |
| 21.1 | 11.5 |
| 21.9 | 13.6 |
| 22.6 | 9.3 |
| 23.2 | 48.9 |
| 24.6 | 15.3 |
| 25.2 | 28.7 |
| 25.5 | 100.0 |

TABLE 14-continued

XRPD Peak Data for Form E

| 2-Theta (°) | Intensity (%) |
|---|---|
| 28.2 | 28.9 |
| 29.1 | 15.5 |
| 29.9 | 9.7 |

Example 17. Solubility in Aqueous Media

The room temperature equilibrium solubility was measured for Compound 1 Form A and Compound 1 Form B in different aqueous suspensions, as shown in the table below. Form A exhibited 3-6 times enhanced solubility as compared to Form B in the different aqueous systems tested, as measured by HPLC analysis of the supernatant from centrifuged samples.

| | Compound 1, Form A | | Compound 1, Form B | |
|---|---|---|---|---|
| Aqueous Suspension | Total drug in solution (µg/mL) | pH | Total drug in solution (µg/mL) | pH |
| 20% HP-BCD | 446.5 | 5.7 | 74.2 | 6.1 |
| 0.25% SLS | 23.7 | 6.9 | 7.8 | 6.0 |
| 0.2% HPMC | 1.3 | 7.2 | <1 | 6.7 |

HP-B-CD = hydroxy-propyl-beta-cyclodextrin;
SLS = sodium lauryl sulfate;
HPMC = hydroxypropyl methylcellulose Example 18A. Preparation of Compound 1, Form A Seeds Generally, a seed sample of Compound 1, Form A was prepared by removing as much water as possible from Compound 1, Form B and the DMSO solvent. Compound 1, Form B was heated in an open vial to ~180° C. to remove hydrated water. The sample was maintained at an elevated temperature for about 30 seconds. An amount of 500 µL of dry DMSO (dried over molecular sieves) was added to 60 mg of sample and the vial was capped/sealed. The capped/sealed vial was heated to about 120° C. under pressure to dissolve the solids (~1 minute). The sealed vial was rapidly cooled in a room temperature water bath while exposed to sonication in a sonic bath, until nucleation occurred as evidenced by the formation of a precipitate. The still hot light suspension was cooled to room temperature. After 1 hour of standing at room temperature, solids were isolated by filtration and washed with a few milliliters of dry acetone to afford Compound 1, Form A seeds.

Example 18B. Alternate Preparation and Characterization of Form A

Figure 13:
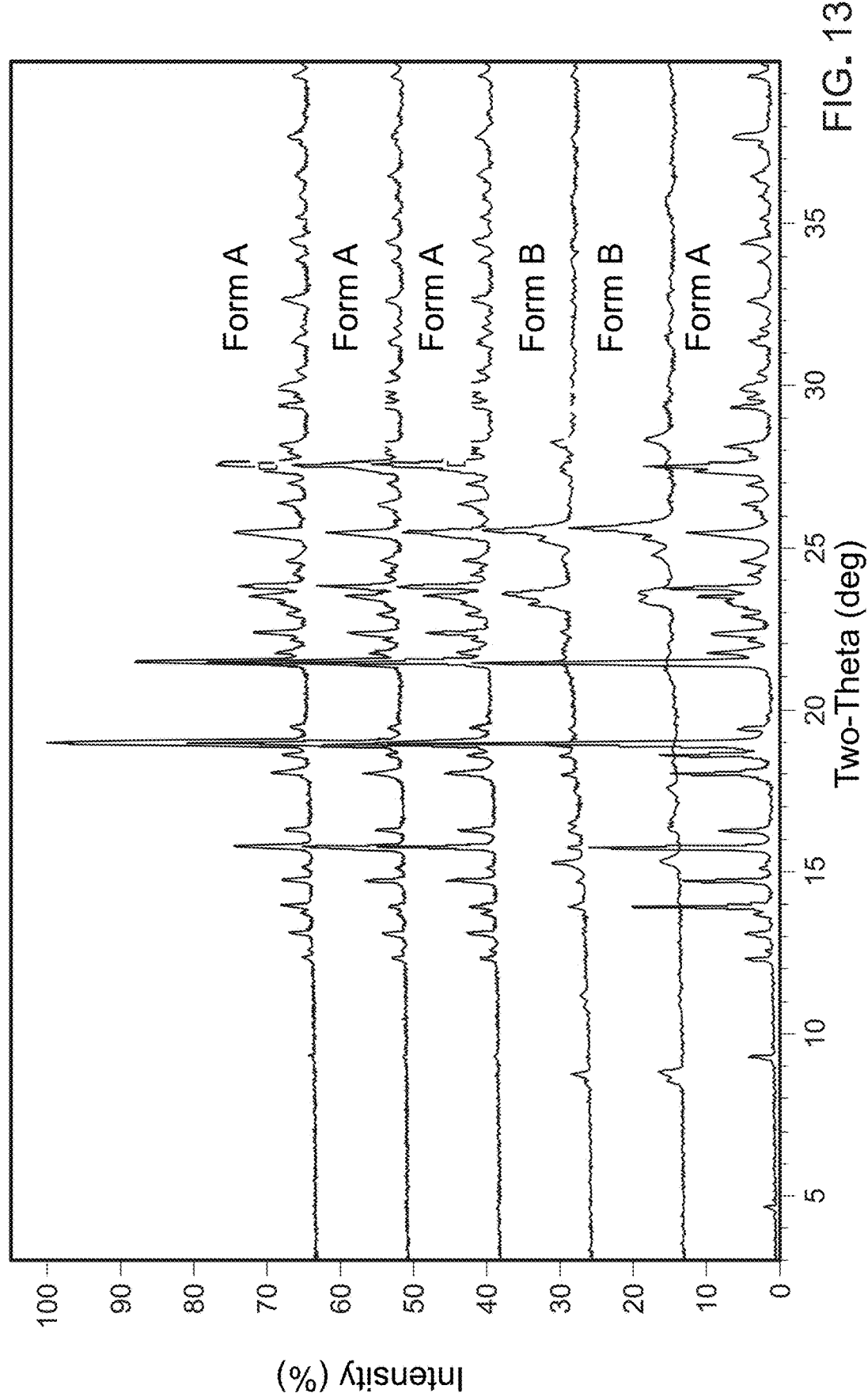
FIG. 13 shows an XRPD overlay of solids obtained from slow cooling Compound 1 in DMSO, as described in Example 18B.

About 30 mg of Compound 1 was added to 0.6 ml of DMSO at 100° C. with stirring, and a clear solution was obtained. After cooling to about 70° C., Compound 1 Form A seeds (see Example 18A) were added to the solutions of selected experiments to control polymorph formation. Solids were precipitated in about one minute. Next, about 0.6 ml ACN or EtOH was added to increase the yield. Results are summarized in Table 15 and FIG. 13.

TABLE 15

| Exp. ID | Solvent | Volume (ml) | Anti-solvent | Volume (ml) | Added Seeds | XRPD |
|---|---|---|---|---|---|---|
| 18A | DMSO | 0.6 | // | // | No | Form B |
| 18B | DMSO | 0.6 | EtOH | 0.6 | No | Form A + B |
| 18C | DMSO | 0.6 | EtOH | 0.6 | Yes | Form A |
| 18D | DMSO | 0.6 | ACN | 0.6 | Yes | Form A |
| 18E | DMSO | 0.6 | // | // | Yes | Form A |

// = Not carried out

Example 19. Scaled-up Preparation of Compound 1, Form A

About 18.8 g of Compound 1, Form B was added to 300 ml of DMSO with stirring. A clear solution was obtained after heating to 100° C. Then the clear solution was cooled at a rate of 1° C./min. At about 86° C., about 20 mg of Compound 1, Form A seeds were added (see Example 18A). After about 5 min, solids appeared. The suspension was further cooled to 25° C. at a rate of 0.1° C./min and stirring maintained at 25° C. for about 18 h. Solids were recovered by suction filtration. The obtained wet cake was dried at 60° C. under vacuum for 18 h. About 15.2 g of Compound 1, Form A was obtained as an off-white solid in about 81% yield. Characterization results are summarized in Tables 16-17 and FIGS. 14-18.

TABLE 16

Characterization of Form A

| Parameter | Method | Result |
|---|---|---|
| Purity | HPLC | 99.7% (286 nm) 99.2% (220 nm) |
| X-ray diffraction | 3-40° (2 theta) | High crystallinity (see FIG. 14 and Table 17) |
| DSC melting onset and enthalpy | DSC, 10° C./min | 252.0° C., decomposed upon melting (see FIG. 15) |
| Thermogravimetry | TGA, 10° C./min | 0.6% at 193.6° C. (see FIG. 16) |
| Residual solvent | $^1$H-NMR (DMSO-$d_6$) | No residual solvent (see FIG. 17) |
| Morphology | PLM | Plate crystals (see FIG. 18) |
| Karl Fischer | Coulometric | 0.06% water by weight |
| Yield | By weight | 81% |

TABLE 17

XRPD Peaks of Compound 1, Form A

| 2-Theta (°) | Intensity (%) |
|---|---|
| 4.7 | 6.9 |
| 9.3 | 16.1 |
| 12.4 | 8.4 |
| 12.6 | 2.9 |
| 13.1 | 14.6 |
| 13.9 | 92.9 |
| 14.8 | 28.1 |
| 15.1 | 2.9 |
| 15.8 | 45.3 |
| 16.3 | 25.6 |
| 18.1 | 31.6 |
| 18.6 | 75.3 |
| 19.0 | 100.0 |
| 19.5 | 15.2 |
| 21.5 | 82.5 |
| 21.8 | 17.5 |
| 22.1 | 5.2 |
| 22.4 | 24.6 |
| 23.0 | 6.4 |
| 23.3 | 27.3 |
| 23.5 | 16.8 |
| 23.8 | 28.0 |
| 24.2 | 4.2 |
| 24.6 | 9.5 |
| 25.5 | 20.7 |
| 26.0 | 4.3 |
| 26.4 | 9.8 |
| 27.0 | 10.3 |
| 27.4 | 46.6 |
| 27.5 | 27.6 |
| 28.1 | 12.8 |
| 29.4 | 11.1 |
| 29.8 | 5.5 |
| 29.9 | 18.6 |
| 30.5 | 2.6 |
| 31.4 | 11.6 |
| 31.8 | 2.0 |
| 32.1 | 1.6 |
| 32.7 | 10.8 |
| 33.9 | 4.2 |
| 34.4 | 14.0 |
| 34.9 | 1.2 |
| 35.3 | 2.2 |
| 35.9 | 5.1 |
| 36.4 | 6.0 |
| 37.7 | 36.6 |
| 39.6 | 13.4 |

Figure 19:
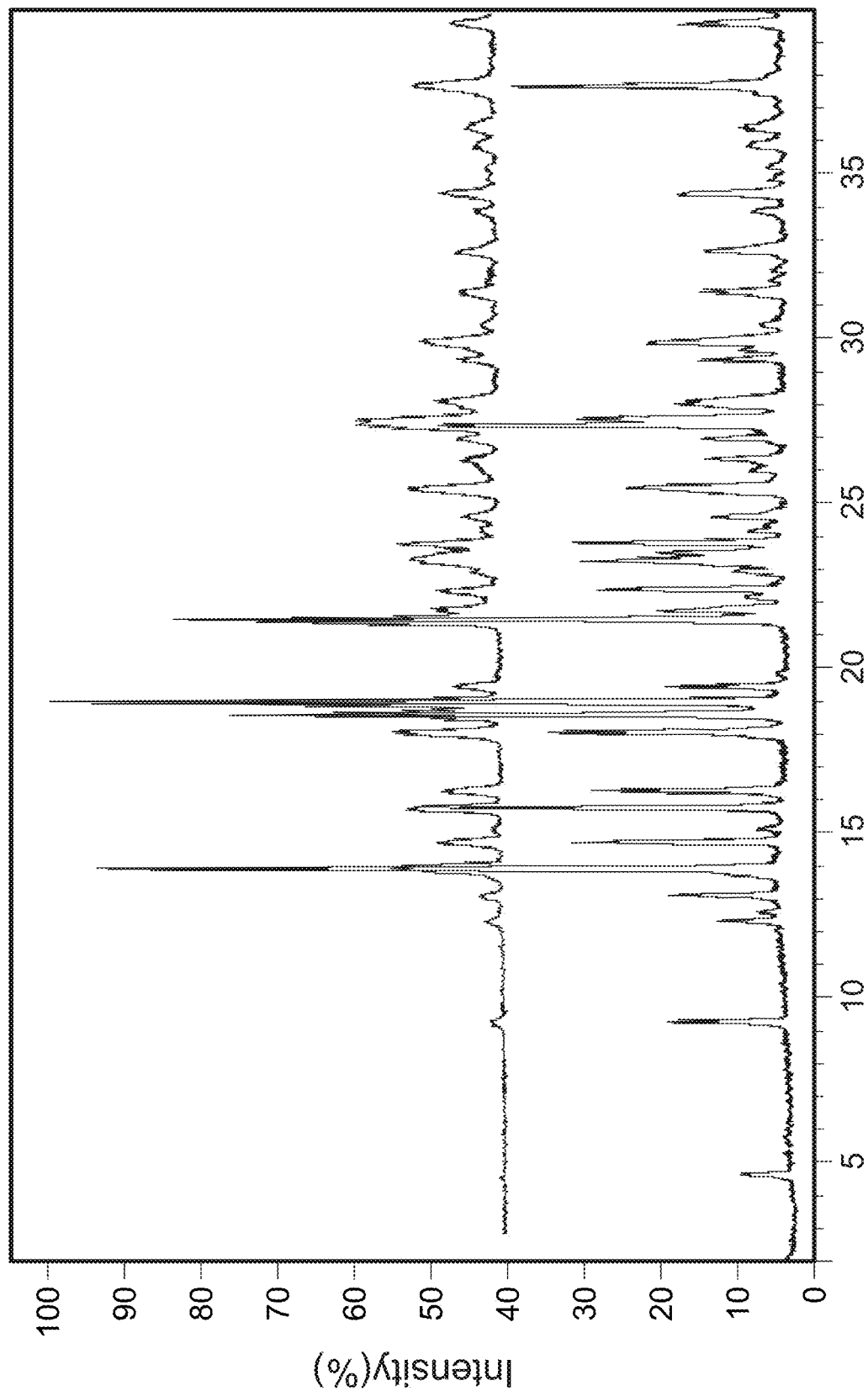
FIG. 19 shows an XRPD overlay of Compound 1, Form A before and after the DVS experiment described in Example 20.

Example 20. Hygroscopicity Evaluation of Compound 1 Form A and Compound 1, Form B Hygroscopicity of Compound 1, Form A and Compound 1, Form B was evaluated by DVS at 25° C. Based on DVS results, Compound 1, Form A is non-hygroscopic and Compound 1, Form B is slightly hygroscopic. After the DVS test, Compound 1, Form A showed no form change but crystallinity decreased and peaks became broad, suggesting potential instability of Compound 1, Form A. Compound 1, Form B had no form change after the DVS test. There was no form transition between Compound 1, Form A and Compound 1, Form B observed in the DVS plots, which suggests form transition kinetics between Compound 1, Form A and Compound 1, Form B is slow in bulk state. DVS data for the hygroscopicity evaluation is summarized in Table 18 and FIG. 19.

TABLE 18

Hygroscopicity Evaluation of Form A and Form B at 25° C.
DVS at 25° C., dm/dt = 0.002%

| | Form A | | | | Form B | | | |
|---|---|---|---|---|---|---|---|---|
| | Sorp. (%) | Desorp. (%) | Sorp. (%) | Desorp. (%) | Sorp. (%) | Desorp. (%) | Sorp. (%) | Desorp. (%) |
| 0% | 0.00 | 0.00 | 0.00 | 0.00 | // | 0.01 | 0.01 | // |
| 10% | 0.00 | 0.01 | 0.00 | 0.01 | // | 0.95 | 0.65 | // |
| 20% | −0.01 | 0.01 | 0.00 | 0.01 | // | 1.03 | 0.96 | // |
| 30% | 0.00 | 0.02 | 0.01 | 0.02 | // | 1.08 | 1.00 | // |
| 40% | 0.00 | 0.02 | 0.01 | 0.02 | 1.09 | 1.14 | 1.03 | 1.06 |
| 50% | 0.01 | // | // | 0.03 | 1.10 | 1.18 | 1.06 | 1.11 |
| 60% | 0.01 | // | // | 0.03 | 1.14 | 1.21 | 1.09 | 1.10 |
| 70% | 0.02 | // | // | 0.04 | 1.18 | 1.26 | 1.12 | 1.13 |
| 80% | 0.02 | // | // | 0.04 | 1.22 | 1.28 | 1.17 | 1.18 |
| 90% | 0.03 | // | // | 0.04 | 1.29 | 1.33 | 1.22 | 1.24 |
| 95% | 0.01 | // | // | 0.01 | 1.38 | 1.38 | 1.30 | 1.30 |
| XRPD after DVS test | No form change but crystallinity decreased and peaks became broad. | | | | No form change Error! Reference source not found. | | | |

// = Not carried out
Sorp. = Sorpotion
Desorp. = Desorption

Example 21. Water Activity Study

About 15 mg of Form A and 15 mg of Form B were added to the saturated solutions of different water activities and equilibrated at 25° C. and 50° C. for 4 days, respectively. The resulting suspensions were filtered, and the solid parts (wet cake) were investigated by XRPD to determine the polymorph.

Figure 20B:
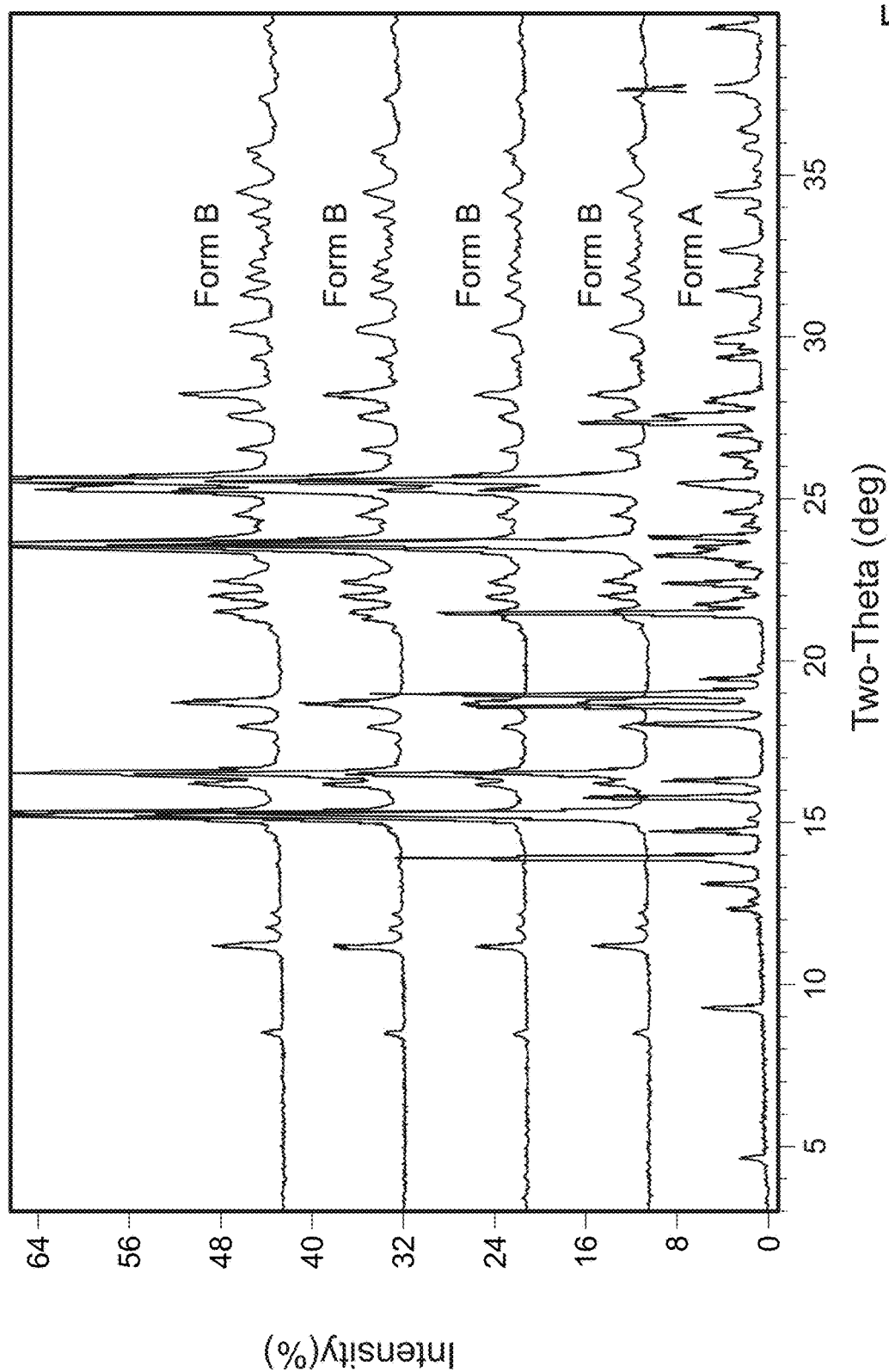
FIG. 20B shows an XRPD overlay of solids obtained from the water activity study described in Example 21, experiments 21E-21H.
Figure 21A:
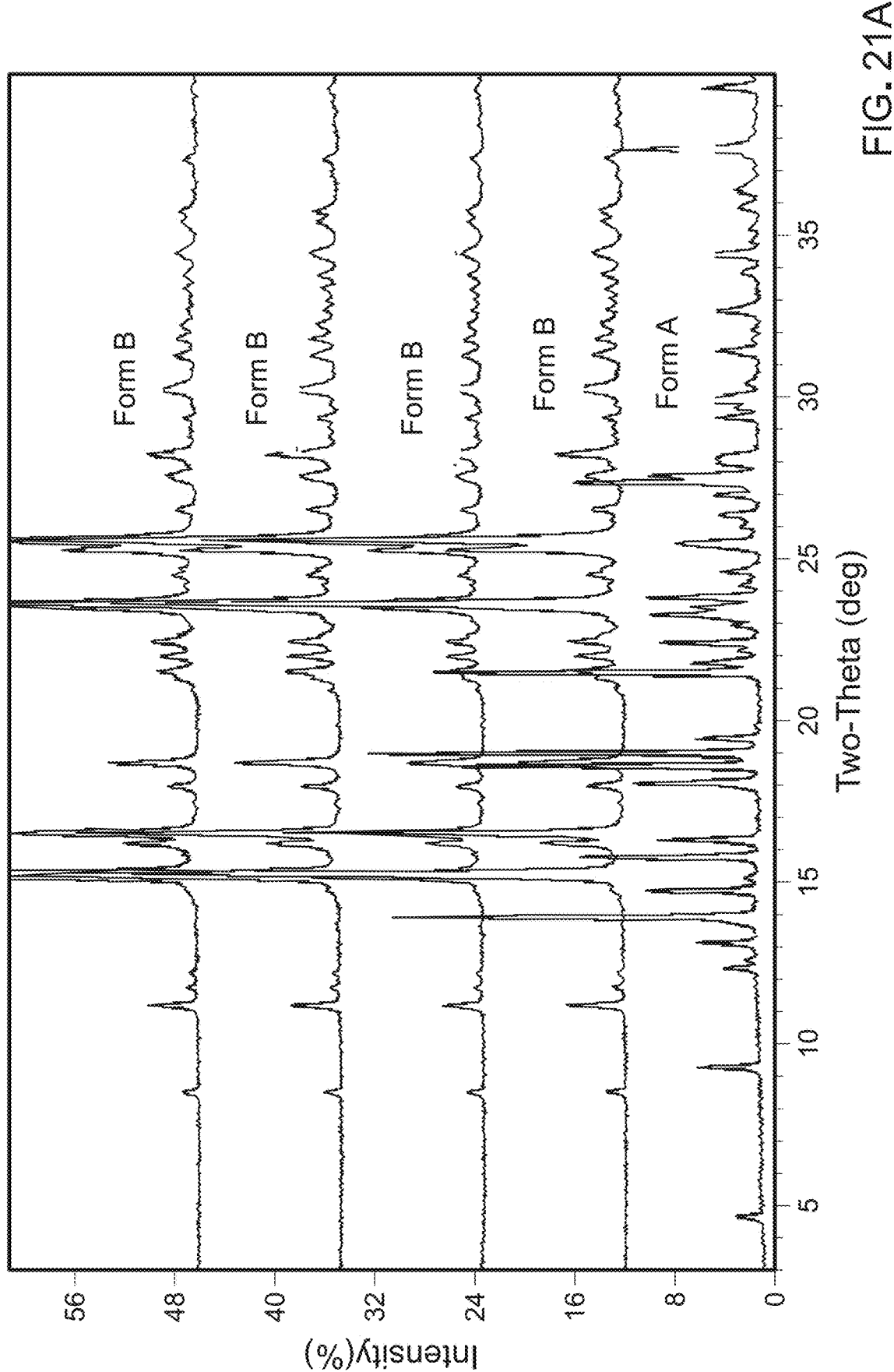
FIG. 21A shows an XRPD overlay of solids obtained from the water activity study described in Example 21, experiments 21I-21L.
Figure 21B:
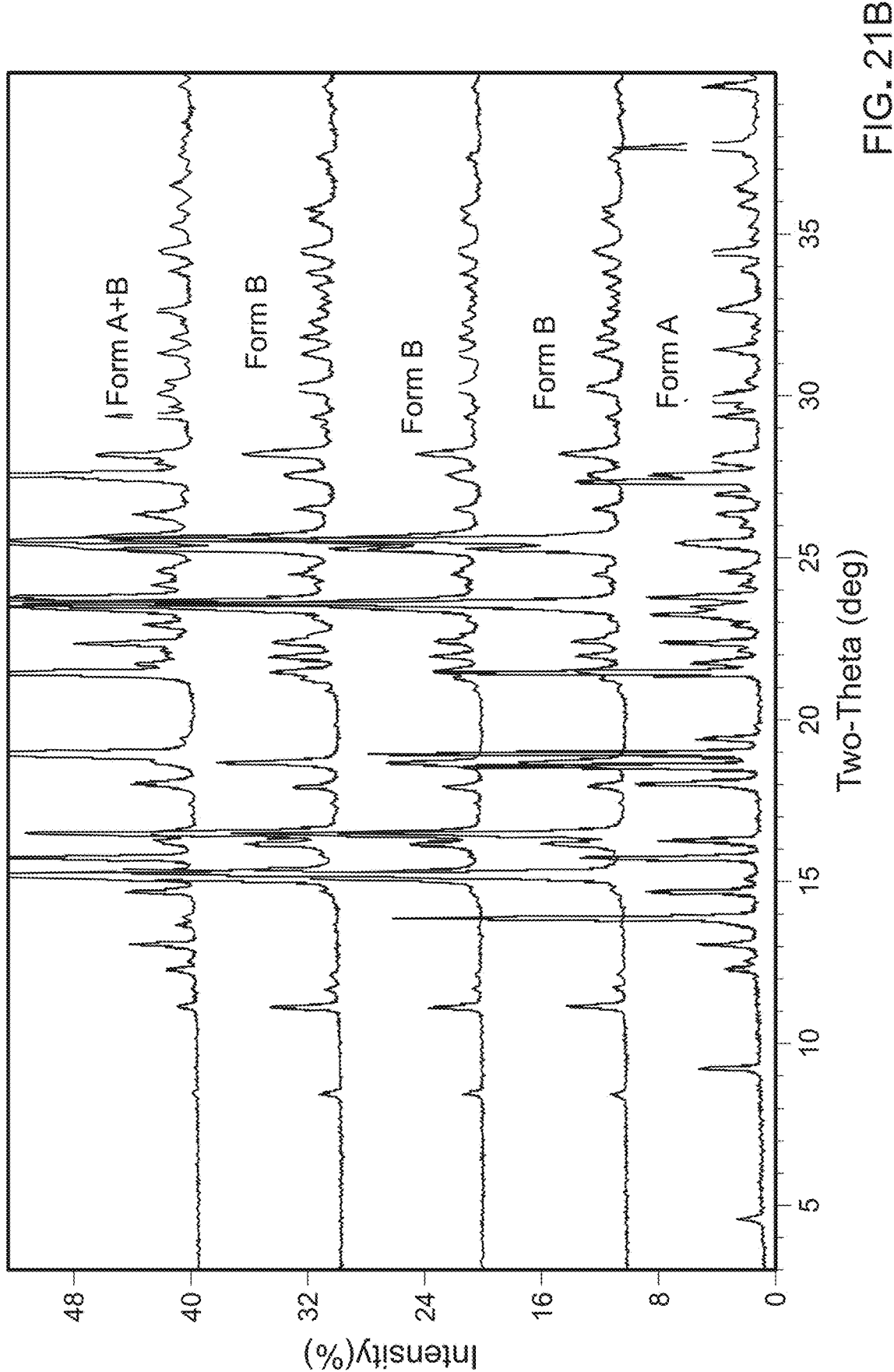
FIG. 21B shows an XRPD overlay of solids obtained from the water activity study described in Example 21, experiments 21M-21P.

According to XRPD results, Form B was obtained in methanol/water with water activity (a.w.) ranging from 0.1 to 0.9 at 25° C., as shown in FIGS. 20A-20B. At 50° C., Form B was obtained in methanol/water with a.w. ≥0.2, whereas a mixture of Form A and Form B was obtained in a.w. 0.1, as shown in FIGS. 21A-21B. These results suggest that the critical water activity between Form A and Form B is less than 0.1 at 25° C., but is between 0.1 and 0.2 at 50° C. Form B was more stable than Form A under ambient condition. Results of the water activity study are shown in Table 19. The water activity of the binary solvent system was calculated based on UNIFAC method (UNIQUAC Functional-group Activity Coefficients).

TABLE 19

Water activity study at 25° C.

| Exp. ID | Solvents | XRPD |
|---|---|---|
| 21A | Methanol/water (20:80, v/v) a.w. = 0.9 | Form B |
| 21B | Methanol/water (57:43, v/v) a.w. = 0.7 | Form B |
| 21C | Methanol/water (69:31, v/v) a.w. = 0.6 | Form B |
| 21D | Methanol/water (77:23, v/v) a.w. = 0.5 | Form B |
| 21E | Methanol/water (84:16, v/v) a.w. = 0.4 | Form B |
| 21F | Methanol/water (89:11, v/v) a.w. = 0.3 | Form B |

TABLE 19-continued

Water activity study at 25° C.

| Exp. ID | Solvents | XRPD |
|---|---|---|
| 21G | Methanol/water (93:7, v/v) a.w. = 0.2 | Form B |
| 21H | Methanol/water (97:3, v/v) a.w. = 0.1 | Form B |

TABLE 20

Water activity study at 50° C.

| Exp. ID | Solvents | XRPD |
|---|---|---|
| 21I | Methanol/water (20:80, v/v) a.w. = 0.9 | Form B |
| 21J | Methanol/water (57:43, v/v) a.w. = 0.7 | Form B |
| 21K | Methanol/water (69:31, v/v) a.w. = 0.6 | Form B |
| 21L | Methanol/water (77:23, v/v) a.w. = 0.5 | Form B |
| 21M | Methanol/water (84:16, v/v) a.w. = 0.4 | Form B |
| 21N | Methanol/water (89:11, v/v) a.w. = 0.3 | Form B |
| 21O | Methanol/water (93:7, v/v) a.w. = 0.2 | Form B |
| 21P | Methanol/water (97:3, v/v) a.w. = 0.1 | Form A + B |

Example 23. Solid State Stability Study

The two lots of Compound 1 were characterized by HPLC, PLM, XRPD, DSC, TGA, and KF. The physical characterization results suggest the crystalline state of the raw material. According to the stability study at different conditions, the two forms of compound were practically stable at different humidity for at least 4 weeks, with no XRPD pattern change and no growth of impurities were found. Table 21 shows representative stability data at 4 weeks, 6 weeks, and 8 weeks of testing.

TABLE 21

Stability results of two forms of Compound 1

| Test | Form A | | Form B | |
|---|---|---|---|---|
| Condition | 25° C./60% RH | 40° C./75% RH | 25° C./60% RH | 40° C./75% RH |

TABLE 21-continued

Stability results of two forms of Compound 1

| | Test | Form A | | Form B | |
|---|---|---|---|---|---|
| Initial | Purity | 99.46% | | 99.54% | |
| | Water content | 0.513% | | 3.677% | |
| | Crystallinity (XRPD & PLM) | Crystalline | | Crystalline | |
| | Particle shape & Size (PLM) | Irregular, 2-10 μm | | Irregular, 2-10 μm | |
| | Melting Point & Enthalpy (DSC) | 252.79° C./118.82 J/g | | 247.6° C./19.24 J/g; 253.6° C./112.04 J/g | |
| | Weight loss (TGA) (~120° C.) | 0.722% | | 2.233% | |
| 4 weeks | Purity | 99.48% | 99.46% | 99.55% | 99.55% |
| | Water content | — | — | — | — |
| | Crystallinity (XRPD & PLM) | Crystalline | Crystalline | Crystalline | Crystalline |
| | Particle shape & Size (PLM) | Irregular, 2-10 μm | Irregular, 2-8 μm | Irregular, 2-10 μm | Irregular, 2-8 μm |
| | Melting Point & Enthalpy (DSC) | 253.59° C./127.36 J/g | 252.74° C./119.65 J/g | 247.52° C./20.64 J/g; 253.65° C./109.30 J/g | 247.66° C./34.58 J/g; 253.60° C./103.31 J/g |
| | Weight loss (TGA) (~120° C.) | 0.981% | 0.884% | 2.374% | 2.319% |
| 6 weeks | Purity | 99.54% | 99.47% | 99.54% | 99.53% |
| | Water content | 0.784% | 0.547% | 3.361% | 3.301% |
| | Crystallinity (XRPD & PLM) | Crystalline | Crystalline | Crystalline | Crystalline |
| | Particle shape & Size (PLM) | Irregular, 2-10 μm | Irregular, 2-8 μm | Irregular, 2-20 μm | Irregular, 2-10 μm |
| | Melting Point & Enthalpy (DSC) | 252.94° C./118.20 J/g | 252.00° C./113.43 J/g | 247.52° C./25.83 J/g; 253.75° C./126.90 J/g | 252.68° C./44.13 J/g; 253.48° C./106.65 J/g |
| | Weight loss (TGA) (~120° C.) | 0.831% | 0.739% | 2.364% | 2.276% |
| 8 weeks | Purity | 99.51% | 99.53% | 99.54% | 99.55% |
| | Water content | 0.559% | 0.608% | 3.830% | 3.494% |
| | Crystallinity (XRPD & PLM) | Crystalline | Crystalline | Crystalline | Crystalline |
| | Particle shape & Size (PLM) | Irregular, 2-20 μm | Irregular, 2-20 μm | Irregular, 2-20 μm | Irregular, 2-10 μm |
| | Melting Point & Enthalpy (DSC) | 252.55° C./122.06 J/g | 252.57° C./123.80 J/g; | 247.48° C./19.03 J/g; 253.74° C./112.61 J/g | 246.77° C./35.23 J/g; 252.65° C./162.76 J/g |
| | Weight loss (TGA) (~120° C.) | 0.946% | 0.801% | 2.943% | 3.809% |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A solid form of Compound 1 having the formula:

Compound 1

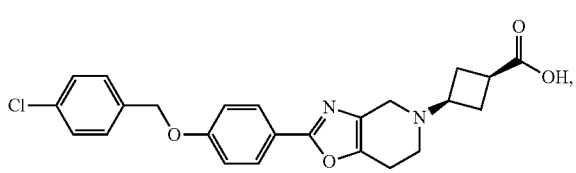

wherein the solid form is crystalline, and has characteristic XRPD peaks at about 13.9, about 19.0, and about 21.5 degrees 2-theta.

2. The solid form of claim 1, wherein the solid form has further characteristic XRPD peaks at about 4.7, about 9.3, about 15.8, about 18.6, and about 27.4 degrees 2-theta.

3. The solid form of claim 1, wherein the solid form has further characteristic XRPD peaks at about 4.7, about 9.3, about 12.4, about 13.1, about 14.8, about 15.8, about 16.3, about 18.1, about 18.6, about 19.5, about 21.8, about 22.1, about 22.4, about 23.0, about 23.3, about 23.5, about 23.8, about 24.6, about 25.5, about 26.4, about 27.0, about 27.4, about 27.5, about 28.1, about 29.4, about 29.8, about 29.9, about 31.4, about 32.7, about 34.4, about 35.9, about 36.4, about 37.7, and about 39.6 degrees 2-theta.

* * * * *